US007576183B2

(12) United States Patent
Gupta et al.

(10) Patent No.: US 7,576,183 B2
(45) Date of Patent: Aug. 18, 2009

(54) STRUCTURE-BASED RECEPTOR MIMICS TARGETED AGAINST BACTERIAL SUPERANTIGEN TOXINS

(75) Inventors: Goutam Gupta, Santa Fe, NM (US); Elizabeth Hong-Geller, Los Alamos, NM (US); Patrick R. Shiflett, Los Alamos, NM (US); Nancy M. Lehnert, Albuquerque, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 569 days.

(21) Appl. No.: 10/746,959

(22) Filed: Dec. 24, 2003

(65) Prior Publication Data

US 2005/0260222 A1 Nov. 24, 2005

(51) Int. Cl.
*C01K 16/00* (2006.01)
*C01K 1/00* (2006.01)
*G01N 33/53* (2006.01)

(52) U.S. Cl. .................... 530/387.1; 530/350; 435/7.1
(58) Field of Classification Search .................. 435/7.1; 530/350, 387.1
See application file for complete search history.

(56) References Cited

U.S. PATENT DOCUMENTS

| 4,751,180 | A | 6/1988 | Cousens et al. |
| 4,935,233 | A | 6/1990 | Bell et al. |
| 5,990,275 | A | 11/1999 | Whitlow et al. |
| 2004/0224408 | A1* | 11/2004 | Girard et al. ............ 435/455 |

FOREIGN PATENT DOCUMENTS

WO          WO01/70245      *  9/2001

OTHER PUBLICATIONS

Anderson et al. The Journal of Biological Chemistry, vol. 276, No. 36, pp. 33452-33457, 2001.*
Hong-Geller et al. Journal of Biological Chemistry, vol. 279, No. 7, pp. 5676-5684, paper published Feb. 13, 2004, Electronically available Nov. 16, 2003.*
Anderson et al., Journal of Biological Chemistry, vol. 276, No. 36, pp. 33452-33457, 2001.*
Riley et al., Protein Engineering, vol. 9, No. 2 pp. 223-230, 1996.*
Kieke et al. Journal of MOlecular Biology vol. 307, pp. 1305-1315, 2001.*
Lehnert et al., 2001, "Structure-Based Design of a Bispecific Receptor Mimic That Inhibits T Cell Responses to a Superantigen", Biochemistry 40: 4222-8.
Jardetzky, et al., 1994, "Three-Dimensional Structure of a Human Class II Histocompatibility Molecule Complexed with Superantigen", Nature 368: 711-8.
Kim et al., 1994, "Toxic Shock Syndrome Toxin-1 Complexed with a Class II Major Histocompatibility Molecule HLA-DR1", Science 266: 1870-4.

Fields et al., 1996, "Crystal Structure of a T-Cell Receptor β-Chain Complexed with a Superantigen", Nature 384: 188-92.
Li et al., 1998, "Three-Dimensional Structure of the Complex Between a T Cell Receptor β Chain and the Superantigen Staphylococcal Enterotoxin B", Immunity 9: 807-816.
Reiser et al., 1996, "Costimulatory B7 Molecules in the Pathogenesis of Infectious and Autoimmune Diseases", N Engl J Med 335: 1369-77.
Haddad, J., 2002, "Cytokines and Related Receptor-Mediated Signaling Pathways", Biochem. Biophys. Res. Comm. 297: 700-13.
Choi et al., 1989, "Interaction of *Staphylococcus aureus* Toxin "Superantigens" with Human T Cells", Proc Natl Acad Sci U S A 86: 8941-5.
Sundberg et al., 2002, "So Many Ways of Getting In the Way: Diversity in the Molecular Architecture of Superantigen-Dependent T-Cell Signaling Complexes", Curr. Opin. Immunol. 14: 36-44.
Papageorgiou et al., 1998, "Crystal Structure of Microbial Superantigen Staphylococcal Enterotoxin B at 1.5 Resolution: Implications for Superantigen Recognition by MHC Class II Molecules and T-Cell Receptors", J. Mol. Biol. 277: 61-79.
Prasad et al., 1997, "Refined Structures of Three Crystal Forms of Toxic Shock Syndrome Toxin-1 and of a Tetramutant with Reduced Activity", Protein Sci. 6: 1220-7.
Chi et al., 2002, "Zinc-Mediated Dimerization and Its Effect on Activity and Conformation of Staphylococcal Enterotoxin Type C", J. Biol. Chem. 277: 22839-46.
Kappler et al., 1989, "Vβ-Specific Stimulation of Human T Cells by Staphylococcal Toxins", Science 244: 811-813.
Fraser, 1989, "High-Affinity Binding of Staphylococcal Enterotoxins A and B to HLA-DR", Nature 339: 221-223.
Kreiswirth et al., 1993, "Evidence for a Clonal Origin of Methicillin Resistance in *Staphylococcus aureus*", Science 259: 227-230.
Pearson, 2002, 'Superbug' Hurdles Key Drug Barrier, Nature 418: 469.
Matthys et al., 1995, "Anti-Gamma Interferon and Anti-Interleukin-6 Antibodies Affect Staphylococcal Enterotoxin B-Induced Weight Loss, Hypoglycemia, and Cytokine Release in D-Galactosamine-Sensitized and Unsensitized Mice", Infect. Immun.63:1158-1164.
Papageorgiou et al., 1996, "Crystal Stucture of a Biologically Inactive Mutant of Toxic Shock Syndrome Toxin-1 at 2.5 A Resolution", Protein Sci. 5: 1737-41.

(Continued)

*Primary Examiner*—Robert Mondesi
*Assistant Examiner*—Khatol S. Shahnan-Shah
(74) *Attorney, Agent, or Firm*—Kenneth N. Sharples

(57) ABSTRACT

The invention provides therapeutic compositions useful in the treatment of bacterial superantigen mediated conditions, such as Toxic Shock Syndrome. The compositions comprise genetically engineered bifunctional polypeptides containing a specific T-cell receptor binding domain and a specific MHC class II receptor binding domain, each targeting non-overlapping epitopes on a superantigen molecule against which they are designed. The anti-superantigen "receptor mimetics" or "chimeras" are rationally designed to recreate the modality of superantigen binding directly to both the TCR and the MHC-II receptor, and are capable of acting as decoys for superantigen binding, effectively out-competing the host T-cell and MHC-II receptors, the natural host receptors.

3 Claims, 20 Drawing Sheets

OTHER PUBLICATIONS

Roussel et al., 1997, "Crystal Structure of the Streptococcal Superantigen SPE-C: Dimerization and Zinc Binding Suggest a Novel Mode of Interaction with MHC Class II Molecules", Nat. Struct. Biol. 4: 635-643.

Li et al., 1997, "The Superantigen Streptococcal Pyrogenic Exotoxin C (SPE-C) Exhibits a Novel Mode of Action", J. Exp. Med. 186: 375-383.

Proft et al., 1999, "Identification and Characterization of Novel Superantigens from *Streptococcus* pyogenes", J. Exp. Med. 189: 89-102.

Fraser et al., 2000, "Superantigens—Powerful Modifiers of the Immune System", Molecular Medicine Today 6: 125-132.

Rosec & Gigaud, 2002, "Staphylococcal Enterotoxin Genes of Classical and New Types Detected by PCR in France", Intl. Jl. Food Microbiol, 77:61-70.

Hakansson et al., 2000, "The Crystal Structure of Staphylococcal Enterotoxin H: Implications for Binding Properties to MHC Class II and TcR Molecules", JMB, 302:527-537.

Cottrez et al., 1994, "Analysis of the Vβ Specificity of Superantigen Activation with a Rapid and Sensitive Method using RT PCR and an Automatic DNA Analyser", J. Immunol. Methods, 172:85-94.

Kieke et al., 2001, "High Affinity T Cell Receptors from Yeast Display Libraries Block T Cell Activation by Superantigens", J. Mol. Biol. 307: 1305-1315.

Fontenot et al., 1995, "Human Immunodeficiency Virus (HIV) Antigens: Structure and Serology of Multivalent Human Mucin MUC1-HIV V3 Chimeric Proteins", Proc. Natl. Acad. Sci USA 92:315-319.

Maratea et al,. 1985, "Deletion and Fusioin Analysis of the Phage φX174 Lysis Gene *E*", Gene 40:39-46.

Murphy et al., 1986, "Genetic Contruction, Expression, and Melanoma-Selective Cytotoxicity of a Diphtheria Toxin-Related αMelanocyte-Stimulating Hormone Fusion Protein", Proc. Natl. Acad. Sci. USA 83:8258-8262.

Ridgway et al., 1996, "Knobs-Into-Holes' Engineering of Antibody $C_H 3$ Domains for Heavy Chain Heterodimerization", Protein Eng. 9: 617-621.

Adamian & Liang, "Interhelical Hydrogen Bonds and Spatial Motifs in Membrane Proteins: Polar Clamps and Serine Zippers", Proteins 47:209-218, 2002.

Atwell et al., 1997, "Stable Heterodimers from Remodeling the Domain Interface of a Homodimer Using a Phage Display Library", J. Mol. Biol. 270: 26-35.

Galanos et al., 1979, "Galactosamine-induced Sensitization to the Lethal Efects of Endotoxin", Proc. Natl. Acad. Sci. USA 76: 5939-5943.

Miethke et al. 1992, "T Cell-Mediated Lethal Shock Triggered in Mice by the Superantigen Staphylococcal Enterotoxin B: Critical Role of Tumor Necrosis Factor", J. Exp. Med. 175: 91-98.

Lowell et al., 1996, "Intranasal and Intramuscular Proteosome-Stphylococcal Enterotoxin B (SEG) Toxoid Vaccines: Immunogenicity and Efficacy against Lethal SEB Intoxication in Mice", Infect. Immun. 64:1706-1713.

Balaban et al., 2000, "Prevention of Diseases Caused by *Staphylococcus aureus* using the Peptide RIP", Peptides 21:1301-1311.

Bernal et al., 1999, "Superantigens in Human Disease", Jl. Clin. Immunol., 19:149-157.

Leung et al., 1995, "The Role of Superantigens in Skin Disease", Jl. Invest. Dermatology, 105:37S-42S.

Sanchez and Sali, 1999, "Comparative Protein Structure Modeling in Genomics", J. Comp. Phys. 151: 388-401.

Arcus et al, 2002, "The Three-Dimensional Structure of a Superantigen-Like Protein, SET3, from a Pathogenicity Island of the *Staphylococcus aureus* Genome", J Biol. Chem. 277: 32274-81.

Arcus et al., 2000, "Conservation and Variation in Superantigen Structure and Activity Highlighted by the Three-Dimensional Structures of Two New Superantigens from *Streptococcus* pyogenes", J. Mol Biol. 299: 157-68.

McCormick et al, J. Immun. 2003, 171:1385.

Rogers and Zhang, Mol. Immun. 1997, 34 (3):263.

Leder et al., J. Exp. Med., The Rockefeller University Press, vol. 187, No. 6, Mar. 16, 1998 pp. 823-833; P.

Andersen et al., J. Biol. Chem. 2001, 276 (36): 33452.

Hong-Geller et al., J. Biol. Chem. 2004, 279 (7): 5676.

Mollhoff et al., J. Mol Recog. 2005, 18: 73.

\* cited by examiner

FIG. 1C

DRα1-linker-TcRVβ chimera prevents superantigen from binding to the immune cells and thereby blocks pathogenesis

Delayed response
- Anergy
- Immunesuppression
- Apoptosis

Antigen Presenting Cell

T Helper Cell

Massive cytokine release | Excessive T cell proliferation

Initial response

```
                α1                          β1            β2                                β3                    α2
SEB    ESQPDPKPDELHKSSKFTGLMENMKVLYDDNHVSAINVKSIDQFLYFDLIYSIKDTKLGNYDNVRVEF-KNKDLADKYKDKY
              10        20        30        40        50        60        70        80
SEC3   ESQPDDPMPDDLHKSSEFTGTMGNMKYLYDDHYVSATKVKSVDKFLAHDLIYNINDKK-NYDKVKIEL-LNEDLANKYKDEV
              10        20        30        40        50        60        70        80
TSST1  ------------STNDNIKDLLDWYSSGSDTFTNSEVLDNSLGSMRIKNTD----G-SEIIFSEYYSPAFTKGEK
                          10        20        30        40            50        60

β4              flexible loop region              β5       β6                     β7        β8                    β9 α3
SEB    VDVFGANYYYQCYFSKKTNDINS---------KRYTCMYGGVTEHNGNQLD--KYRSITVRVFEDGKNLLSFD-VQINKKVTAQE
             90       100                  110              120       130       140       150
SEC3   VDVYGSNYYVNCYFSSKDNV---------V---TSCKTCMYGGITKHEGNHFDNGNLQNVLIRVYENKRNTISFE-VQTDKKSVTAQE
             90       100                  110              120       130       140       150
TSST1  VDLNTKRTKKSQHTSG---------II-FQISGV-TNTE---KLPTPIELPLKVKVHG-KDSPLKYWPKFDKKQLAIST
             70        80            90                100       110       120

α3                                                                      β10                                β11                          α4                                                    β12                              β13
SEB    LDYLTRHYLVNKKLYEFNNSPYETGYIKFIENENSEEWYDMMPAPGDKFDQSKYLMMYN-DNKMVDSKDVKIEVYLTTKK-
             160       170       180       190       200       210       220       230
SEC3   LDIKARNFLINKKNLYEFNSSPYETGYIKFIESNGNTFWYDMMPAPGDKFDQSKYLMMYK-DNKMVDSKSVKIEEVHLTTKNG
             140       150       160       170       180       190       200       210       220       230
TSST1  LDFEIRHQLTQIHGLYRSSD----KTGGYWKFTMNDGSIYQSDL---LSKKFEYNTEKP-----PINIDEIKTEFAEIN--
             140       150       160       170       180       190
```

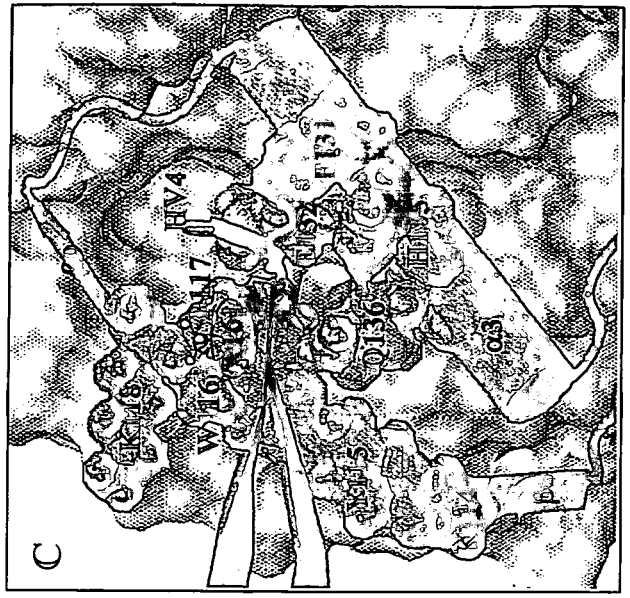
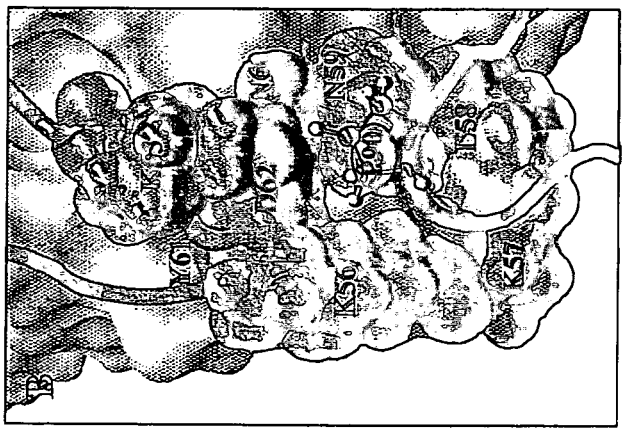
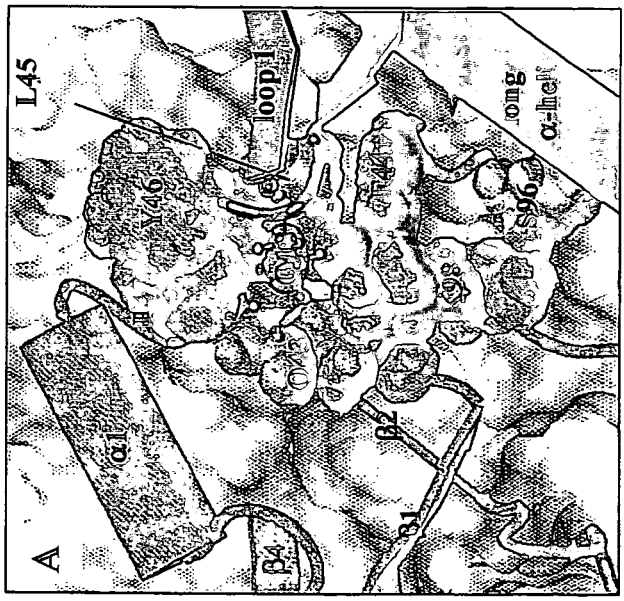
FIG. 9

FIG. 11

TSST-1

SEC3

SEB

FIG. 13B

TSST-1 complex

SEC3 complex

SEB complex

FIG. 14

TSST-1 complex

SEC3 complex

SEB complex

FIG. 15B
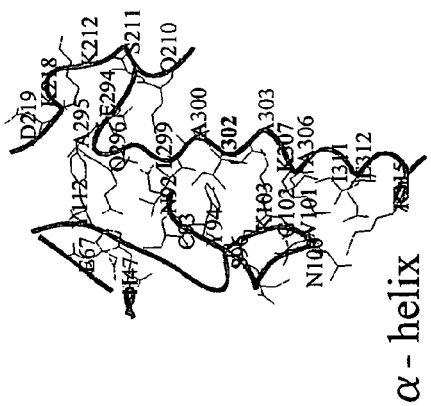
α - helix
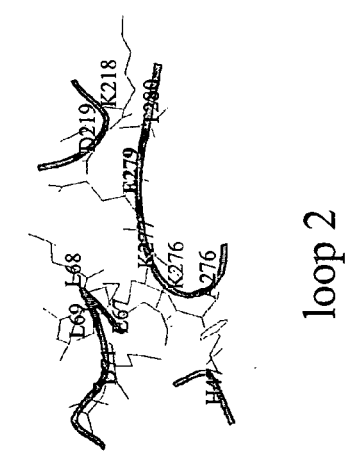
loop 2
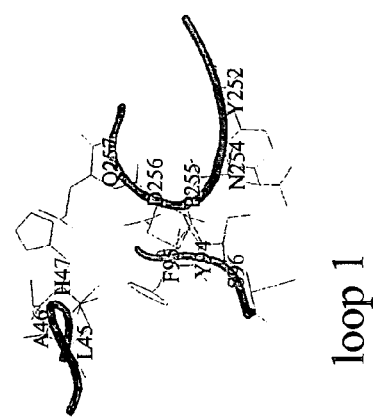
loop 1
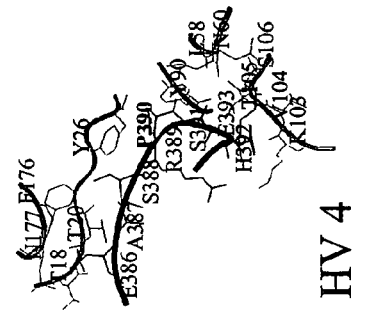
HV 4
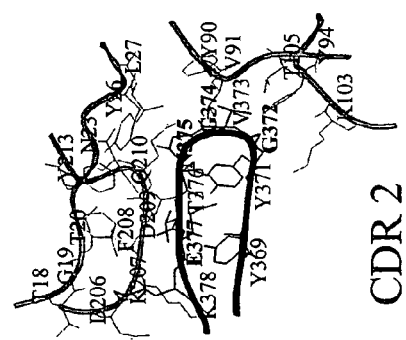
CDR 2
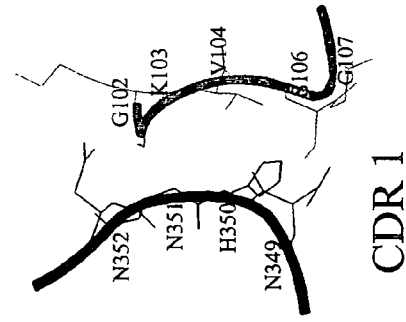
CDR 1

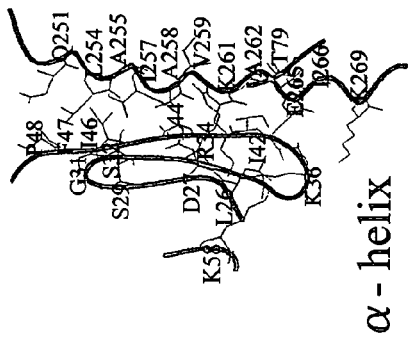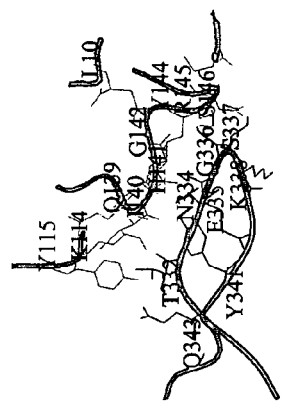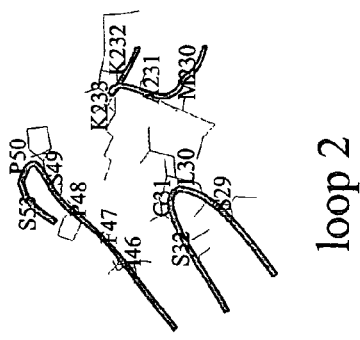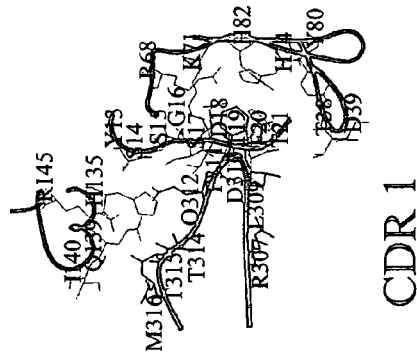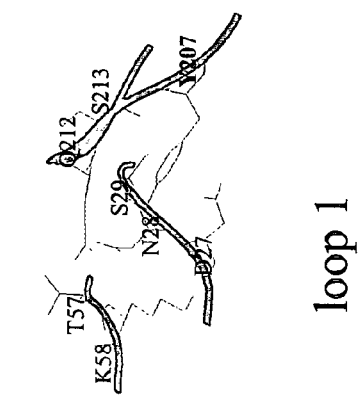
FIG. 15C

SEQUENCE LISTING

<160> NUMBER OF SEQ ID NOS: 22

<210> SEQ ID NO 1
<211> LENGTH: 84

```
<212> TYPE: PRT
<213> ORGANISM: Homo Sapiens

<400> SEQUENCE: 1

Ile Lys Glu Glu His Val Ile Ile Gln Ala Glu Phe Tyr Leu Asn Pro
1               5                   10                  15

Asp Gln Ser Gly Glu Phe Met Phe Asp Phe Asp Gly Asp Glu Ile Phe
            20                  25                  30

His Val Asp Met Ala Lys Lys Glu Thr Val Trp Arg Leu Glu Glu Phe
        35                  40                  45

Gly Arg Phe Ala Ser Phe Glu Ala Gln Gly Ala Leu Ala Asn Ile Ala
    50                  55                  60

Val Asp Lys Ala Asn Leu Glu Ile Met Thr Lys Arg Ser Asn Tyr Thr
65                  70                  75                  80

Pro Ile Thr Asn

<210> SEQ ID NO 2
<211> LENGTH: 83
<212> TYPE: PRT
<213> ORGANISM: Homo Sapiens

<400> SEQUENCE: 2

Ala Ser Val Ser Gln His Pro Ser Arg Val Lys Ile Glu Cys Arg Ser
1               5                   10                  15

Leu Asp Phe Gln Ala Thr Thr Met Phe Trp Tyr Arg Gln Phe Pro Lys
            20                  25                  30

Gln Ser Leu Met Leu Met Ala Thr Ser Asn Glu Gly Ser Lys Ala Thr
        35                  40                  45

Tyr Glu Gln Gly Val Glu Lys Asp Lys Phe Leu Ile Asn His Ala Ser
    50                  55                  60

Leu Thr Leu Val Thr Ser Ala His Pro Glu Asp Ser Ser Phe Tyr Ile
65                  70                  75                  80

Cys Ser Ala

<210> SEQ ID NO 3
<211> LENGTH: 74
<212> TYPE: PRT
<213> ORGANISM: Homo Sapiens

<400> SEQUENCE: 3

Val Phe Leu Glu Cys Val Gln Asp Asn Asp His Glu Asn Met Phe Trp
1               5                   10                  15

Tyr Arg Gln Asp Pro Gly Leu Gly Leu Arg Leu Ile Tyr Phe Ser Tyr
            20                  25                  30

Asp Val Lys Asn Lys Glu Lys Gly Asp Ile Pro Glu Gly Tyr Ser Val
        35                  40                  45

Ser Arg Glu Lys Lys Glu Arg Phe Ser Leu Ile Leu Glu Ser Ala Ser
    50                  55                  60

Thr Asn Gln Thr Ser Met Tyr Leu Cys Ala
65                  70

<210> SEQ ID NO 4
<211> LENGTH: 75
<212> TYPE: PRT
<213> ORGANISM: Mus musculus

<400> SEQUENCE: 4

Ala Ser Val Thr Leu Ser Cys Asn Gln Thr Asn Asn His Asn Asn Met
```

```
                    1               5                   10                  15
Tyr Trp Tyr Arg Gln Asp Thr Gly His Gly Leu Arg Leu Ile His Tyr
                    20                  25                  30

Ser Tyr Gly Val Asn Thr Glu Lys Gly Asp Ile Pro Asp Gly Tyr Glu
        35                  40                  45

Ala Ser Arg Pro Ser His Glu Asn Phe Ser Leu Ile Leu Val Ser Ala
    50                  55                  60

Thr Pro Ser Gln Ser Ser Val Tyr Phe Cys Ala
65                  70                  75

<210> SEQ ID NO 5
<211> LENGTH: 14
<212> TYPE: PRT
<213> ORGANISM: Homo Sapiens

<400> SEQUENCE: 5

Gly Ser Thr Ala Pro Pro Ala Gly Ser Thr Ala Pro Pro Ala
1               5                   10

<210> SEQ ID NO 6
<211> LENGTH: 32
<212> TYPE: PRT
<213> ORGANISM: Artificial Sequence
<220> FEATURE:
<223> OTHER INFORMATION: engineered peptide

<400> SEQUENCE: 6

Val Ala Gln Leu Glu Glu Lys Val Lys Thr Leu Arg Ala Gln Asn Tyr
1               5                   10                  15

Glu Leu Lys Ser Arg Val Gln Arg Leu Arg Glu Gln Val Ala Gln Leu
                20                  25                  30

<210> SEQ ID NO 7
<211> LENGTH: 32
<212> TYPE: PRT
<213> ORGANISM: Artificial Sequence
<220> FEATURE:
<223> OTHER INFORMATION: engineered peptide

<400> SEQUENCE: 7

Val Asp Glu Leu Gln Ala Glu Val Asp Gln Leu Gln Asp Glu Asn Tyr
1               5                   10                  15

Ala Leu Lys Thr Lys Val Ala Gln Leu Arg Lys Lys Val Glu Lys Leu
                20                  25                  30

<210> SEQ ID NO 8
<211> LENGTH: 172
<212> TYPE: PRT
<213> ORGANISM: Artificial Sequence
<220> FEATURE:
<223> OTHER INFORMATION: synthetic chimera polypeptide

<400> SEQUENCE: 8

Ile Lys Glu Glu His Val Ile Ile Gln Ala Glu Phe Tyr Leu Asn Pro
1               5                   10                  15

Asp Gln Ser Gly Glu Phe Met Phe Asp Phe Asp Gly Asp Glu Ile Phe
                20                  25                  30

His Val Asp Met Ala Lys Lys Glu Thr Val Trp Arg Leu Glu Glu Phe
            35                  40                  45

Gly Arg Phe Ala Ser Phe Glu Ala Gln Gly Ala Leu Ala Asn Ile Ala
        50                  55                  60
```

```
Val Asp Lys Ala Asn Leu Glu Ile Met Thr Lys Arg Ser Asn Tyr Thr
 65                  70                  75                  80

Pro Ile Thr Asn Gly Ser Thr Ala Pro Pro Ala Gly Ser Thr Ala Pro
                 85                  90                  95

Pro Ala Val Phe Leu Glu Cys Val Gln Asp Asn Asp His Glu Asn Met
            100                 105                 110

Phe Trp Tyr Arg Gln Asp Pro Gly Leu Gly Leu Arg Leu Ile Tyr Phe
        115                 120                 125

Ser Tyr Asp Val Lys Asn Lys Glu Lys Gly Asp Ile Pro Glu Gly Tyr
    130                 135                 140

Ser Val Ser Arg Glu Lys Lys Glu Arg Phe Ser Leu Ile Leu Glu Ser
145                 150                 155                 160

Ala Ser Thr Asn Gln Thr Ser Met Tyr Leu Cys Ala
                165                 170
```

<210> SEQ ID NO 9
<211> LENGTH: 173
<212> TYPE: PRT
<213> ORGANISM: Artificial Sequence
<220> FEATURE:
<223> OTHER INFORMATION: synthetic chimera peptide

<400> SEQUENCE: 9

```
Ile Lys Glu Glu His Val Ile Ile Gln Ala Glu Phe Tyr Leu Asn Pro
  1               5                  10                  15

Asp Gln Ser Gly Glu Phe Met Phe Asp Phe Asp Gly Asp Glu Ile Phe
                 20                  25                  30

His Val Asp Met Ala Lys Lys Glu Thr Val Trp Arg Leu Glu Glu Phe
             35                  40                  45

Gly Arg Phe Ala Ser Phe Glu Ala Gln Gly Ala Leu Ala Asn Ile Ala
         50                  55                  60

Val Asp Lys Ala Asn Leu Glu Ile Met Thr Lys Arg Ser Asn Tyr Thr
 65                  70                  75                  80

Pro Ile Thr Asn Gly Ser Thr Ala Pro Pro Ala Gly Ser Thr Ala Pro
                 85                  90                  95

Pro Ala Ala Ser Val Thr Leu Ser Cys Asn Gln Thr Asn Asn His Asn
            100                 105                 110

Asn Met Tyr Trp Tyr Arg Gln Asp Thr Gly His Gly Leu Arg Leu Ile
        115                 120                 125

His Tyr Ser Tyr Gly Val Asn Thr Glu Lys Gly Asp Ile Pro Asp Gly
    130                 135                 140

Tyr Glu Ala Ser Arg Pro Ser His Glu Asn Phe Ser Leu Ile Leu Val
145                 150                 155                 160

Ser Ala Thr Pro Ser Gln Ser Ser Val Tyr Phe Cys Ala
                165                 170
```

<210> SEQ ID NO 10
<211> LENGTH: 181
<212> TYPE: PRT
<213> ORGANISM: Artificial Sequence
<220> FEATURE:
<223> OTHER INFORMATION: synthetic chimera polypeptide

<400> SEQUENCE: 10

```
Ile Lys Glu Glu His Val Ile Ile Gln Ala Glu Phe Tyr Leu Asn Pro
  1               5                  10                  15

Asp Gln Ser Gly Glu Phe Met Phe Asp Phe Asp Gly Asp Glu Ile Phe
                 20                  25                  30
```

His Val Asp Met Ala Lys Lys Glu Thr Val Trp Arg Leu Glu Glu Phe
            35                  40                  45

Gly Arg Phe Ala Ser Phe Glu Ala Gln Gly Ala Leu Ala Asn Ile Ala
        50                  55                  60

Val Asp Lys Ala Asn Leu Glu Ile Met Thr Lys Arg Ser Asn Tyr Thr
65                  70                  75                  80

Pro Ile Thr Asn Gly Ser Thr Ala Pro Pro Ala Gly Ser Thr Ala Pro
                85                  90                  95

Pro Ala Ala Ser Val Ser Gln His Pro Ser Arg Val Lys Ile Glu Cys
            100                 105                 110

Arg Ser Leu Asp Phe Gln Ala Thr Thr Met Phe Trp Tyr Arg Gln Phe
        115                 120                 125

Pro Lys Gln Ser Leu Met Leu Met Ala Thr Ser Asn Glu Gly Ser Lys
    130                 135                 140

Ala Thr Tyr Glu Gln Gly Val Glu Lys Asp Lys Phe Leu Ile Asn His
145                 150                 155                 160

Ala Ser Leu Thr Leu Val Thr Ser Ala His Pro Glu Asp Ser Ser Phe
                165                 170                 175

Tyr Ile Cys Ser Ala
            180

<210> SEQ ID NO 11
<211> LENGTH: 28
<212> TYPE: DNA
<213> ORGANISM: Artificial Sequence
<220> FEATURE:
<223> OTHER INFORMATION: synthetic DNA encoding chimeric polypeptide

<400> SEQUENCE: 11
gatcagatct atcaaagaag aacatgtg                                      28

<210> SEQ ID NO 12
<211> LENGTH: 27
<212> TYPE: DNA
<213> ORGANISM: Artificial Sequence
<220> FEATURE:
<223> OTHER INFORMATION: synthetic oligonucleotide primer

<400> SEQUENCE: 12
gatcgctagc cgctggtggc gccgtcg                                       27

<210> SEQ ID NO 13
<211> LENGTH: 104
<212> TYPE: DNA
<213> ORGANISM: Artificial Sequence
<220> FEATURE:
<223> OTHER INFORMATION: synthetic oligonucleotide

<400> SEQUENCE: 13
ctagccaaca tccgagcagg gttatctgta agagtggaac ctctgtgaag atcgagtgcc   60
gttccctgga ctttcaggcc acaactatgt tttggtaccg tcag                   104

<210> SEQ ID NO 14
<211> LENGTH: 105
<212> TYPE: DNA
<213> ORGANISM: Artificial Sequence
<220> FEATURE:
<223> OTHER INFORMATION: synthetic oligonucleotide

<400> SEQUENCE: 14

```
cgggaactga cggtaccaaa acatagttgt ggcctgaaag tccagggaac ggcactcgat    60
cttcacagag gttccactct tacagataac cctgctcgga tgttg                   105
```

<210> SEQ ID NO 15
<211> LENGTH: 117
<212> TYPE: DNA
<213> ORGANISM: Artificial Sequence
<220> FEATURE:
<223> OTHER INFORMATION: synthetic oligonucleotide

<400> SEQUENCE: 15

```
ttcccgaaac agagtctcat gctgatggca cttccaatga gggctccaag gccacatacg    60
agcaaggcgt cgagaaggac aagtttctca tcaaccatgc aagcctgacc ttgtccg      117
```

<210> SEQ ID NO 16
<211> LENGTH: 116
<212> TYPE: DNA
<213> ORGANISM: Artificial Sequence
<220> FEATURE:
<223> OTHER INFORMATION: synthetic oligonucleotide

<400> SEQUENCE: 16

```
aattcggaca aggtcaggct tgcatggttg atgagaaact tgtccttctc gacgccttgc    60
tcgtatgtgg ccttggagcc ctcattggaa gttgccatca gcatgagact ctgttt       116
```

<210> SEQ ID NO 17
<211> LENGTH: 28
<212> TYPE: DNA
<213> ORGANISM: Artificial Sequence
<220> FEATURE:
<223> OTHER INFORMATION: synthetic oligonucleotide primer

<400> SEQUENCE: 17

```
gatcagatct atcaaagaag aacatgtg                                      28
```

<210> SEQ ID NO 18
<211> LENGTH: 33
<212> TYPE: DNA
<213> ORGANISM: Artificial Sequence
<220> FEATURE:
<223> OTHER INFORMATION: synthetic oligonucleotide primer

<400> SEQUENCE: 18

```
ggacaaggtc aggcttgcat ggttgatgag aaa                                33
```

<210> SEQ ID NO 19
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 19

```
accctgaccg ttacctctgc tcacccggaa gactcttctt tctacatctg ctctgcttag    60
g                                                                   61
```

<210> SEQ ID NO 20
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 20

```
aattcctaag cagagcagat gtagaaagaa gagtcttccg ggtgagcaga ggtaacggtc    60
agggt                                                                65

<210> SEQ ID NO 21
<211> LENGTH: 31
<212> TYPE: DNA
<213> ORGANISM: Artificial Sequence
<220> FEATURE:
<223> OTHER INFORMATION: synthetic oligonucleotide primer

<400> SEQUENCE: 21
gatcgctagc gtgacattga gctgtaatca g                                   31

<210> SEQ ID NO 22
<211> LENGTH: 34
<212> TYPE: DNA
<213> ORGANISM: Artificial Sequence
<220> FEATURE:
<223> OTHER INFORMATION: synthetic oligonucleotide primer

<400> SEQUENCE: 22
gatcgaattc ctaggcacag aagtacactg atgt                                34
```

STRUCTURE-BASED RECEPTOR MIMICS TARGETED AGAINST BACTERIAL SUPERANTIGEN TOXINS

STATEMENT REGARDING GOVERNMENT RIGHTS

This invention was made with government support under grant number DE-FG02-98ER62647 from the United States Department of Energy and Contract No. W-7405-ENG-36 awarded by the United States Department of Energy to The Regents of The University of California. The government has certain rights in this invention.

FIELD OF THE INVENTION

The invention involves the treatment of toxic shock syndrome, food poisoning, and skin disorders caused by exposure to superantigens produced during infection with bacterial pathogens such as *Staphylcoccus aureus* and *Streptococcus pyogenes,* using chimeric molecules designed to mimic the unique interaction between superantigen molecules and the host T cell and MHC II receptors.

STATEMENT REGARDING COLOR DRAWINGS

This patent or application file contains at least one drawing executed in color. Copies of this patent or patent application publication with color drawings will be provided by the United States Patent and Trademark Office upon request and payment of the necessary fee.

BACKGROUND OF THE INVENTION

Bacterial and viral superantigens (SAGS) represent some of the most potent toxins known to exist and can cause massive overstimulation of the host immune system, initially through cytokine release, T cell proliferation, and finally through T cell anergy and apoptosis (Marrack and Kappler, 1990, Science 248:1066; Ulrich et al., 1995, Trends Microbiol. 3: 463-468; Papageorgiou and Acharya, 2000, Trends Micobiol 8: 369-375).

Superantigens secreted by the bacterial pathogen *Staphyloccocus aureus* (*S. aureus*) overstimulate the host immune system by binding as intact proteins to the DRα1 domain of the MHC class II receptor and the TCRVβ domain from the T cell receptor, thereby activating a large population of T cells and causing the excessive release of a number of cytokines. Initially, *S. aureus* SAGs compromise the immune system by inducing the large-scale release of cytokines, such as IL-2, TNF-α, and IFN-γ, and the hyperproliferation of T cells. These events are eventually followed by the deletion of the affected T cell population through apoptosis (see FIG. 1A).

Superantigens are the causative agents in the acute diseases, food poisoning and toxic shock syndrome, and in more chronic conditions, such as inflammatory skin diseases. In addition to the toll on public health, *S. aureus* superantigens also represent a potential biothreat to national security (Schiffenbauer et al., 1993, Proc. Natl. Acad. Sci. USA 90: 8543-8546; Laurence et al., 1992, Nature 358: 255-9; Yarwood et al., 2000, FEMS Microbiol. Lett. 192: 1-7).

Human diseases resulting from *Staphylococcal* and *streptococcal* infection and the resultant release of SAGs into the infected individual are primarily characterized by fever and shock and continue to present a major health problem worldwide. The *S. aureus* enterotoxins (SEA-I) are thought to be the causative agents in 33% of all food poisoning cases (Chesney et al., 1984, A. Rev. Microbiol. 38: 315-338) and are the most frequent cause of hospital-acquired infections (Emori and Gaynes, 1993, Clin. Microbiol. Rev. 6: 428-442). An estimated 1.3 million US patients acquire *S. aureus* infections annually, generally resulting in doubling the length of hospitalization and the associated medical costs.

Toxic Shock Syndrome (TSS), mediated primarily by the *S. aureus* TSST-1 toxin, was recognized as a significant problem in the 1980s when more than a thousand cases of TSS became linked to tampon usage (Davis et al., 1980, New Engl. J. Med. 303: 1429-1435). Presently, potentially life-threatening TSS most frequently occurs when *S. aureus* bacteria infect surgical wounds or injury sites, with up to 6000 cases each year in the US (Schlievert et al., 1988, European Conference on Toxic Shock Syndrome. Intl. Congress and Symposium Series, Vol. 229. Royal Society of Medicine Press, New York; Bohach et al., 1990, Crit. Rev. Microbiol. 17: 251-272). In more chronic conditions, such as inflammatory skin diseases, a growing body of evidence implicates *S. aureus* SAGs in the onset of these diseases by disrupting immune activity through abnormal T cell activation and inflammatory cytokine release.

Some studies have speculated that SAGs promote autoimmune and immunodeficiency diseases such as multiple sclerosis (Schiffenbauer et al., 1993, supra) and HIV infection (Laurence et al., 1992, supra) by continually weakening the normal host immune response, thus allowing the onset of disease to progress more quickly.

The mechanism of *S. aureus* pathogenesis has been attributed to an alternate mode of SAG binding. In contrast to foreign antigens, SAGs bypass the internalization and processing by the antigen presenting cell (APC), and instead bind externally to the DRα1 domain of the MHC class II receptor on APCs and the Vβ domain of the T cell receptor (TCR) on T cells (Jardetzky, et al., 1994, Nature 368: 711-8; Kim et al., 1994, Science 266: 1870-4; Fields et al., 1996, Nature 384: 188-92; Li et al., 1998, Immunity 9: 807-816). The alternate binding of SAG to the MHC class II-TCR complex is followed by two additional signaling events between APCs and T cells, the engagement of co-stimulatory ligands and their cognate receptors, such as the B7 ligand and CD28 (Reiser et al., 1996, N Engl J Med 335: 1369-77), and the involvement of the autocrine and paracrine cytokine network (see FIG. 1A) (Haddad, J., 2002, Biochem. Biophys. Res. Comm. 297: 700-13). SAGs also have the ability to bind to multiple isoforms of TCRVβ. (Choi et al., 1989, Proc Natl Acad Sci U S A 86: 8941-5) and can activate up to 20% of T cells compared to 0.0001% by a conventional antigen, resulting in the activation of a large population of T cells (Sundberg and Mariuzza, 2002, Curr. Opin. Immunol. 14: 36-44). Crystal structures of SAGs (Papageorgiou et al., 1998, J. Mol. Biol. 277: 61-79; Prasad et al., 1997, Protein Sci. 6: 1220-7; Chi et al., 2002) J. Biol. Chem. 277: 22839-46) and their complexes with the MHC class II and T cell receptors have been reported.

SAGs simultaneously bind to the outside surfaces of the HLA-DRα domain of MHC class II and the Vβ domain of the T cell receptors, primarily through contacts with the complementarity-determining regions (CDR) 1 and 2 and the hypervariable region HV4 (Choi et al., 1989, Proc. Natl. Acad. Sci. USA 86: 8941-8945; Kappler et al., 1989, Science 244: 811-813; Fraser, 1989, Nature 339: 221-223). X-ray crystallographic studies have provided a very detailed structural understanding of how the SAGs contact the MHC class II and T cell receptors, leading to a better understanding of the mechanism of SAG stimulation (Jardetzky et al., 1994, Nature 368: 711-718; Kim et al., 1994, Science 266: 1870-1874; Fields et al, 1996, Nature 384: 188-192).

Generally stimulation is achieved by SAG binding to multiple TCRVβ isoforms and activation of larger numbers of T cells than occur during foreign-peptide stimulation. This over-stimulation of the immune system results in massive cytokine release, including IL-2 and IFN-γ from the T cells, and IL-1β and TNF-α from APCs (Langford et al., 1978, Infect. Immun. 22: 62-68; Marrack et al., 1990, J. Exp. Med. 171: 455-464; Miethke et al., 1992, J. Exp. Med. 175: 91-98). The stimulated T cell population initially undergoes cell proliferation; however, in the course of 1-2 weeks, the affected T cells become anergic and are no longer able to respond to foreign and harmful agents. These T cells are eventually deleted from the immune cell repertoire through apoptosis or programmed cell death (Ettinger et al., 1995, J. Immunol. 154: 4302-4308).

Presently, ten *S. aureus* SAGs, SEA,B,C,D,E,F,G,H,I and TSST-1 and seven SAGs in *Streptococcus pyogenes*, SPE-A, SPE-C, SPE-G, SPE-H, SSA, SMEZ1, and SMEZ2 have been identified (Fraser, 2000, supra). Phylogenetic analysis of *Staphylococcal* and *Streptococcal* SAGs indicates a 20%-90% sequence similarity and suggests that all the toxins have evolved from a common ancestral gene. Very small amounts of purified toxin are capable of stimulating significant host effects. Small quantities of toxin (femtogram to picogram) can activate a culture of human peripheral blood lymphocytes and stimulate T cell proliferation of restricted TCRVβ domains (Carlsson and Sjogren, 1985, Cell Immunol. 96: 175-183). Oral injection of several micrograms of toxin is capable of inducing vomiting and diarrhea in humans and primates.

Treatment of SAG-based diseases is primarily limited to supportive therapy once symptoms have manifested. These treatments include antibiotic use, administration of intravenous fluids, and medications to treat low blood pressure and shock. Unfortunately, the heavy usage of antibiotics over the last several decades have led to the emergence of *S. aureus* strains resistant to the two most commonly-used antibiotics, methicillin (Kreiswirth et al., 1993, Science 259: 227-230) and vancomycin (Pearson, 2002, Nature 418: 469). Antibiotic resistance and the relative ineffectiveness of supportive treatments in cases of high load bacterial infections have heightened efforts to develop innovative strategies for combating *Staphylococcal* infections. In addition, given that SAGs are considered to be potential biowarfare select agents according to the CDC and can severely impair the ability of infected soldiers to perform in the battle field, there is a considerable and timely need to develop the next generation of countermeasures (i.e., vaccines and therapeutics) for both treatment of established disease and as a preventive measure against exposure to SAGs.

Toxic Shock Syndrome (TSS) is an acute, life-threatening condition caused by *S. aureus* infection, and is characterized by fever, hypotension, rash, multiorgan dysfunction, and desquamation during the early convalescent period. TSS may be caused by any of the superantigens produced by *S. aureus,* with TSST-1 and enterotoxin B being the first and second most frequently implicated.

Beyond supportive therapy, a number of different therapeutic strategies are being evaluated. Generally, these strategies are aimed at blocking the initial stages of pathogenesis prior to activation of T cell proliferation and cytokine release, and include neutralizing antibodies against *S. aureus* or SAGs, SAG-derived peptides that interfere with immune cell signaling and elicit anti-SAG-antibody production, transcriptional and translational inhibition of SAG genes, receptor-based countermeasures to inhibit SAG binding to immune cells, inhibition of co-stimulatory signals that are required for T cell stimulation, IL-10 cytokine-based approaches, small molecule inhibitors, and anti-cytokine antibodies. For example, one particular approach targets the downstream effects of SAG-induced cytokine release by using anti-cytokine antibodies to TNFα and IFNγ. However, such anti-cytokine strategies may prove ineffective or problematic in view of the massive amounts of different cytokines that are released and the multiple signaling pathways that become activated in response to the SAG induced cytokines (Miethke et al., 1992, supra; Matthys et al., 1995, Infect. Immun. 63:1 158-1164).

It has previously been reported that a DRα1-$(GSTAPPA)_2$-TCRVβ3 chimera inhibited SEB-induced IL-2 cytokine release and T cell proliferation in a mixture of human peripheral mononuclear and dendritic cells (Lehnert et al., 2001, Biochemistry 40: 4222-4228). The object of the present invention is to provide effective therapeutic strategies against *Staphylcoccal* and *Streptococcal* SAGs.

SUMMARY OF THE INVENTION

The invention provides novel therapeutic strategies and compositions useful in the treatment of conditions and syndromes resulting from exposure to bacterial superantigens, including Toxic Shock Syndrome, methods of making the therapeutic compositions, and methods of treating Toxic Shock Syndrome and other conditions and syndromes resulting from exposure to bacterial superantigens.

The therapeutic compositions of the invention comprise genetically engineered bifunctional polypeptides containing a specific T-cell receptor binding domain and a specific MHC class II receptor binding domain, each targeting non-overlapping epitopes on a superantigen molecule against which they are designed. These anti-superantigen "receptor mimetics" or "chimeras" are rationally designed to recreate the modality of superantigen binding directly to both the TCR and the MHC-II receptor, and are capable of acting as decoys for superantigen binding, effectively out-competing the host T-cell and MHC-II receptors, the natural host receptors. Administration of the receptor mimetics to an infected individual will lead to binding of superantigens circulating in the host, preventing them from binding to the host's TCR and MHC-II receptor, as well as competing off SAGs in a binding relationship with either or both the MHC-II receptor and the TCR, thus disabling the trigger which causes illness.

In one aspect, the invention provides an anti-SEC3 chimera comprising an MHC-II receptor binding component and a TCR binding component, each of which binds to a distinct epitope of *Staphylococcus aureus* enterotoxin SEC3, wherein said MHC-II receptor and TCR binding components are physically linked in a manner that permits the chimera to simultaneously bind to said epitopes of *Staphylococcus aureus* enterotoxin SEC3. In one embodiment, the MHC-II receptor binding component is a human MHC-II receptor DRα1 polypeptide and the TCR binding component is a human TCRVβ polypeptide that binds to SEC3.

In another aspect, the invention provides an anti-TSST-1 chimera comprising an MHC-II receptor binding component and a TCR binding component, each of which binds to a distinct epitope of *Staphylococcus aureus* enterotoxin TSST-1, wherein said MHC-II receptor and TCR binding components are physically linked in a manner that permits the chimera to simultaneously bind to said epitopes of *Staphylococcus aureus* enterotoxin TSST-1. In one embodiment, the MHC-II receptor binding component is a human MHC-II receptor DRα1 polypeptide and the TCR binding component is a human TCRVβ polypeptide that binds to TSST-1.

In some embodiments, the MHC-II receptor DRα1 and TCRVβ polypeptides of the chimera may be physically linked by a non-covalent linkage, such as a coiled coil linkage (e.g., c-jun and c-fos). In other embodiments, the MHC-II receptor DRα1 and TCRVβ polypeptides are physically linked by a fused polypeptide linker. In a specific embodiment, the polypeptide linker has the amino acid sequence GSTAPPAG-STAPPA (SEQ ID NO. 5). Polypeptide linkers may also contain an amino acid sequence that permits functional attachment of the linker to a solid phase, such as a HIS tag sequence.

The invention provides the chimeras of the invention formulated in various ways, including without limitation, into multimeric compositions comprising the same or a combination of different chimera. In one embodiment, for example, the multimeric chimera comprises a homogeneous multimer consisting of plurality of monomeric chimera units joined with a physical linker. Such momomeric chimeras may be useful to amplify the concentration of SAG binding elements in therapeutic or biosensor applications of the technology. In another embodiment, the multimeric chimera comprises a heterogeneous multimer, wherein a number of different chimeras are physically linked. Such heterogeneous multimers may effectively target a number of different superantigens, such as a set of superantigens typically expressed by a particular pathogen.

Also provided are lipid compositions comprising a plurality of chimera, wherein the binding components of the chimera are physically linked via coiled coil linkages and the chimera are physically linked to each other via coiled coil linkages, and wherein the chimera are oriented within the lipid and the MHC-II receptor and TCRVβ binding components thereof are oriented on the surface of the lipid The invention also provides isolated nucleic acid molecules encoding the anti-superantigen chimeras of the invention, expression vectors comprising such nucleic acid molecules, and cells comprising such expression vectors. Methods for producing the chimeras of the invention are provided, and generally comprise providing an expression vector which contains an expressible construct encoding an anti-superantigen chimera of the invention, transforming or transfecting a suitable host cell with the expression vector, and expressing the chimera encoded by the expression vector.

The invention also provides a method of treating Toxic Shock Syndrome, comprising administering to an individual exhibiting symptoms of TSS a therapeutic composition comprising a bifunctional polypeptide capable of specifically binding to TSST-1, in a suitable pharmaceutical carrier, at a dose sufficient to competitively inhibit the binding of TSST-1 to the individual's TCR and MHC II receptor.

BRIEF DESCRIPTION OF THE DRAWINGS

FIG. 1C. Schematic representation of a bifunctional chimera of the invention functioning to block superantigen binding to immune cells. The DRα1-linker-TcRVβ chimera sequesters superantigen in the extracellular medium and prevents it from binding APC-T cell FIG. 2. Schematic representation of the DRα1 fragment used in the design of a bifunctional anti-SAG chimera. The fragment adopts a native fold which has been confirmed by circular dichroism and NMR spectroscopy.

FIG. 5. Type-specific inhibition of SAG-induced IL-2 cytokine release by different chimeras. PBMC/DCs were incubated with (A) TSST-1 or (B) SEC3 either alone or in the presence of increasing molar concentrations of SEBc, TSST-1c, or SEC3c for 10 hrs. Supernatants were collected and assayed for IL-2 release by ELISA. Results shown are an average of at least three independent experiments.

FIG. 6. Type-specific inhibition of SAG-induced cell proliferation. PBMCs/DCs were incubated with TSST-1 or SEC3 and PBMCs were incubated with SEB either alone or in the presence of increasing molar concentrations of SEBc, TSST-1c, or SEC3, as noted, for 4 days. Cell proliferation was then assayed using the Vialight assay to measure cellular ATP. Results shown are an average of at least two independent experiments.

FIG. 8. Structural alignment based on SSAP (Orengo and Taylor, 1996, Meth. Enzym. 266: 617-634) of the SAG sequences SEB, SEC3 and TSST-1. Residue numbers are at the top of each line. Secondary structure elements as determined by experimental structures are highlighted for each sequence: β-sheets (light gray) and α-helices (dark gray). Contact residues between the SAG and chimera are marked by the following color scheme: DRα1-cyan, TCRVβ-blue, linker-red, and multiple contacts-purple. Contacts observed in crystal structures or previously reported are underlined using the same color code as the highlights: SEB-DRα1 : SEB-cyan, SEB-TCRVβ:1 SBB-blue, SEC3-TCRVβ:1JCK-blue. SEC3-DRα1 contacts (cyan) were adopted from contacts of the closely homologous SEC2-DRα (Papageorgiou et al., 1996, Protein Sci. 5: 1737-41). TSST-1-DRα (cyan) contacts were identified from the bipartite crystal structure (Kim et al., 1994, supra), and TSST-1-TCRVβ (blue) contacts are from Papageorgiou et al., 1996, supra. The black underlined residues mark contacts of the TSST-1 flexible loop region to DRα1, DRβ, and to the antigenic peptide. Black boxes mark the contact regions that are shown in close up views in FIG. 9.

FIG. 9. Close up view of selected contact regions between the SAGs and their specific chimeras (A) SEB-DRα1, (B) SEC3-linker, and (C) TSST-1-TCRVβ. Contact residues of the SAGs are drawn as van der Waals spheres in different colors per each residue on the solvent accessible surface of the SAGs (grey). The contact residues of the chimeric proteins are displayed as ball and stick models. Secondary structure elements of the SAGs (green) and their interaction partners DRα1 (cyan), TCRVβ (blue) and the linker (red) are imposed as cartoons at the contact interface. Circled residues mark suggested specific mutation sites.

FIG. 11. Comparison of the structure of three superantigens. Ribbon diagram of crystal structures of superantigens (green) SEB (left, PDB identifier: 1SBB: B chain), SEC3 (middle, PDB identifier: 1JCK: B chain), and TSST1 (right, PDB identifier: 2TSS: B chain) with highlighted contact residues to MHC II DRα (cyan) and TcRVβ (blue) from MD simulations. The N and C-terminal residues are marked. The figures were made with SWISS-MODEL (Guez and Peitsch, 1997, supra).

FIG. 14: Comparison of minimized average structures of the superantigen-chimera-complexes. The color code is as follows: superantigen in green, chimera components: DRα in cyan, TcRVβ in blue, and the linker in red. Arrows mark the orientation of the central α-helix in the superantigen and the long α-helix of the DRα component: SEB-chimera complex (left), SEC3-chimera complex (middle) and TSST-1-chimera complex (right).

DETAILED DESCRIPTION OF THE INVENTION

Figure 1A:
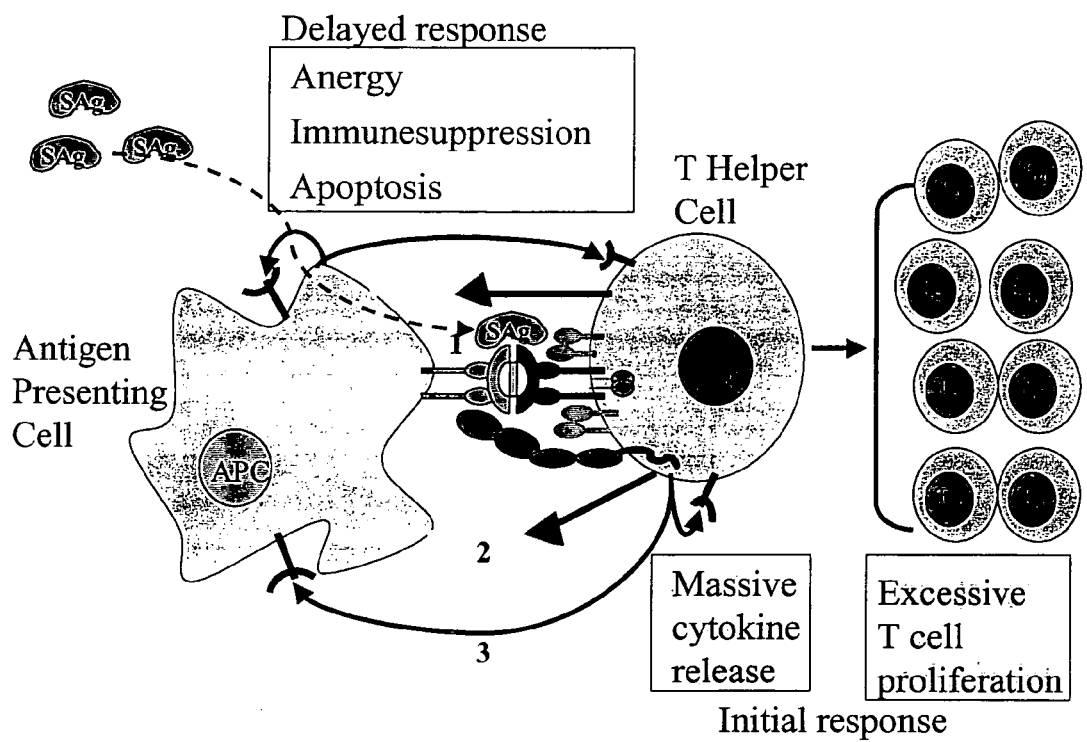
FIG. 1A. Schematic representation of superantigen induction. Superantigen induces three signals to the APC:T cell system: 1) binding to the MHC Class II/TcR followed by CD3, 2), paring of co-stimulatory molecules on APC and T cells, and 3) autocrine and paracrine cytokine network. Combination of these signals produces massive cytokine release (4-12 hours), T cell proliferation (2-3 days), and anergy, apoptosis, immune suppression by 7-14 days.
Figure 1B:
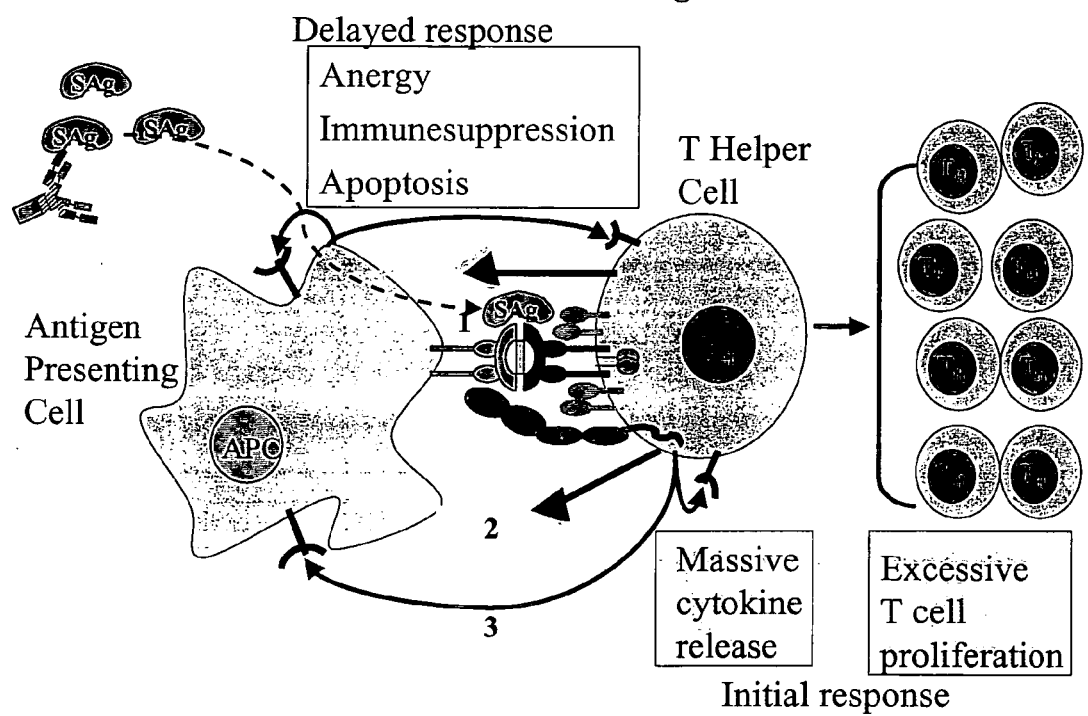
FIG. 1B. Schematic representation of antibody failure to bind SAG at both cell binding sites.

Definitions:

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

The terms "(superantigen) TCR binding domain" and "(superantigen) MHC-II receptor binding domain" refer to polypeptides which bind to a superantigen molecule, and include without limitation, respectively, TCRVβ isoform polypeptides or fragments thereof containing a TCRVβ superantigen binding site, as well as variants thereof which retain the ability to bind to target superantigen(s); and MHC-II receptor α and β chain polypeptides or fragments thereof containing a MHC-II receptor α or β chain superantigen binding site, as well as variants thereof which retain the ability to bind to target superantigen(s). When used in relation to the chimeras of the invention, the terms "TCR binding component" and "MHC-II receptor binding component" refer to polypeptides which comprise a superantigen TCR binding domain or a superantigen MHC-II receptor binding domain, respectively. The terms "MHC-II receptor DRα1 polypeptide", "TCRVβ polypeptide", and the like, are meant to include not only the wild type polypeptides, but also fragments and variants thereof which retain the ability to bind to target superantigen(s).

The terms "chimera" and "anti-SAG chimera" refer to heterologous polypeptides comprising a TCR binding component and a MHC-II receptor binding component which are physically linked.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

As used herein, “linker” refers to a molecule or group of molecules that connects two molecules, such as TCR and MHC-II receptor binding domains and serves to place the two molecules in a preferred configuration.

A “Coiled-coil” as used herein refers to an α-helical oligomerization domain found in a variety of proteins. Proteins with heterologous domains joined by coiled coils are described in U.S. Pat. Nos. 5,716,805 and 5,837,816. Structural features of coiled-coils are described in Litowski and Hodges, 2002, J. Biol. Chem. 277:37272-27279; Lupas, 1996, TIBS 21:375-382; Kohn and Hodges, 1998, TIBTECH 16: 379-389; and Müller et al., 2000, Methods Enzymol. 328: 261-282. Coiled-coils generally comprise two to five α-helices (see, e.g., Litowski and Hodges, 2002, supra). The α-helices may be the same or difference and may be parallel or anti-parallel. Typically, coiled-coils comprise an amino acid heptad repeat: “abcdefg.”

“Fused” refers to linkage by covalent bonding.

A “fusion protein” refers to a chimeric molecule formed by the joining of two or more polypeptides through a bond formed one polypeptide and another polypeptide. Fusion proteins may also contain a linker polypeptide in between the constituent polypeptides of the fusion protein. The term “fusion construct” or “fusion protein construct” is generally meant to refer to a polynucleotide encoding a fusion protein.

The term “heterologous” when used with reference to a nucleic acid or polypeptide indicates that the nucleic acid or polypeptide comprises two or more subsequences that are not found in the same relationship to each other in nature. For instance, a nucleic acid is typically recombinantly produced, having two or more sequences from unrelated genes arranged to make a new functional nucleic acid. Similarly, a heterologous protein indicates that the protein comprises two or more subsequences that are not found in the same relationship to each other in nature (e.g., a chimeric protein).

The term “isolated,” when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term “purified” denotes that a nucleic acid or protein gives rise to essentially one band in an electrophoretic gel. Particularly, it means that the nucleic acid or protein is at least 85% pure, more preferably at least 95% pure, and most preferably at least 99% pure.

“Nucleic acid” refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms “polypeptide,” “peptide” and “protein” are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term “amino acid” refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms “peptidomimetic” and “mimetic” refer to a synthetic chemical compound that has substantially the same structural and functional characteristics of the polypeptides of the invention. Peptide analogs are commonly used in the pharmaceutical industry as non-peptide drugs with properties analogous to those of the template peptide. These types of non-peptide compound are termed “peptide mimetics” or “peptidomimetics” (Fauchere, J. *Adv. Drug Res.* 15:29 (1986); Veber and Freidinger *TINS* p. 392 (1985); and Evans et al. *J. Med. Chem.* 30:1229 (1987)). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of, e.g., —CH2NH—, —CH2S—, —CH2-CH2-, —CH=CH— (cis and trans), —COCH2-, —CH(OH)CH2-, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Such conservatively modified variants are in addition to and do not exclude polymorphic variants, interspecies homologs, and alleles of the invention.

For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 22 amino acids or nucleotides in length, or more preferably over a region that is 30, 40, or 50-100 amino acids or nucleotides in length.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, 95%, 98% or 99% similar over a specified region or, when not specified, over the entire sequence), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 100, 200, 300, 400, 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)). Typically, the Smith & Waterman alignment-with the default parameters are used for the purposes of this invention Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. The default parameters of BLAST are also often employed to determined percent identity or percent similarity.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under-expressed or not expressed at all.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

Designing Superantigen Therapeutic Chimeras:

The therapeutic chimeric proteins of the invention generally share a common structural organization, comprising the unit A-X-B, where component A represents an MHC-II receptor α- or β-chain polypeptide or variant thereof, component X represents a physical linker, and component B represents a TCR Vβ polypeptide or variant thereof, wherein the A and B components each bind to non-overlapping, or "distinct" epitopes on a target SAG or SAGs. A schematic illustration of a chimera of the invention functioning to block SAG binding to immune cells is shown in FIG. 1C.

The components A and B may correspond to the wild type polypeptides or to variants thereof. Typically, for human therapeutic applications, components A and B will correspond to human polypeptides or variants thereof, such as variants containing one or more amino acid mutations which confer enhanced binding affinity in relation to the wild type sequences. Component X is a physical linker, which in some embodiments is a flexible polypeptide linker fused to the polypeptide components A and B. In such embodiments, a nucleic acid molecule fusion construct encoding all three components in frame may be constructed and used to generate a fusion polypeptide. Other physical linkers known in the art may be used to join components A and B, as discussed infra.

The majority of known SAGs bind to the DRα1-chain of the MHC-II receptor molecule and to one or more isoforms of the TCR Vβ-chain. These SAGs include the S. aureus superantigens SEB, SEC1, SEC2, SEC3, SED, SEE, and TSST, and the S. pyogenes superantigen SPE-A. However, several bacterial SAGs have been shown to bind to the β-chain of the MHC-II receptor molecule, in some cases demonstrating no binding to the α-chain (S. pyogenes SPE-C, SPE-G, SPE-H, SMEZ, and SMEZ-2), and in at least two cases, to both the α- and β-chains of the MCH-II molecule (S. aureus SEA and SEE). Accordingly, in the design of a chimera of the invention, the particular binding mechanism(s) of the target SAG(s) should be taken into consideration.

Component A: MHC-II Receptor Binding Component:

A variety of SAG-MHC-II receptor binding mechanisms have been elucidated using, inter alia, available crystal structures for a number of bacterial SAGs.

Despite a highly conserved structural fold common to all known bacterial superantigens, individual SAGs have evolved at least three substantially different mechanisms of binding to the MHC-II receptor molecule. The binding mechanism used by a particular SAGs will influence the design of a therapeutic chimera targeting that SAG. For example, utilizing an MHC-II receptor α1-chain for component A of the chimera will be effective for binding some SAGs but not others (see below).

The crystal structure of S. aureus SEB complexed with HLA-DR1, for example, reveals that it resembles a wedge which fits between the TCR and MHC-II receptor molecules, both of which in turn are in contact (Jardetsky et al., 1994, Nature 368: 711-718). In contrast, the crystal structure of TSST complexed with HLA-DR1 shows that TSST binds to the same region of the DR1α domain that SEB binds, but unlike SEB covers most of the top region of the MHC-II receptor molecule, preventing contact between MHC-II receptor and the TCR (Kim et al., 1994, Science: 266: 1870-1874). Based on these observations, it has been suggested that TSST activation of T-cells may depend only on the affinity of TSST binding to the TCR, without any mediation resulting from TCR-MHC-II contacts (Fraser et al., 2000, supra). Thus, in constructing a therapeutic chimera against TSST or SEB, component A of the chimera may comprise an MHC-II receptor DRα1 -chain or a variant thereof.

Another binding mechanism is utilized by a subset of bacterial SAGs that contain a high affinity MHC-II receptor E-chain zinc-binding site as well as a low affinity MHC-II receptor α-chain binding site, and include SEA, SEE, SED, SSA, and SMEZ (Fraser et al., supra). The interaction between SEA and the β-chain binding site is predicted to be 100 times stronger than the interaction between SEA and the low affinity α-chain binding site. These superantigens are therefore capable of binding to both sides of the MHC-II receptor molecule, resulting in cross-linking of the MHC-II receptor on the surface of antigen presenting cells, which in turn triggers TNF-α and IL-1 expression in the antigen presenting cell. Accordingly, in the design of therapeutic chimeras targeting these SAGs, component A is preferably an MHC-II receptor P-chain polypeptide or a variant thereof which comprises this high affinity zinc-mediated binding site. Alternatively, a DRα chain binding component may be used where the binding of the DRα to the SAG prevents SAG dimerization.

Yet another and novel binding mechanism is used by the Streptococcal superantigens SPE-C, SMEZ-2, SPE-G and SPE-H. These Streptococcal SAGs bind only to a zinc-mediated β-chain binding site (Rousesel et al., 1997, Nat. Struct. Biol. 4: 635-643; Li et al., 1997, J. Exp. Med. 186: 375-383; Proft et al., 1999, J. Exp. Med. 189: 89-102). In this mechanism, the zinc atom bridges the SAG to the MHC-II receptor, thereby limiting the extent to which the SAG must make contacts with surrounding polymorphic residues, thus minimizing the contacts between residues of the SAG and residues of the MHC-II receptor. Therefore, in the design of therapeutic chimeras against SAGs utilizing this binding mechanism, component A of the chimera may comprises the MHC-II receptor β-chain, or potentially a polypeptide comprising the zinc-mediated β-chain binding site, or variants thereof. Because the zinc-mediated nature of the SAG-MHC-II interaction limits the SAG contacts with MHC-II residues, it may be possible to design polypeptides that contain a zinc-mediated binding site other than those corresponding to the native MHC-II receptor E-chain binding site.

Where the chimera is designed to contain an MHC-II receptor α chain binding component, it is not necessary that the full length native polypeptide be used. Structural analyses of numerous MHC-II receptor α chain sequences revealed that a DRα1 fragment of about 80-90 residues spanning the N-terminal α1 fragment can retain the native fold, consisting of four beta-strands and a long alpha-helix. The residues on two of the loops connecting the beta strands and the alpha-helix make direct contact with the superantigen molecule (see FIG. 2).

In a particular embodiment, an 84 amino acid polypeptide fragment of the DRα1 chain of the MHC-II receptor is used as component A in the chimera design. This sequence was selected from a number of candidate α1 chains as most likely to show stable folding and favorable binding to SAG, and has the following amino acid sequence:

IKEEHVIIQAEFYLNPDQSGEFMFDFDGDEIFHVDM (SEQ ID NO: 1)

AKKETVWRLEEFGRFASFEAQGALANIAVDKANLEI

MTKRSNYTPITN

Variants of this sequence may provide stronger binding functionality. Based on molecular modeling studies (see Examples 2 and 3, infra), a number of amino acid mutations are predicted to increase the binding affinity of the chimera for superantigen target.

Table I, infra, shows the known MHC-II receptor binding specificities for a group of known superantigens. This information provides initial guidance in the design of receptor mimetics against particular SAGs.

TABLE I

MCH-II AND TCR Vβ BINDING SPECIFICITIES OF SAGs

| SAG | MHC-II BINDING α/β CHAIN | HUMAN TCR Vβ SPECIFICITY |
|---|---|---|
| *S. aureus* | | |
| SEA | +/+ | 1.1, 5.3, 6.3, 6.4, 6.9, 7.3, 7.4, 9.1, 23.1 |
| SEB | +/− | 1.1, 3.2, 6.4, 15.1 |
| SEC1 | +/− | 3.2, 6.4, 6.9, 15.1 |
| SEC2 | +/− | 12, 13, 14, 15, 17, 20 |
| SEC3 | +/− | 5.1 |
| SED | +/? | 1.1, 5.3, 6.9, 7.4, 8.1, 12.1 |
| SEE | +/+ | 5.1, 6.3, 6.4, 6.9, 8.1 |
| SEG | ?/? | ? |
| SEH | ?/? | ? |
| SEI | ?/? | ? |
| SEJ | ?/? | ? |
| TSST | +/− | 2.1, 8.1 |
| *S. pyogenes* | | |
| SPE-A | +/− | 2.1, 12.2, 14.1, 15.1 |
| SPE-C | −/+ | 2.1, 3.2, 12.5, 15.1 |
| SPE-G | ?/+ | 2.1, 4.1, 6.9, 9.1, 12.3 |
| SPE-H | ?/+ | 2.1, 7.3, 9.1, 23.1 |
| SSA | ?/? | 1, 3, 15, 17, 19 |
| SMEZ | ?/+ | 2.1, 4.1, 7.3, 8.1 |
| SMEZ-2 | ?/+ | 4.1, 8.1 |
| *C. perfringens* | | |
| CPET | ?/? | 6, 7, 8, 9, 22 |

Component B: TCR Binding Component:

SAGs bind to specific isoforms of the Vβ-chain of the TCR, and each SAG demonstrates a different TCR Vβ specificity profile (see, e.g., Fraser et al., 2000, Molecular Medicine Today 6: 125-132). Many of the known SAGs are capable of binding to several different isoforms, thereby activating T-cells bearing any of the several TCRVβs. For example, *S. aureus* SEA binds to Vβ isoforms 1.1, 5.3, 6.3, 6.4, 6.9, 7.3, 7.4, 9.1 and 23.1. Based on the information obtained to date, other SAGs show specificity for one isoform (e.g., SEC3, which only binds Vβ 5.1) or two isoforms (e.g., TSST, which binds Vβ 2.1 and 8.1). Therefore, in the design of chimeras specific for many target SAGs, it is possible to utilize a number of different Vβ domains in the chimera design. Preferred chimeras will preferably incorporate a TCRVβ isoform showing relatively high binding affinity. In some embodiments, this may be the isoform for which the SAG has the highest affinity.

*Staphylococcal* enterotoxins (SE) (i.e., SEG, SEH, SEI, & SEJ) are found predominantly in food-borne staphylococci (Rosec & Gigaud, 2002, Intl. Jl. Food Microbiol, 77:61-70). TCRVβ specificities of these superantigens are yet to be accurately determined although SEH seems to show cross-reactivity with some members of the SEA-specific TCRVβ repertoire (Hakansson et al., 2000, JMB, 302:527-537). A high throughput RT PCR method (Cottrez et al., 1994, J. Immunol. Methods, 172:85-94) using a human cell model may be used to provide the TCRVβ specificity of these non-classical SEs.

Figure 3:
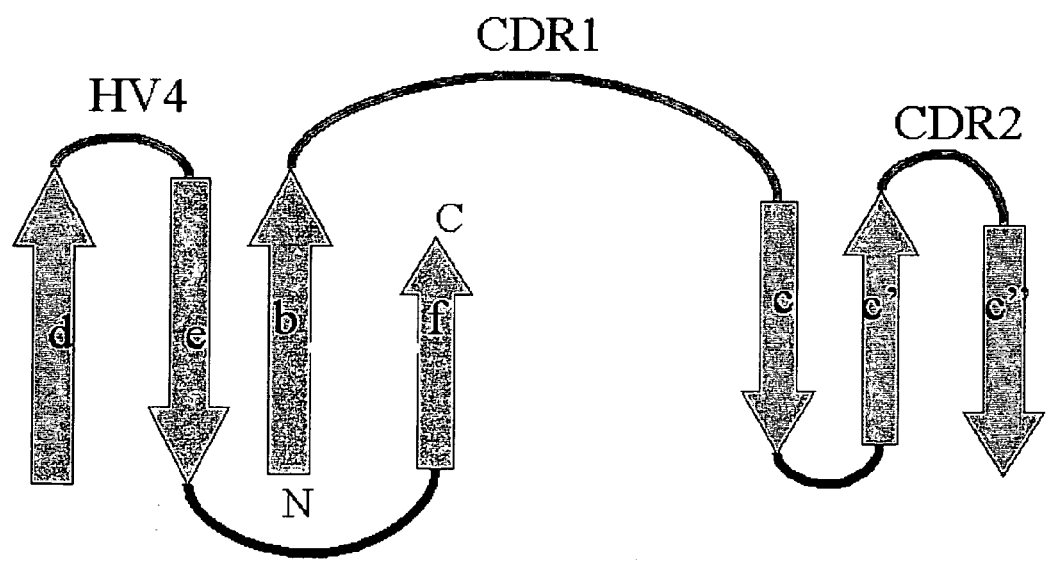
FIG. 3. Schematic representation of a TCRVβ fragment used in the design of a bifunctional anti-SAG chimera.

Table I, supra, shows the known TCRVβ binding specificities for a group of known superantigens. This information provides initial guidance in the design of receptor mimetics against particular SAGs. Structural analyses of all TCRVβ isoforms listed in Table I revealed that a fragment of about 65-75 amino acid residues spanning the Vβ domain of the TCR can retain the native fold, consisting of seven beta-strands. A schematic representation of the TCRVβ fragment used in the design of the receptor mimetics exemplified in the examples, infra, is shown in FIG. 3. Note that the cysteines from the "b" and "f" strands form a disulfide bridge which helps maintain the native fold. The residues on the CDR1, CDR2, and HV4 loops make direct contact with the superantigen (FIG. 3).

Various methods for determining or predicting which of several specific TCRVβ isoforms are likely to show the highest degree of affinity for a particular SAG within a chimera of the invention may be employed, including, for example, comparing SAG-TCRVβ isoform binding affinities, comparing T-cell activation profiles, and directly measuring SAG binding to a set of chimeras containing different TCRVβ components using standard methods and assays. In addition, molecular modeling may be employed in order to help identify the tightest TCRVβ binder for a given superantigen. For example, an ensemble of low energy structures for a set of SAG-chimera complexes, each of which differs only in its TCRVβ component, may be modeled as described in Example 3, infra. Identification of the best TCRVβ component for designing a therapeutically efficacious chimera for a particular SAG is achieved by comparing the average energies of the different complexes. Biological assays widely utilized in the art may also be employed in evaluating and comparing candidate chimeras containing different TCRVβs, including without limitation IL-2 release from T-cells in vitro, T cell proliferation.

Similarly, such modeling methods may be used to select the TCRVβ isoform most likely to bind multiple SAGs with the highest average affinity for the target group of SAGs. In this regard, several of the SAG produced by *S. aureus* recognize common TCRVβ isoforms. For example, the TCRVβ specificity profiles of SEA, SEB, SEC1, and SEE all include the TCRVβ 6.4 isoform.

Similarly, the TCRVβ specificity profiles of the *S. pyogenes* superantigens SPE-A, SPE-C, SPE-G, SPE-H and SMEZ all include the TCRVβ 2.1 isoform, as does the profile of *S. aureus* TSST. Therefore, it possible to take advantage of these common specificities, and utilize a TCRVβ isoform which can bind to multiple SAGs in the design of an effective therapeutic chimera, in order to target multiple SAGs produced by the same pathogen, or indeed multiple pathogens. In one embodiment, for example, a therapeutic chimera targeting multiple SAGs produced by *S. aureus* utilizes a TCRVβ 6.4 isoform or a variant thereof as component B.

In one embodiment, a chimera designed against *S. aureus* TSST-1 utilizes a human TCRVβ 2 isoform as component B. This TCRVβ component has the following amino acid sequence, and was cloned using a series of PCR amplification cloning steps outlined in Example 1, infra:

ASVSQHPSRVKIECRSLDFQATTMFWYRQFPKQSLM (SEQ ID NO: 2)

LMATSNEGSKATYEQGVEKDKFLINHASLTLVTSAH

PEDSSFYICSA

In another embodiment, a chimera designed against *S. aureus* SEB utilizes a human TCRVβ3 isoform, with the last hairpin loop deleted (since the CDR3 loop does not show any contact with SEB in the SEB-TCR complex) as component B. This TCRVβ component has the following amino acid sequence, and was prepared as described (Lehnert et al., 2001, supra):

VFLECVQDNDHENMFWYRQDPGLGLRLIYFSYDVKN (SEQ ID NO: 3)

KEKGDIPEGYSVSREKKERFSLILESASTNQTSMYL

CA

In another embodiment, a chimera designed against *S. aureus* SEC3 utilizes a truncated version of a mouse TCRVβ8.2 isoform mutant, mL2.1/A52V, that had been isolated by screening a mutagenized library of TCRVβ8.2 variants using yeast display and flow cytometry sorting (Kieke et al., 2001, J. Mol. Biol. 307: 1305-1315). This TCRVβ8.2 variant shows a 1000 fold increase in binding affinity to SEC3 (Kieke et al., supra) and was incorporated into an anti-SEC3 chimera as a truncated form, containing 7 of the reported 9 mutations, since the remaining 2 mutations lay outside of the consensus TCRVβ domain utilized in the construction of this and an anti-TSST-1 chimera (see Example 1, infra). The amino acid sequence of the truncated TCRVβ8.2 variant is as follows:

ASVTLSCNQTNNHNNMYWYRQDTGHGLRLIHYSYGV (SEQ ID NO: 4)

NTEKGDIPDGYEASRPSHENFSLILVSATPSQSSVY

FCA

Using various molecular evolution and mutation techniques, the effective therapeutic range of a chimera may be expanded to capture additional SAGs produced by the same pathogen or by heterologous pathogens. Such methods may also be employed to improve folding and solubility characteristics of the chimera. For example, the methods described in co-pending, co-owned U.S. patent application Ser. No. 10/423,463, filed Apr. 24, 2003, may be employed for the directed evolution of chimera or the individual binding components thereof.

Component X: Physical Linker Component

The therapeutic chimeras of the invention act by mimicking the MHC-II and TCR binding sites utilized by SAGs in a conformationally stable chimera composition. In order to achieve this most effectively, the MHC-II receptor and TCR binding site components of the chimera are physically linked in order to bring both binding components within a physical proximity that will permit and facilitate synergistic binding to both sites by the target SAG, while at the same time providing the flexibility necessary to enable both to bind to the target. The bi-specific nature of chimera: SAG binding generates a complex which generally is expected to yield a higher binding affinity, in comparison to the SAG binding affinities with the binding components individually, due to the synergy of the two binding interactions possible with the chimera. Moreover, a binding event between one of the chimera binding components and the target SAG will in turn result in increasing the local concentration of the other binding component, thus facilitating its binding to the target SAG as well.

In some embodiments, the physical linker is designed to remain flexible, in order to permit the binding components to move freely and adopt conformations necessary to simultaneously bind the superantigen target. For example, a polypeptide linker may be fused to both binding components A and B.

In a specific embodiment utilized in exemplified chimeras against various *S. aureus* SAGs, the polypeptide GSTAPPAGSTAPPA (SEQ ID NO: 5), also designated (GSTAPPA)$_2$ (SEQ ID NO: 5), is used as a fused linker (see Example 1, infra). This sequence is part of a repeat sequence within the human tandem repeat protein mucin. Previous studies on human mucin had shown that the (GSTAPPA)$_2$ (SEQ ID NO: 5) sequence was flexible, adaptive, and potentially non-antigenic (Fontenot et al., 1995, Proc. Natl. Acad. Sci USA 92:315-319).

Other amino acid sequences which provide flexibility and physical orientation enabling binding between the chimera components and the target SAG(s) may be evaluated as linkers. Preferably, linker polypeptides are devoid of sequences that give rise to stable inter-linker associations and secondary structures may be employed. Typically, such linkers will comprise near-neutral amino acids (i.e., serine, alanine, threonine, valine and/or glycine residues), and will be attached at one end to the N-terminus of one of the binding components (A or B) and at the other end to the C-terminus of the other binding component (B or A). The length and amino acid sequence of such polypeptide linkers should be designed to be non-perturbing to the native folding of the binding domains A and B, while also permitting the simultaneous binding of the binding domains to the target SAG.

In the design of any physical linker used to join the MHC-II receptor and TCRVβ components of the chimera, both the distance between the components and the relative contact interface axis should be taken into consideration. Based upon analysis of the three particular anti-SAG chimeras described in the Examples herein, the center of mass to center of mass distance between the two SAG binding components should be about 20-30 Angstroms, and the principal axis of the contact interface should place the two binding components at an angle of between about 45 and 75 degrees within the plane of the principal axis.

Amino acid sequences which may be usefully employed as linkers include those disclosed in Maratea et al. (1985) Gene 40:39-46; Murphy et al. (1986) Proc. Natl. Acad. Sci. USA 83:8258-8262; U.S. Pat. Nos. 4,935,233 and 4,751,180. Additionally, polypeptide linkers may be functionalized with a domain that provides a binding domain, an attachment sequence, etc. (see below).

Preferably, the linker polypeptide should be non-perturbing to the conformational stability and solubility of the chimera binding components A and B. Solubility characteristics of such linkers may be enhanced using, for example, the introduction of charged residues (see, e.g., U.S. Pat. No. 5,990,275). Linkers should also be designed to reduce the potential for linker-mediated aggregation. To reduce linker susceptibility to proteolytic degradation, candidate linkers may be evaluated for stability in the presence of proteolytic enzymes that may be present in the applications in which the switch will be used. One method for reducing the susceptibility to proteolytic degradation involves the incorporation of a Proline residue, preferably adjacent to a charged amino acid (U.S. Pat. No. 5,990,275).

Alternatively, components A and B may be physically linked by a non covalent linkage, such as coiled coil linkage (such as E and K coils, jun and fos coils, A and B coils), natural heterodimeric interacting proteins (such as immunoglobulin CH1 and CL), proteins mutated to be heterodimeric, such as variants of CH3 containing "knobs and holes" (Ridgeway et al., 1996, Protein Engineering 9: 617), or other physical linkages.

In one such embodiment, the physical linkage between the two binding components of the chimera may be achieved through the use of coiled-coils. A number of such coiled-coil binding pairs are well known and may be employed. Coiled-coils generally comprise two to five α-helices (see, e.g., Litowski and Hodges, 2002, supra). The α-helices may be the same or different and may be parallel or anti-parallel. Typically, coiled-coils comprise an amino acid heptad repeat: "abcdefg." Side chains from amino acids a and d pack against each other to form a continuous hydrophobic core along the length of the α-helices. The side chains of amino acids e and g are along the side of the hydrophobic cored. Amino acids e and g are typically charged residues that participate in electrostatic interactions which specify homo- and hetero-association between coils. The exposed amino acids b, c, e, f, and g affect the α-helical propensities of the coil.

Amino acids a and d are generally hydrophobic residues that form the hydrophobic core of the α-helices, for example, valine, leucine, isoleucine, methionine, tyrosine, tryptophan, or phenylalanine. Serine can also be used to form 'serine zippers' (Adamian & Liang, *Proteins* 47:209-218, 2002). Amino acids e and g are typically charged residues and are occupied by glutamic acid in the E coils and lysine in the K coils.

Exemplary coiled-coils include E coils and K coils associated 1:1 to form a heterodimer, A coils and B coils associated 1:1 to form a heterodimer, and other leucine zippers. E coils and. K coils are described in detail in Litowski and Hodges, supra. Preferred E coils generally comprise multimers of the sequence: VSALEKE (SEQ ID NO: 23). Preferred K coils generally comprise multimers of the Sequence: VSALKEK (SEQ ID NO: 24). The valine residues can be substituted by serine (Litowski and Hodges, supra). Preferred A coils generally comprise the sequence:

VAQLEEKVKTLRAQNYELKSRVQRLREQVAQL     (SEQ ID NO: 6)

Preferred B coils generally comprise the sequence:

VDELQAEVDQLQDENYALKTKVAQLRKKVEKL     (SEQ ID NO: 7)

Typically, the E and K coils or A and B coils are at least 14 amino acids in length, even more typically at least 21 amino acids in length. Often the E and K coils or A and B coils are 35 (E/K) or 32 (A/B) amino acids in length, i.e., about 5 heptad repeats. Generally, 35 amino acids is the length used. The longer the coil the greater the expected affinity.

Those of skill in the art will understand that multiple amino acid substitutions may be made that do not affect the stability or α-helical propensities of the coiled coils. Such mutations may be identified either by mutation and selection experiments, or by rational design methods, both of which are described, by way of example, in Arndt et al., (Structure (Camb) 2002 September;10(9):1235). In vivo mutation and selection experiments occasionally identify unexpected residues which improve the function of the coils, and in general have identified better coils than those designed rationally, although the nature of the selection experiment will determine the nature of the coils selected. If there is no counter-selection for homodimerization between the coils, the affinity for such homodimers may also increase during the selective process. Likewise, multiple amino acid substitutions may be made to enhance the stability or α-helical propensities of the coiled coils. For example, the amino acid isoleucine may be substituted into the a position of an E or K coil to increase the hydrophobicity of the coil, and the amino acid alanine may be substituted into the b position of an E or K coil to increased the α-helical propensities of the coiled coils (see, e.g., Litowski and Hodges, 2002).

More specifically, one member of a coiled coil binding pair is attached to the N or C terminus of one binding component, and the second member of a coiled coil binding pair is attached to the N or C terminus of the other binding component.

The interaction between the two coiled coils will bring binding components A and B together. Typically, the members of a coiled-coil binding pair will be placed at the ends of a polypeptide linker used to attach the coiled-coil members to each of the binding components. The length of such polypeptide linkers may be varied to achieve the desired distance between the binding components.

A related embodiment adds disulfide linkage functionality to the coiled-coil binding pairs. In this way, covalent bonds may be formed between coiled-coils after their interaction, resulting in a stabilized coiled-coil linkage with a reduced capacity to disassociate. Such functionality may be achieved by the addition of cysteine residues placed, for example, at either the N or C terminus of the coiled-coil binding members, or within a polypeptide linker fusing the binding components to the coil domains.

In another embodiment, interacting proteins or interacting domains may be attached to the binding components of the chimera in order to provide a physical linkage. For example, the CH1 and CL antibody domains, or variants of CH3 domains which specifically heterodimerize may also be used (e.g., Ridgway et al., 1996, Protein Eng. 9: 617-621; Atwell et al., 1997, J. Mol. Biol. 270: 26-35). As with the use of coiled-coils, linkers that act as spacers are typically employed between the interacting domains and the binding components.

For some embodiments, it may be desirable to functionalize the linker in order to provide, for example, a means of attaching the chimera to a solid phase. Where polypeptide linkages are utilized, the linker may be designed to contain an amino acid sequence that permits functional attachment to a solid phase (e.g., a HIS tag sequence). The use of such functional tags may also facilitate purification of recombinantly produced chimera (see, for example, the use of a HIS tag in Lehnert et al., 2001, supra). In one embodiment, an N-terminal HIS tag is incorporated into the chimera.

In one embodiment, where X is a flexible polypeptide linker, the linker also contains a sequence of amino acids further enabling the linker to be bound to the substrate (an "anchoring sequence"). The location of such anchoring sequences within the linker should be sufficiently distanced from each of the binding components of the chimera so as not to interfere with SAG binding. Examples of such anchoring sequences include, without limitation, HIS tags (where, e.g., the substrate is functionalized with a metal chelate or cobalt, etc.), the incorporation of cysteine residues (mediating disulfide bridging chemistry), and the use of a biotinylated linker in combination with a substrate functionalized with avidin.

In a specific embodiment, a therapeutic chimera of the invention is bound to cobalt functionalized beads or another solid substrate via a HIS element incorporated into a flexible polypeptide linker used to join the binding components of the chimera or fused to the N-terminus of the construct. More particularly, the binding components are linked to each other with a polypeptide linker containing an intermediate HIS element, thereby permitting the chimera to be bound to a cobalt containing substrate via the linker (e.g., cobalt beads).

A variety of substrate materials are available, including a number of polymer hydrogel materials which are particularly suited to water soluble biomolecules. Hydrogel microbeads may also be used to bind the therapeutic chimeras of the invention, arrayed in a column or similar vessel, and used to capture target superantigen from samples delivered into or through the column, capillary or similar vessel. Column type arrays may provide certain advantages, such as the ability to pass biological fluids through the column on a continuous basis. In one application, a patient's blood is passed through the bead-bound chimeras, in order to permit the chimeras to bind and capture superantigen, thereby eliminating the superantigen molecules from the patient's blood supply. In another application, blood transfusion procedures may incorporate the use of such SAG-capture vessels as a means of purifying the transfusion supply before it enters the recipient's vasculature.

The selection and optimization of an appropriate linker may be conducted empirically. For example, a number of different polypeptide linkers may be joined to the binding components of a chimera and screened for binding and affinity in the presence of target SAG. Alternatively, molecular modeling may be employed to select and/or optimize linkers (e.g., evaluate the impact of mutations within a polypeptide linker within a chimera-SAG complex).

Exemplary Anti-SAG Chimera:

The construction and evaluation of a series of anti-*Streptococcal* SAG chimera is described in detail in the Examples sections, infra. The amino acid sequences of three exemplary chimera (against *S. aureus* SEB, SEC3 and TSST-1) are presented below. All three of these chimeras are constructed as fusion proteins consisting of an MHC-II receptor binding component, a polypeptide linker, and a TCRVβ binding component.

```
Anti-SEB chimera amino acid
sequence:
IKEEHVIIQAEFYLNPDQSGEFMFDFDGDEIFHV   (SEQ ID NO: 8)

DMAKKETVWRLEEFGRFASFEAQGALANIAVDKA

NLEIMTKRSNYIPITNGSTAPPAGSTAPPAVFLE

CVQDNDHENMFWYRQDPGLGLRLIYFSYDVKNKE

KGDIPEGYSVSREKKERFSLILESASTNQTSMYL

CA

Anti-SEC3 chimera amino acid
sequence:
IKEEHVIIQAEFYLNPDQSGEFMFDFDGDEIFHV   (SEQ ID NO: 9)

DMAKKETVWRLEEFGRFASFEAQGALANIAVDKA

NLEIMTKRSNYTPITNGSTAPPAGSTAPPAASVT

LSCNQTNNHNNMYWYRQDTGHGLRLIHYSYGVNT

EKGDIPDGYEASRPSHENFSLILVSATPSQSSVY

FCA

Anti-TSST-1 chimera amino acid
sequence:
IKEEHVIIQAEFYLNPDQSGEFMFDFDGDEIFHV   (SEQ ID NO: 10)

DMAKKETVWRLEEFGRFASFEAQGALANIAVDKA

NLEIMTKRSNYTPITNGSTAPPAGSTAPPAASVS

QHPSRVKIECRSLDFQATTMFWYRQFPKQSLMLM

ATSNEGSKATYEQGVEKDKFLINHASLTLVTSAH

PEDSSFYICSA
```

Monomeric and Multimeric Chimeras:

The therapeutic chimeras of the invention may be formulated as monomeric or multimeric pharmaceutical compositions. Combinations of monomeric chimeras may also be formulated for therapeutic administration.

Multimeric chimeras may be formulated in a number of ways. In one embodiment, for example, the multimeric chimera comprises a homogeneous multimer consisting of plurality of monomeric chimera units joined with a physical linker. Such momomeric chimeras may be useful to amplify the concentration of SAG binding elements in therapeutic or biosensor applications of the technology. In another embodiment, the multimeric chimera comprises a heterogeneous multimer, wherein a number of different chimeras are physically linked. Such heterogeneous multimers may effectively target a number of different superantigens, such as a set of superantigens typically expressed by a particular pathogen.

Various methods known in the art may be used to construct multimeric chimeras. In one embodiment, a multimerization domain capable of binding a plurality of monomeric chimeras is used to generate a multimeric chimera composition. Means for providing a binding site on the momomeric chimera, which site has affinity for a complementary site on the multimerization domain, may include polypeptide binding sites engineered into one or more of the elements of the monomeric chimera, e.g., at one of the termini of a fusion chimera, within the linker structure, or within one of the SAG binding components. Methods for designing multifunctional polypeptides using coiled-coil interactions and multimerization domains are described in co-owned U.S. application Ser. No. 10/670,167.

Multi-Specific Anti-SAG Chimeras:

Another aspect relates to chimeras designed to have broad SAG binding specificity. In one embodiment, such cross-reactive chimeras may be designed to incorporate a TCRVβ component that naturally binds several superantigens, or that has been genetically engineered or evolved to bind to several superantigens. In a specific embodiment, the TCRVβ 1.1 or 6.4 isoform is used as component B. This isoform shows a binding profile that includes the most abundant *S. aureus* superantigens SEA and SEB, as well as others, and therefore may provide the chimera with the ability to bind and clear these multiple *S. aureus* superantigens. Table I, supra, shows the binding specificities of the various known SAGs, and may be used to initially select binding components for inclusion in a chimera design. Chimeras constructed accordingly may be evaluated immediately for binding characteristics, and/or subjected to molecular modeling and in vitro evolution aimed at generating improved variants thereof.

Multi-specific anti-SAG chimera compositions may also be formulated from individual chimera components. In one embodiment, for example, a plurality of chimeras having different SAG binding specificities are joined together in order to form the basis for a pharmaceutical composition that would exhibit the combined breadth of specificities represented by the individual chimera components.

Development of Mutatinal Variants:

Variants of native or engineered SAG binding components (e.g., MHC II and TCR components) may exhibit expanded SAG target specificity and/or enhanced binding characteristics. Similarly, variants of chimera designed against a particular SAG may display improved binding characteristics and/or SAG specificities.

Methods of generating and screening mutants are well known, and may be applied to the current invention in order to create such variants. In addition, molecular modeling techniques may be applied in order to evaluate the binding relationships between candidate SAG binding components and SAGs, thereby identifying mutations and variants likely to result in a desired property, such as increased binding affinity or expanded SAG specificity profiles. Provided in the Examples, infra, is a molecular modeling analysis of three exemplary chimeras complexed with target SAGs. More particularly, a systematic analysis of the contact interface in these complexes reveals the nature of various pair wise interactions and provides important clues on single site mutations on the chimera that may enhance the stability of a given superantigen-chimera complex.

Preferred therapeutic chimeras of the invention will have high binding affinities for their target SAGs, preferably greater than the micromolar binding affinities of SAGs to the MHC class II and T cell receptors, and more preferably in the nanomolar to picomolar range. Generally, higher binding affinity receptor mimetics will more effectively prevent SAGs from binding to their receptor targets and forming immune synapses which lead to immune cell activation.

Variants with binding affinity enhancement may be generated using various in vitro evolution strategies or site-directed mutagenesis based on molecular modeling studies. For example, as described herein, the TCRVβ domain imparts SAG binding specificity, affinity enhancement of the TCRVβ domain may yield receptor mimics with more enhanced inhibitory properties against a given SAG, as has been achieved with the Vβ8.2 isoform (increasing binding affinity for SEC3 by ~1000 fold (Kieke et al., 2001, J. Mol. Biol. 307: 1305-15). Using various molecular evolution and mutation techniques, the effective therapeutic range of a chimera incorporating a TCRVβ isoform that multiple SAGs specifically bind potentially may be expanded to capture additional SAGs produced by the same pathogen or by heterologous pathogens.

Methods of measuring binding affinity are well known, and include, for example, surface plasmon resonance analysis and fluorescence activated cell sorting methodologies. In one approach, surface plasmon resonance analysis using the commercially available BIAcore 1000 instrument (Pharmacia) is used. Briefly, the target SAG is immobilized at one or more concentrations, using an amine coupling kit (Pharmacia Biosensor AB). Various concentrations of mutant chimera or SAG binding component are injected into the flow cell and permitted to form complexes with the SAG. The complexes are then allowed to dissociate, and on- and off-rates are calculated from the resulting association and dissociation curves, corrected for non-specific binding, with their ratio yielding the equilibrium binding constant (Kd). Control experiments, in which the chimera or binding component are passed over empty sensor chips are conducted for comparison.

More specifically, the superantigen of interest is immobilized to sensor chips according to the manufacturer instructions (BIAcore, Uppsala, Sweden). SAG at a concentration of 100 μg/ml in 10 mM acetic acid buffer, pH 4.8, is immobilized on CM5 sensor chips through amine coupling. The matrix is activated with EDC/NHS and then excess ligand washed away with ethanolamine. Flow cells without protein are used as a control. Chimera or binding component are passed over the chips at concentrations ranging from 12.5 to 200 nM. Between runs, flow cells are regenerated with 20 μl of 10 mm Glycine, pH 3.03. The association and disassociation phases are used to calculate the affinity using BIAevaluation software 3.0 (BIAcore Uppsala, Sweden). Curve fitting is evaluated by the same program, with a $\chi^2$ value<2.

For determining binding affinity using FACS, the SAG of interest is first biotinylated by incubating 90 μl of 2 mg/ml SAG in PBS with 10 μl 5 mg/ml NHS-Biotin on ice for 1.5 hour. Unbound biotin is removed with a G-25 column. 25 μl 1 μm polystyrene beads coated with avidin ($2.2 \times 10^7$ beads/ml) (Bangs Laboratories, Fishers, Ind.) are mixed with 15 μl biotinylated protein solution (2 mg/ml) for ½ hour at RT. The beads are washed and resuspended in 100 μl PBS. Then 2.5 μl beads are mixed with chimera or a binding component thereof at concentrations ranging from 12.5 to 200 nM in 100 μl and incubated at room temperature for one hour. Binding of chimera (or chimera binding component) to the beads is detected by FACS (Facsclibur, Beckson-Dickenson, San Rose, Calif.).

Based on initial studies, yeast display systems may be effectively used to generate libraries of mutants, which may be screened for high affinity binders using existing methodology. For example, a yeast display library of chimera designed against a particular SAG may be generated using error-prone PCR or similar techniques, expressed on the surface of yeast, and screened for high affinity binders using a fluorescently labeled target SAG. The high affinity binders may be conveniently selected and isolated using flow cytometry. See, e.g., Kieke et al., 2001, supra.

The yeast display system (or other display systems) may be used to screen libraries of randomly mutated binding components (e.g., TCRVβ component) in order to identify variants likely to provide a chimera into which they are incorporated with greater overall binding affinity. Use of the yeast display system may also lead to selection of TCRVβ variants that are cross-reactive and bind to several SAGs with high affinity. Such TCRVβ variants may be used to produce a single cross-reactive chimera that is effective in the treatment of a *S. aureus* infection in which several different SAGs are released. Alternatively, such systems may be used to screen libraries of randomly mutated chimeras in order to isolate high affinity binders directly.

In addition to random mutagenesis techniques, site-directed mutational techniques may be employed in combination with molecular modeling studies aimed at predicting mutations that will increase stability and binding affinity of the interaction complex between SAGs and their specific chimeras or binding components thereof.

Based on molecular modeling studies (see Examples 2 and 3, infra), it can be concluded that backbone interactions make up the majority of all interactions and play a significant role in SAG binding with TSST-1, SEB and SEC3. This may imply that a large subset of Vβ isoforms adopt similar folds, and that all of them bind the same SAG through the common backbone interaction pattern.

In the rational design of specific chimeras, it is possible to enhance the binding affinity by introducing new side chain stabilizing interactions while retaining the backbone interaction. For example, Q18 in the anti-SEB chimera (Example 1, infra) is in close proximity to Q43, F44, L45, Y46 and K98 of SEB (FIG. 9A). The hydrophobic residues F44, L45 and Y46 are located on one side, whereas the polar residues Q43 and K98 are located on the opposite side of Q18. Substitution of Q18 to a threonine or isoleucine may lead to stabilization through hydrophobic interactions.

With respect to the anti-SEC3 chimera described in Example 1, infra, a specific P90N substitution in the linker region may increase polar interactions with the nearby SEC3 residues K56 and N59 (FIG. 9B), thus serving to enhance the stability of the interaction complex. In addition, SEC3 residues K63 and D62 could be potential interaction partners for P90N through their charged side chains.

With respect to the anti-TSST-1 chimera described in Example 1, infra, a A161Y substitution in the TCRVβ component may enhance interactions with the TSST-1 residues P117 and W116, Y115, K118, and Q136 through polar side chain interactions (FIG. 9C), thus enhancing the stability of the complex.

Figure 10:
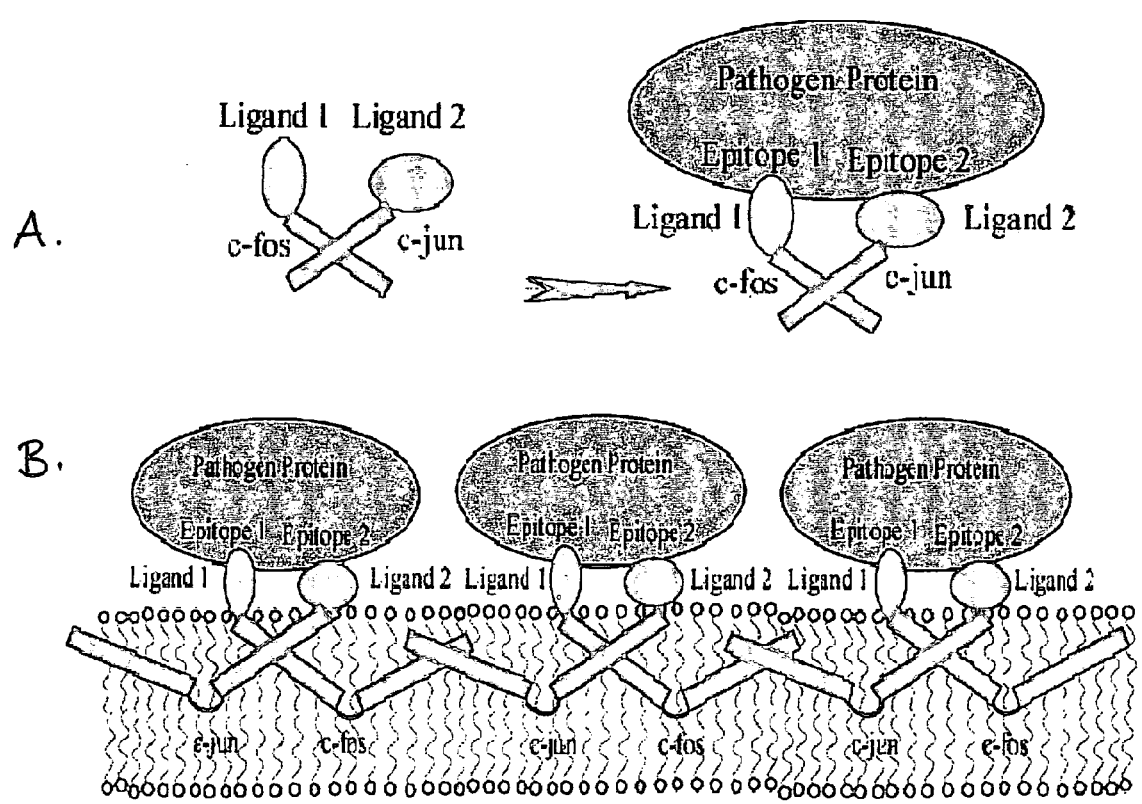
FIG. 10. Schematic representation of chimera constructed with jun-fos linker, (A) in monomeric form, and (B) surface-aggregated in lipid layer.

Another approach to improving the binding affinity of a chimera involves generating compositions comprising the chimera and tags that facilitate the lateral aggregation of the chimera on a substrate (i.e., a liposome surface). In one embodiment, C-terminal c-jun/c-fos tags are attached to the binding components of the chimera. More specifically, one of the binding components of the chimera is tagged with a c-jun_linker_c-jun polypeptide, and the other component is tagged with a c-fos_linker_c-fos polypeptide. The noncovalent dimerization reaction between c-jun and c-fos results in a lateral aggregation pattern of the chimera on a lipid surface, such as a lipid bilayer surface or a spherical particle (FIG. 10). Such compositions may act as a "molecular velcro" for the target SAG(s) (see description of therapeutic applications, infra).

General Nucleic Acid Methodology:

The anti-SAG receptor mimetic chimeras of the invention, and libraries of variants thereof, may be generated using basic nucleic acid methodology that is routine in the field of recombinant genetics. Basic texts disclosing the general methods of obtaining and manipulating nucleic acids in this invention include Sambrook and Russell, *Molecular Cloning, a Laboratory Manual* (3rd ed. 2001) and *Current Protocols in Molecular Biology* (Ausubel et al., eds., John Wiley & Sons, Inc. 1994-1997, 2001 version)).

Typically, the nucleic acid sequences encoding the chimeras of the invention are generated using amplification techniques. Examples of techniques sufficient to direct persons of skill through in vitro amplification methods are found in Berger, Sambrook, and Ausubel, as well as Dieffenfach & Dveksler, *PCR Primers: A Laboratory Manual* (1995): Mullis et al., (1987); U.S. Pat. No. 4,683,202; *PCR Protocols A Guide to Methods and Applications* (Innis et al., eds) Academic Press Inc. San Diego, Calif. (1990); (Innis); Arnheim & Levinson (Oct. 1, 1990) *C&EN* 36-47; The Journal Of NIH Research, 1991, 3: 81-94; Kwoh et al., 1989, Proc. Natl. Acad. Sci. USA, 86: 1173; Guatelli et al., 1990, Proc. Natl. Acad. Sci. USA, 87, 1874; Lomell et al., 1989, J. Clin. Chem., 35: 1826; Landegren et al., 1988, Science, 241: 1077-1080; Van Brunt, 1990, Biotechnology, 8: 291-294; Wu and Wallace, 1989, Gene, 4: 560; and Barringer et al., 1990, Gene 89: 117.

Amplification techniques can typically be used to obtain a population of sequences, e.g., evolved variants of the MHC II or TCR binding components of the chimeras. In generating a population of variants, it is often desirable to obtain amplicons that do not include the primer sequences from the amplification primers. This can be achieved by using primers that include restriction enzyme sites, such as BpmI, that cleave at a distance from the recognition sequence. Such a method is exemplified in U.S. patent application Ser. No. 10/167,634. The amplified population can then be introduced into a chimera construct, thereby generating a library of chimeras for biological activity screening.

Display Libraries:

Libraries of variant components or complete chimeras may be constructed using a number of different display systems. In cell or virus-based systems, the elements of the library can be displayed, for example, on the surface of a particle, e.g., a virus or cell and screened for the ability to interact with other molecules, e.g., a superantigen of interest. In vitro display systems can also be used, in which the library elements are linked to an agent that provides a mechanism for coupling the element to the nucleic acid sequence that encodes it. These technologies include ribosome display and mRNA display.

As noted above, in some instances, for example, ribosomal display, a chimera variant is linked to the nucleic acid sequence through a physical interaction, for example, with a ribosome. In other embodiments, e.g., mRNA display, the chimera may be joined to another molecule via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similar linking group. Other near neutral amino acids, such as Ser can also be used in the linker sequence. Amino acid sequences which may be usefully employed as linkers include those disclosed in Maratea et al., 1985, Gene 40:39-46; Murphy et al., 1986, Proc. Natl. Acad. Sci. USA 83:8258-8262; U.S. Pat. Nos. 4,935,233 and 4,751,180. The linker sequence may generally be from 1 to about 50 amino acids in length, e.g., 2, 3, 4, 6, or 10 amino acids in length, but can be 100 or 200 amino acids in length.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterofunctional linkages.

Phage display technology may also be used for generating and screening libraries of chimeras or components thereof. Construction of phage display libraries exploits the bacteriophage's ability to display peptides and proteins on their surfaces, i.e., on their capsids. Often, filamentous phage such as M13, fd, or f1 are used. Filamentous phage contain single-stranded DNA surrounded by multiple copies of genes encoding major and minor coat proteins, e.g., pIII. Coat proteins are displayed on the capsid's outer surface. DNA sequences inserted in-frame with capsid protein genes are co-transcribed to generate fusion proteins or protein fragments displayed on the phage surface. Phage libraries thus can display peptides representative of the diversity of the inserted sequences. Significantly, these peptides can be displayed in "natural" folded conformations. The fluorescent binding ligands expressed on phage display libraries can then bind target molecules, i.e., they can specifically interact with binding partner molecules such as antigens, e.g., (Petersen, 1995, Mol. Gen. Genet., 249:425-31), cell surface receptors (Kay, 1993, Gene 128:59-65), and extracellular and intracellular proteins (Gram, 1993, J. Immunol. Methods, 161:169-76).

The concept of using filamentous phages, such as M13 or fd, for displaying peptides on phage capsid surfaces was first introduced by Smith, 1985, Science 228:1315-1317. Peptides have been displayed on phage surfaces to identify many potential ligands (see, e.g., Cwirla, 1990, Proc. Natl. Acad. Sci. USA, 87:6378-6382). There are numerous systems and methods for generating phage display libraries described in the scientific and patent literature, see, e.g., Sambrook and Russell, *Molecule Cloning: A Laboratory Manual,* 3rd edition, Cold Spring Harbor Laboratory Press, Chapter 18, 2001; Phage, *Display of Peptides and Proteins: A Laboratory Manual,* Academic Press, San Diego, 1996; Crameri, 1994, Eur. J. Biochem. 226:53-58; de Kruif, 1995, Proc. Natl. Acad. Sci. USA, 92:3938-42; McGregor, 1996, Mol. Biotechnol., 6:155-162; Jacobsson, 1996, Biotechniques, 20:1070-1076; Jespers, 1996, Gene, 173:179-181; Jacobsson, 1997, Microbiol Res., 152:121-128; Fack, 1997, J. Immunol. Methods, 206:43-52; Rossenu, 1997, J. Protein Chem., 16:499-503; Katz, 1997, Annu. Rev. Biophys. Biomol. Struct., 26:27-45;

Rader, 1997, Curr. Opin. Biotechnol., 8:503-508; Griffiths, 1998, Curr. Opin. Biotechnol., 9:102-108.

Typically, exogenous nucleic acids encoding the protein sequences to be displayed are inserted into a coat protein gene, e.g. gene III or gene VIII of the phage. The resultant fusion proteins are displayed on the surface of the capsid. Protein VIII is present in approximately 2700 copies per phage, compared to 3 to 5 copies for protein III (Jacobsson, 1996, supra). Multivalent expression vectors, such as phagemids, can be used for manipulation of the nucleic acid sequences encoding the fluorescent binding library and production of phage particles in bacteria (see, e.g., Felici, 1991, J. Mol. Biol., 222:301-310).

Phagemid vectors are often employed for constructing the phage library. These vectors include the origin of DNA replication from the genome of a single-stranded filamentous bacteriophage, e.g., M13 or f1 and require the supply of the other phage proteins to create a phage. This is usually supplied by a helper phage which is less efficient at being packaged into phage particles. A phagemid can be used in the same way as an orthodox plasmid vector, but can also be used to produce filamentous bacteriophage particle that contain single-stranded copies of cloned segments of DNA.

The displayed protein does not need to be a fusion protein. For example, a chimera or component thereof may attach to a coat protein by virtue of a non-covalent interaction, e.g., a coiled coil binding interaction, such as jun/fos binding, or a covalent interaction mediated by cysteines (see, e.g., Crameri et al., 1994, Eur. J. Biochem., 226:53-58) with or without additional non-covalent interactions. Morphosys have described a display system in which one cysteine is put at the C terminus of the scFv or Fab, and another is put at the N terminus of g3p (MorphoSys; Munich, Germany). The two assemble in the periplasm and display occurs without a fusion gene or protein.

The coat protein need not endogenous. For example, DNA binding proteins can be incorporated into the phage/phagemid genome (see, e.g., McGregor & Robins, 2001, Anal. Biochem., 294:108-117,). When the sequence recognized by such proteins is also present in the genome, the DNA binding protein becomes incorporated into the phage/phagemid. This can serve as a display vector protein. In some cases it has been shown that incorporation of DNA binding proteins into the phage coat can occur independently of the presence of the recognized DNA signal.

Other phage can also be used. For example, T7 vectors, T4 vector, T2 vectors, or lambda vectors can be employed in which the displayed product on the mature phage particle is released by cell lysis.

Another methodology is selectively infective phage (SIP) technology. which provides for the in vivo selection of interacting protein-ligand pairs. A "selectively infective phage" consists of two independent components. For example, a recombinant filamentous phage particle is made non-infective by replacing its N-terminal domains of gene 3 protein (g3p) with a protein of interest, e.g., an antigen. The nucleic acid encoding the antigen can be inserted such that it will be expressed. The second component is an "adapter" molecule in which the fluorescent ligand is linked to those N-terminal domains of g3p that are missing from the phage particle. Infectivity is restored when the displayed protein (e.g., a fluorescent binding ligand) binds to the antigen. This interaction attaches the missing N-terminal domains of g3p to the phage display particle. Phage propagation becomes strictly dependent on the protein-ligand interaction. See, e.g., Spada, 1997, J. Biol. Chem. 378:445-456; Pedrazzi, 1997, FEBS Lett. 415:289-293; Hennecke, 1998, Protein Eng. 11:405-410.

In addition to phage display libraries, analogous epitope display libraries can also be used. For example, the methods of the invention can also use yeast surface displayed libraries (see, e.g., Boder, 1997, Nat. Biotechnol., 15:553-557 and Feldhaus a., 2003, Nat. Biotechnol., 21, 163-170), which can be constructed using such vectors as the pYD1 yeast expression vector. Yeast display wherein a library of elements (e.g., a library of chimera random mutants) is expressed on the yeast cell surface as a fusion with the yeast Aga2p protein may be used in combination with flow cytometry sorting using a fluorescently labeled target SAG (Kieke et al., 2001, supra). See also, U.S. Pat. Nos. 6,300,065 and 6,423,538.

In one embodiment, a yeast display system may be used to display and screen for variants with higher binding affinities, broader SAG specificity, etc. Initial studies have demonstrated that the chimeras of the invention may be displayed on the yeast cell surface, confirming the utility of this particular display system for screening chimera or chimera component variants with modulated biological properties. Other potential display systems include mammalian display vectors and E. coli libraries. The use of mammalian or other eukaryotic display systems are preferred so that post-translational modifications that may important in SAG binding or affinity are present in the expression products.

In vitro display library formats known to those of skill in the art can also be used, e.g., ribosome displays libraries and mRNA display libraries. In these in vitro selection technologies, proteins are made using cell-free translation and physically linked to their encoding mRNA after in vitro translation. In typical methodology for generating these libraries, DNA encoding the sequences to be selected are transcribed in vitro and translated in a cell-free system.

In ribosome display libraries (see, e.g., Mattheakis et al., 1994, Proc. Natl. Acad. Sci USA 91:9022-9026; Hanes & Pluckthrun, 1997, Proc. Natl. Acad. Sci USA, 94: 4937-4942) the link between the mRNA encoding the chimera and the chimera is the ribosome itself. The DNA construct is designed so that no stop codon is included in the transcribed mRNA. Thus, the translating ribosome stalls at the end of the mRNA and the encoded protein is not released. The encoded protein can fold into its correct structure while attached to the ribosome. The complex of mRNA, ribosome and protein is then directly used for selection against an immobilized SAG target. The mRNA from bound ribosomal complexes is recovered by dissociation of the complexes with EDTA and amplified by RT-PCR.

Methods and libraries based on mRNA display technology, also referred to herein as puromycin display, are described, for example in US Pat. Nos. 6,261,804; 6,281,223; 6207446; and 6,214553. In this technology, a DNA linker attached to puromycin is first fused to the 3' end of mRNA. The protein is then translated in vitro and the ribosome stalls at the RNA-DNA junction. The puromycin, which mimics aminoacyl tRNA, enters the ribosomal A site and accepts the nascent polypeptide. The translated protein is thus covalently linked to its encoding mRNA. The fused molecules can then be purified and screened for binding activity. The nucleic acid sequences encoding ligands with binding activity can then be obtained, for example, using RT-PCR. The chimeras or components thereof and sequences, e.g., DNA linker for conjugation to puromycin, can be joined by methods well known to those of skill in the art and are described, for example, in U.S. Pat. Nos. 6,261,804; 6,281,223; 6207446; and 6,214553.

Other technologies involve the use of viral proteins (e.g., protein A) that covalently attach themselves to the genes that encodes them. Fusion proteins are created that join the chimera or component thereof to the protein A sequence, thereby providing a mechanism to attach the chimeras or components thereof to the genes encoding them.

Plasmid display systems rely on the fusion of displayed proteins to DNA binding proteins, such as the lac repressor (see, e.g., Gates et al., 1996, J. Mol. Biol., 255:373-386; 1996, Methods Enzymol. 267:171-191). When the lac operator is present in the plasmid as well, the DNA binding protein binds to it and can be co-purified with the plasmid. Libraries can be created linked to the DNA binding protein, and screened upon lysis of the bacteria. The desired plasmid/proteins are rescued by transfection, or amplification.

Library Screening:

Methods of screening libraries of chimeras or components thereof are also well known in the art. Such libraries are typically screened using a superantigen of interest. The SAG may be attached to a solid surface or a specific tag, such as biotin. The SAG is incubated with a library of a chimera or a component thereof (i.e., random mutants of one of the binding components, e.g., TCRVβ). Those polypeptides that bind to the superantigen are then separated from those that do not using any of a number of different methods. These methods involve washing steps, followed by elution steps. Washing can be done, for example, with PBS, or detergent-containing buffers. Elution can be performed with a number of agents, depending on the type of library. For example, an acid, a base, bacteria, or a protease can be used when the library is a phage display library. Selected clones may be subjected to further screening and individual clones evaluated for SAG binding profiles and binding affinities.

To facilitate the identification and isolation of the superantigen-bound chimera or component thereof, the chimera or component thereof may also be engineered as a fusion protein to include selection markers (e.g., epitope tags). Antibodies reactive with the selection tags present in the fusion proteins or moieties that bind to the labels can then be used to isolate the complex via the epitope or label. For example, TCRVβ-SAG complexes can be separated from non-complexed display particle using antibodies specific for the antibody selection "tag" e.g., an SV5 antibody specific to an SV5 tag. In libraries that are constructed using a display vector, such as a phage display vector, the selected clones, e.g., phage, are then used to infect bacteria.

Other detection and purification facilitating domains include, e.g., metal chelating peptides such as polyhistidine tracts (HIS tags) and histidine-tryptophan modules that allow purification on immobilized metals, protein A domains that allow purification on immobilized immunoglobulin, or the domain utilized in the FLAG extension/affinity purification system (Immunex Corp, Seattle Wash.).Any epitope with a corresponding high affinity antibody can be used, e.g., a myc tag (see, e.g., Kieke, 1997, Protein Eng. 10:1303-1310), V5 (Invitrogen, San Diego, Calif.), or an E-tag (Pharmacia Biotech, Uppsala, Sweden). See also Maier, 1998, Anal. Biochem. 259:68-73; Muller, 1998, Anal. Biochem. 259:54-61.

The inclusion of a cleavable linker sequences such as Factor Xa, tobacco etch virus protease or enterokinase (Invitrogen, San Diego, Calif.) between the purification domain and binding site may be useful to facilitate purification. For example, an expression vector of the invention may include a polypeptide-encoding nucleic acid sequence linked to six consecutive histidine residues. These residues bind with high affinity to metal ions immobilized on chelating resins even in the presence of denaturing agents and can be mildly eluted with imidazole. The use of a HIS tag sequence in combination with an enterokinase cleavable linker sequence has been successfully applied to the purification of an anti-SEB chimera (Lehnert et al., 2001, supra).

Selection tags can also make the epitope or binding partner detectable or easily isolated by incorporation of, e.g., predetermined polypeptide epitopes recognized by a secondary reporter/binding molecule, e.g., leucine zipper pair sequences; binding sites for secondary antibodies; transcriptional activator polypeptides; and other selection tag binding compositions. See also, e.g., Williams, 1995, Biochemistry, 34:1787-1797.

Typical screening protocols employ multiple rounds of selection to identify a clone with the desired properties. For example, it may be desirable to select a chimera or component thereof with a binding avidity for a specified SAG or set of SAGs. Selection may be employed to isolate high affinity binders, using increasingly stringent binding conditions can be used to select chimeras or binding components thereof that bind to a target superantigen at increasingly greater binding affinities. One method of performing this selection is by decreasing concentrations of a superantigen to select TCRVβ mutants with a higher binding affinity for the superantigen. A variety of other parameters can also be adjusted to select for high affinity binding components, e.g., increasing salt concentration, temperature, and the like.

Once a chimera or component thereof is selected, the encoding nucleic acid is readily obtained. This sequence may then be expressed using any of a number of systems to obtain the desired quantities of the protein. There are many expression systems for that are well know to those of ordinary skill in the art. (See, e.g., *Gene Expression Systems,* Fernandes and Hoeffler, Eds. Academic Press, 1999; Ausubel, supra.) Typically, the polynucleotide that encodes the chimera or component thereof is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes" or "constructs". Accordingly, the nucleic acids that encode the joined polypeptides are incorporated for high level expression in a desired host cell. For the production of therapeutic chimera, mammalian or other eukaryotic cells, such as COS, CHO or bacculovirus cells, are used for expressing recombinant chimera, in order to maintain post-translational modifications important in SAG binding. As is known in the art, different organisms preferentially utilize different codons for generating polypeptides. Such "codon usage" preferences may be used in the design of nucleic acid molecules encoding the chimeras of the invention in order to optimize expression in a particular host cell system.

Evaluation and Selection of Therapeutic Chimera:

In order to develop therapeutically effective, high-affinity, high-specificity anti-SAG chimeras of the invention, the iterative application of structural, cell and animal models may be used to design candidate chimera, evaluate performance characteristics, and ultimately select chimera to be applied therapeutically.

Briefly, as an example of the application of this iterative selection scheme, the initial step involves the structural design of the chimera, as described supra. Chimera constructs may then be expressed in a number of different cell types (*E. coli,* insect, human cells) using various expression vectors and methods well known in the art. Candidate chimera expressed in these systems may be evaluated in cell based models for their ability to attenuate SAG-mediated immune events, such as IL-2 release and T cell proliferation assays (see below and Example 1, infra). Finally, chimera showing inhibitory effects may be evaluated in animal models of SAG infection, such as, for example, models which measure the extent to which a chimera can protect mice against lethal challenge with superantigen, as further described infra.

In Vitro Cell Based Assays:

Various in vitro assays may be used to assess a test chimera for its ability to block SAG binding to immune cells. For example, in vitro cell based assays for T-cell proliferation are well known and reliable indicators of T-cell activation. Such an assay is described in Example 1, infra. In addition, assays measuring the release of cytokines induced by SAGs may be used to assess a test chimeras ability to block SAG binding to cells. For example, the IL-2 release assay described in Example 1, infra, or a similar assay may be used.

In Vivo Infection Models for Use in Testing Anti-SAG Chimera:

A number of animal model systems may also be used to assess the ability of an anti-SAG chimera to inhibit binding of the target SAG to immune cells.

In one approach, a mouse model is used to assess protection and rescue from superantigen-induced lethal shock. Interestingly, unlike their human counterparts, mouse T cells display a decreased sensitivity to *staphylococcal* superantigens and a resistance to toxic shock (Uchiyama et al., 1989, Clin. Exp. Immunol. 75:239-244). However, satisfactory lethal mouse models have been developed by initial sensitization of the animal to galactosamine prior to superantigen treatment (Galanos et al., 1979, Proc. Natl. Acad. Sci. USA 76: 5939-5943). Initially, to assay for protective effects mediated by a chimera of the invention, different concentrations of the chimera are incubated with lethal doses of superantigen. Pathogen-free BALB/c mice are then challenged with the toxin/chimera mixture intraperitoneally in parallel with toxin alone, chimera alone, and mock treatment controls. Lipopolysaccharide is administered three hours prior to initial treatment to help boost the immune response of the mice. Lethality will be recorded 12-30 hours later.

The half-maximal killing of mice exposed to a lethal dose of SEB has been assayed to occur in as little as 8 hours following treatment with 2 mg of SEB (Miethke et al., 1992, J. Exp. Med. 175:91-98). It is anticipated that mice would exhibit a longer life span following superantigen/chimera treatment compared to control mice injected with only the toxin, if the chimera is effective at binding to the superantigen and preventing T cell activation and lethal shock.

In another approach, a variant of, the above experiment may be performed. Briefly, the chimera protein is injected intraperitoneally into the mouse 30 minutes prior to treatment with the superantigen. In this case, the chimera would display protective activity only upon complex formation with the toxin in the body. This protocol may provide a more realistic model in which animals, or eventually humans, can be inoculated with a therapeutic chimera as a prophylactic prior to *Staphylococcal* infection.

In addition to investigating the protective effects of different chimeras, the ability of a chimera to rescue mice from superantigen-induced lethal shock may be tested as follows. Mice are injected intraperitoneally with the chimera protein at different time points 0-3 hrs following treatment with lethal doses of superantigens. The success of this strategy is strongly dependent on how efficiently the superantigen targets immune cells in the body for stimulation. A prolonged life span in the mice would indicate that the injected chimera is able to intercept the superantigen before it encounters immune cells. Since the half-life of the chimera protein in the body is unknown, multiple injections of the protein in the 0-3 hr time range to boost chimera activity in the mice may be required to observe a rescue phenotype. Moreover, from the extensive advances in vaccine development, liposomes have been successfully used to stabilize purified protein injected into the body (Lowell et al., 1996, Infect. Immun. 64:1706-1713). Thus, chimera incorporated into liposomes can be introduced into mice challenged with superantigen to prolong the protein half-life.

Another assay involves suppression of *Staphylococcus aureus*-induced sepsis and cellulitis in mice by treatment with chimera protein. This mouse model system differs from the one described above, in that intact *S. aureus* bacteria rather than their toxins are introduced into the mice. Both vaccination with the *S. aureus* protein RAP (RNAIII activating protein) and treatment with the peptide RIP (RNAIII inhibiting peptide) produced by an unrelated bacteria were shown to protect mice from lethality caused by toxic shock (sepsis) and skin lesion formation (cellulitis) (Balaban et al., 2000, Peptides 21:1301-1311). The protective effects of these reagents have been attributed to their ability to inactivate RNAIII, which is required for the transcription/translation of *S. aureus* superantigens.

As an example, the *S. aureus* smith diffuse (SD) strain may be used in such a model system. This strain is an encapsulated strain that produces exopolysaccharides that are antigenically identical to many clinical strains tested. When injected in high concentration, *S. aureus* SD causes sepsis due to the secretion of a number of toxins, including the superantigen enterotoxins and TSST-1. At a lower concentration, *S. aureus* SD causes skin lesions, allowing the host to mount an immune response.

The inhibitory efficacy of a chimeras may be tested in this mouse model by incubating *S. aureus* SD bacteria with different concentrations of the chimera and injecting this mixture subcutaneously together with Cytodex® dextran beads (Sigma-Aldrich Co.) into six week old male Hairless immunocompetent mice to induce sepsis or cellulitis. The Cytodex® beads enhance the immunogenicity of the *S. aureus* SD infection, but do not cause any lesion formation when injected alone. Alternatively, chimera protein can be injected intravenously 0-12 hours following bacterial challenge to examine whether the chimera can rescue the disease effects of *S. aureus* SD once infection in the body has already begun. Optionally, multiple injections of the chimera or liposome-based carrier vesicles containing chimera may be employed to maintain an active protein presence in the mice. The peptide RIP may be used as a negative control to block the early stages of toxin production altogether.

Infected animals are then observed daily for mortality and/or development of skin lesions. If the chimeras are effective in binding to the superantigens released from the *S. aureus* SD strain, then animals receiving the chimeras should exhibit an extended life span and smaller or absent skin lesions compared to control mice infected with *S. aureus* SD alone. Since this mouse model utilizes intact *S. aureus* SD, which secretes a wide array of toxins, it may be particularly appropriate in assaying for cross-reactive chimeras displaying a broad SAG binding specificity.

Therapeutic/Pharmaceutical Compositions:

The chimeras of the invention may be formulated into pharmaceutical compositions comprising a carrier suitable for the desired delivery method and administered to patients exposed to superantigen. Suitable carriers include any material which when combined with the chimera retains their anti-SAG function and is non-reactive with the subject's immune system. Examples include, but are not limited to, any of a number of standard pharmaceutical carriers such as sterile phosphate buffered saline solutions, bacteriostatic water, and the like.

Monomeric chimeras of the invention are likely to be cleared rapidly from the circulation, due to their relatively small size, which is below the renal threshold.

Circulation clearance times may be lengthened by increasing the mass of the chimera pharmaceutical composition. This may be achieved by formulating the chimeras of the invention into liposomes and other particle carriers, into multimeric compositions, as described, supra, and/or by the addition of a large polypeptide tag.

In one embodiment, a chimera composition is incorporated into large unilamellar vesicles ("LUVs") of approximately 50 to 500 nm in diameter. Chimera compositions including fused polypeptides comprising elements A, X and B, c-fos/c-jun linked elements A and B, and dimerizable c-jun_linker_c-jun/c-fos_linker_c-fos linked elements A and B are examples of compositions that may be formulated in this manner, the latter example providing a means for creating a lateral aggregation of chimera on the lipid surface via fos-jun dimerization.

Such pharmaceutical formulations may be administered via any effective route, including without limitation intravenous, intraperitoneal, intramuscular, intradermal, intranasal, subcutaneous and the like. The preferred route of administration for acute systemic conditions, such as toxic shock syndrome, is by intravenous and/or intraperitoneal injection. A preferred formulation for intravenous injection comprises the chimera pharmaceutical composition in a solution of preserved bacteriostatic water, sterile unpreserved water, and/or diluted in polyvinylchloride or polyethylene bags containing 0.9% sterile Sodium Chloride for Injection, USP. The preparation may be lyophilized and stored as a sterile powder, preferably under vacuum, and then reconstituted in bacteriostatic water containing, for example, benzyl alcohol preservative, or in sterile water prior to injection.

Treatment of Toxic Shock and SAG-Induced Syndromes:

Superantigens have been implicated in three major classes of human diseases (Bernal et al., JI. Clin. Immunol., 19:149-157, 1999; Leung et al., JI. Invest. Dermatology, 105:37S42S, 1995): food poisoning, toxic shock syndrome in menstrual women, skin disorders such as atomic dermatitis & psoriasis. Although different diseases involve different target cells and tissues T cell proliferation is associated with all of them. However, the level of initial TCRVβ expansion (and subsequent clonal deletion or anergy) is different in different diseases. For example, in toxic shock syndrome the presence of TSST-1 in tampon-vaginal contact area may cause a large release of TSST-1 in the blood stream and a huge T cell proliferation. In food poisoning, the level of T cell proliferation may not that large; and in addition to T cell proliferation attachment of superantigen to gut epithelial cells may also contribute to the disease manifestation. Therefore, the design of a chimera targeted against a given superantigen involved in a specific disease should be tailored to have not only the TCRVβ specificity but also the ability to block binding to cells belonging to the disease targets (skin or gut).

Prophylactic Treatment:

The therapeutic chimeras of the invention may also be employed prophylactically against superantigen diseases. Such applications may be particularly important in managing situations involving high risk of *Staphylococcal* or *Streptococcal* infections, where SAG-mediated consequences are likely and not easily treated, such as in battlefield scenarios, bioterrorism events, and the like.

Chimeras which have demonstrated efficacy against an SAG or group of SAGs may be formulated into prophylactic compositions that are administered to individuals at risk of encountering infection with pathogens producing such SAGs.

Biosensors with Anti-SAG Chimeras:

The anti-SAG chimeras of the invention will also have applications in detecting the presence of SAGs, including their use in biosensor applications. The chimeras of the invention may be incorporated into a variety of protein microarray formats, and utilized for detection, screening, quantification and monitoring purposes. In general, an anti-SAG microarray will comprise one or more chimeras, attached directly or indirectly to a substrate element, such as a glass slide, plastic microtiter plates, polymer beads and microspheres, and the like, optionally functionalized to bind or associate stably with array components.

A variety of substrate materials are available, including a number of polymer hydrogel materials which are particularly suited to water soluble biomolecules like the chimeras of the invention. Hydrogel microbeads may also be used to bind chimera, arrayed in a column or similar vessel, and used to capture target superantigen from samples delivered into or through the column, capillary or similar vessel. Column type arrays may provide certain advantages, such as the ability to pass sample material through the column on a continuous basis. In another application, LUVs populated with chimera or another lipid based substrate are used as the SAG capture device in a biosensor. The surface of such substrates will be comprised of surface-aggregated chimera at high density, and will act as a sink for target SAGs. Target SAGs passing over the surface of the substrate will be bound and captured by the chimera. Detection of the capture is achieved via the associated detection system built-in to the biosensor platform. Such systems are well known in the art and include, for example, optical and electrical detection systems.

EXAMPLES

Example 1

Production and in vitro Evaluation of Chimeric Receptor Mimetics Against SEB, SEC3, and TSST-1 SAGS Materials and Methods Cloning of Chimera Genes:

A chimera against SEB was constructed as previously described (Lehnert et al., 2001, supra).

TSST-1 and SEC3 specific chimeras were constructed as follows. The DRα and linker domains were PCR amplified from the SEB construct using the primers

```
5'gatcagatctatcaaagaagaacatgtg3'    (SEQ ID NO: 11)
and
5'gatcgctagccgctggtggcgccgtcg3'     (SEQ ID NO: 12)
``` to add BgIII (bold) and NheI (underline) sites to the 5' and 3' ends, respectively.

The DRα/linker region was ligated into BamHI/NheI-digested pRSETc vector (Stratagene, La Jolla, Cailf.) using T4 ligase (NEB). The pRSETc vector introduces an N-terminal 6× His tag that allows for protein purification with the TALON™ metal affinity resin (Clontech Laboratories, Inc. Mountain View, Cailf.).

The TSST-1 TCRVβ2 domain was constructed in two steps. First, the following four oligonucleotides were used:

```
OLIGONUCLEOTIDE A:
5'ctagccaacatccgagcagggttatctgtaag   (SEQ ID NO: 13)

agtggaacctctgtgaagatcgagtgccgttccc tggactttcaggccacaactatgttttggtaccg tcag3'

OLIGONUCLEOTIDE B:
5'cgggaactgacggtaccaaaacatagttgtgg   (SEQ ID NO: 14)

cctgaaagtccagggaacggcactcgatcttcac agaggttccactcttacagataaccctgctcgga tgttg3'

OLIGONUCLEOTIDE C:
5'ttcccgaaacagagtctcatgctgatggcact   (SEQ ID NO: 15)

tccaatgagggctccaaggccacatacgagcaag gcgtcgagaaggacaagtttctcatcaaccatgc aagcctgaccttgtccG3'

OLIGONUCLEOTIDE D:
5'AATTCggacaaggtcaggcttgcatggttgat   (SEQ ID NO: 16).

gagaaacttgtccttctcgacgccttgctcgtat gtggccttggagccctcattggaagttgccatca gcatgagactctgttt3'.
```

Two μl of 100 μM oligonucleotides A, B, C, and D were annealed together in the A/B and C/D configuration for 5 min at 70° C. and allowed to cool slowly to room temperature. The annealed oligonucleotides were then phosphorylated with T4 polynucleotide kinase (NEB) using 10 μM ATP for 30 min at 37° C. The two phosphorylated, annealed A/B and C/D oligonucleotides recreated 5' NheI (underlined) and 3' EcoRI (capitalized) sites and were ligated into the NheI/EcoRI-digested pRSETc vector containing the DRα/linker region.

In the second step, an additional 19 residues of the TCRVβ sequence were appended at the C-terminus to include a second cysteine residue that plays an important role in domain stability. To accomplish this, the existing cloned DRα/linker/TCRVβ sequence was PCR amplified using the following primers:

```
                                     (SEQ ID NO: 17)
5'gatcagatctatcaaagaagaacatgtg3'
and
                                     (SEQ ID NO: 18)
5'ggacaaggtcaggcttgcatggttgatgagaaa3'
```

This amplification introduced a 5' BgIII (bold) site and a 3' blunt end site.

The following two oligonucleotides were annealed together, phosphorylated, and combined with the DRα/linker/TCRVβ PCR product and BamHI/EcoRI-digested pRSETc in a ligation reaction.

```
OLIGONUCLEOTIDE E:
5'accctgaccgttacctctgctcac-          (SEQ ID NO: 19)
ccggaag-
actcttctttctacatctgctctgct-
tagG3'

OLIGONUCLEOTIDE F:
5'AATTCctaagcagagcagatgta-           (SEQ ID NO: 20)
gaaagaag-
agtcttccgggtgagcagaggtaacg-
gtcaggg
t3'
```

The final intact construct was confirmed by DNA sequencing.

The SEC3 TCRVβ domain sequence was PCR amplified from a mutagenized variant mL2.1/A52V (provided by D. Kranz, University of Illinois, Champaign-Urbana)(27) using the following primers:

```
                                     (SEQ ID NO: 21)
5'gatcgctagcgtgacattgagctgtaatcag3'

(SEQ ID NO: 22)
5'gatcGAATTCctaggcacagaagtacactgatgt3'
```

Figure 4:
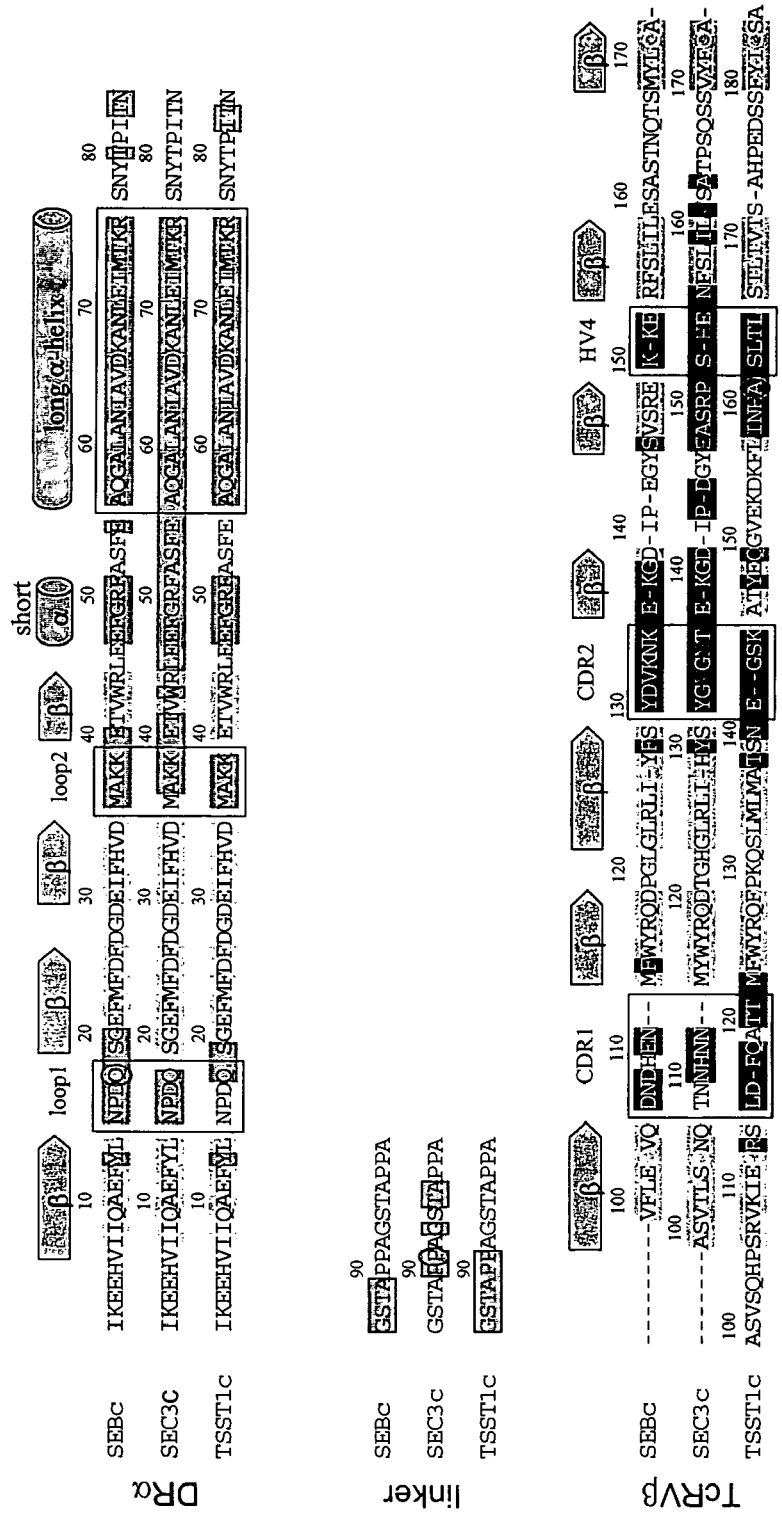
FIG. 4. Structural alignment of the SEB-specific (SEBc), SEC3-specific (SEC3c) and TSST-1-specific (TSST-1c) chimera sequences. The chimeras are composed of three domains, DRα1 (top), linker (middle), and TCRVβ (bottom). Residue numbers are given at the top of each line. Secondary structure elements and designations for the major binding regions, loop 1, loop 2 and the long α-helix in the DRα1 domain and CDR1, CDR2 and, HV4 of the TCRVβ domain are marked with boxes. The secondary structure elements β-sheets (light gray) and α-helices (dark gray), and the contact residues for DRα1 (cyan), linker (red), and TCRVβ (blue) are highlighted for each sequence. Cysteine residues that form a disulfide bridge in the native TCRVβ domain are colored in yellow and the mutagenized Vβ8.2 residues in the SEC3c TCRVβ are colored in red. Circled residues are candidates for site-directed mutagenesis that may enhance binding affinity based on molecular modeling studies (see infra and FIG. 9).

The resulting amplification product introduces 5' Nhe I (underlined) and 3' EcoRI (capitalized) sites for cloning into NheI/EcoRI-digested pRSETc plasmid containing the DRα/linker domain. The amplified Vβ8.2 fragment contains seven out of the nine original mutations in the mL21/A52V mutant (FIG. 4). The two remaining mutations, G17E and G96V, lie outside the consensus TCRVβ domain used for the human Vβ2 and Vβ3 sequences.

Protein Overexpression and Purification:

The pRSETc vectors containing each of the three chimeras were transformed into BL21 *E. coli* competent cells. Cells were induced for expression with 2 mM IPTG for 5 hrs, lysed with 1 mg/ml lysozyme on ice for 30 min, followed by treatment with 10 μg/ml DNase and 10 mM $MgCl_2$ for an additional 30 min, and centrifuged at 50,000 rpm for 30 min. Cell pellets were resuspended in 20 mM Tris-Cl, 100 mM NaCl, 8 M urea, 1% Tween-20 (pH 8.0), homogenized using a probe sonicator, and centrifuged at 50,000 rpm for 30 min. The resultant supernatants were incubated with TALON™ Metal Affinity Resin (Clontech), and purification of the His-tagged chimeras was performed according to the manufacturer's instructions. Briefly, the lysates were rocked for 20 min at room temperature, the resin washed twice with 20 mM Tris-Cl, 100 mM NaCl, 8 M urea, 1% Tween-20, 10 mM imidazole (pH 7.0), and the adsorbed chimera protein eluted with 20 mM Tris-Cl, 100 mM NaCl, 8 M urea, 1% Tween-20, 100 mM imidazole (pH 5.3). The proteins were dialyzed stepwise in decreasing concentrations of urea: (1) PBS, 1% Tween-20, 4 M urea, (2) PBS, 1% Tween-20, 2M urea, and finally (3) PBS, 1% Tween-20. Following quantitation using BCA protein assay reagents (Pierce), proteins were stored at 4° C. and used in experiments within 2 weeks.

Human Cell Culture and Inhibition Studies:

The SEB, TSST-1, and SEC3 toxins were obtained from Toxin Technology, Inc. Human donor-matched peripheral blood mononuclear cells (PBMCs) and dendritic cells (DCs) were obtained from Clonetics, prepared in a 20:1 ratio, and cultured in LGM3 media supplemented with 10% donor matched human serum at 37° C. in 5% $CO_2$. For the dose response curves, increasing concentrations of either SEC3 or TSST-1 were incubated with ~$10^6$ PBMCs/DCs in 1 ml for 10 hrs.

For inhibition studies, either 20 pM SEC3 or 50 pM TSST-1 were incubated with increasing concentrations of the three chimeras, 5×, 10× or 20× the molar concentration of the SAGs or left untreated for 1 hr at 37° C. The SAG/chimera mixtures were then incubated with ~$10^6$ PBMCs/DCs for 10 hrs at 37° C.

Cell supernatants were collected and IL-2 release measured using the standard sandwich ELISA. 2 µg/ml of capture IL-2 antibody (Pharmingen) were adhered to Nunc Immunosorp 96 well plates overnight in 0.1 M sodium carbonate, pH 9.5. The following day, wells were washed with PBS/0.05% Tween-20, blocked with Assay Diluent (Pharmingen) for 1 hr, and incubated with the cell supernatants for 2 hr. Wells were then incubated with 1 µg/ml of biotinylated detection anti-IL-2 antibody (Pharmingen), followed by 1:1000 dilution of streptavidin-HRP, for 1 hr each. Signal was developed using the Substrate Kit (Pharmingen) and 2 M $H_2SO_4$ stop solution. Colorimetric changes were measured using a Labsystems Multiskan Plus plate reader (Fisher Scientific, Springfield, N.J.), and concentrations of IL-2 were determined against a standard curve using defined amounts of recombinant IL-2 in ELISAs performed in parallel.

Cell Proliferation Assay:

T cell proliferation was measured using the Vialight HS cell proliferation/cytotoxicity kit (BioWhittaker, LOCATION), according to the manufacturer's instructions. Briefly, $10^5$ PBMCs/DCs (20:1) were plated in white-walled, clear-bottomed 96 well tissue culture plates and treated with 1 nM TSST-1 or 1 nM SEC3 in the presence or absence of varying concentrations of the purified chimeras for 4 days. Only $10^5$ PBMCs were used for stimulation with 1 pM SEB. 100 µl of Nucleotide Releasing Reagent was added to each well for 15 min to extract the ATP, followed by 20 µl of ATP Monitoring Reagent. The plate was then loaded into a luminometer (Turner Designs, Inc.) within 10 min of after addition of the ATP Monitoring Reagent for measurement of light emission.

Results:

Type-Specific Inhibition of IL-2 Release by Chimeras:

The three chimeric inhibitors, SEBc, TSST-1c, and SEC3c, were expressed in *E. coli* and purified using TALON™ metal affinity resin that binds to the 6× His tag at the N-termini of the proteins. To determine whether the different chimeras specifically inhibited the cytokine release induced by the SAG against which the chimera was designed, ELISAs were performed to quantify SAG-induced IL-2 release in the presence of each of the chimerc proteins.

To determine the SAG concentration to use for cell activation and incubation with the inhibitory chimeras, donor-matched peripheral blood mononuclear cells (PBMCs) and dendritic cells (DCs) in a 20:1 ratio were stimulated with increasing concentrations of TSST-1, SEC3 or SEB to measure the dose response. Optimally, inhibition tests for the chimera should be conducted with stimulated cells that release intermediate levels of cytokine release (~40-100 pg/ml at 10 hrs). Any inhibitory effects mediated by the chimera may be difficult to observe in barely-stimulated (IL-2 release<10 pg/mL at 10 hrs) or overstimulated (IL-2 release ~500 pg/mL at 10 hrs) cells. Concentrations of 50 pM TSST-1 and 20 pM SEC3 stimulated ~68.4 and ~47 pg/mL IL-2 release, respectively, and these concentrations were used in the inhibition of cytokine release assays.

TSST-1 or SEC3 was incubated with 5×, 10×, and 20× the SAG concentration of each of the three purified chimeras, SEBc, TSST-1c, and SEC3c. The resultant chimera/SAG mixtures were subsequently incubated with $10^6$ (20:1) PBMCs/DCs for 10 hrs to stimulate cell activation. Cell supernatants were then collected, and IL-2 release was measured by ELISA.

Figure 5:
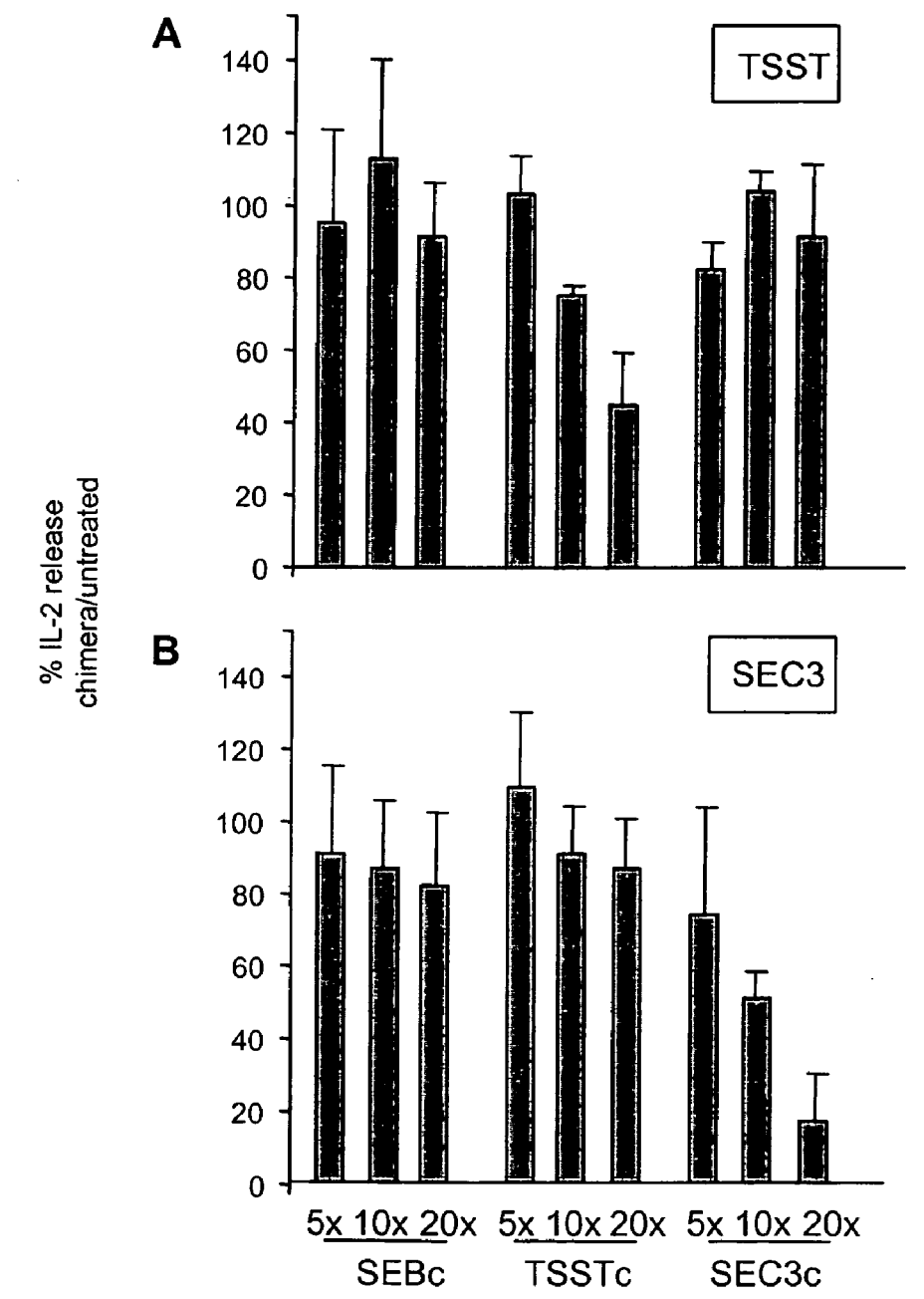

As shown in FIGS. 5A and 5B, the TSST-1 and SEC3 chimeras inhibited IL-2 release in a SAG type-specific and concentration-dependent manner, when compared to cells stimulated with SAG alone. TSST-1c at 10× and 20× concentration showed ~25% and ~55% reduction in IL-2 release, respectively. In contrast, SEBc and SEC3c appeared to have minimal effects in inhibiting IL-2 release in TSST-1-stimulated cells. Similarly, SEC3c specifically inhibited IL-2 release in SEC3-stimulated cells by ~45% and ~80% at 10× and 20× concentrations of SEC3c, respectively, whereas TSST-1c and SEBc did not exhibit any significant inhibition. Given that the DRα and linker domains in the three chimeras are identical, these results indicate that the use of different TCRVβ isoforms imparted specificity to the chimeric proteins in the inhibition of SAG-stimulated cells.

Type-Specific Inhibition of Cell Proliferation by Chimeras:

In addition to measuring cytokine release, the capacity of the different chimeras to inhibit T cell proliferation inhibition in a SAG type-specific manner was evaluated. Appropriate SAG concentrations to stimulate the PBMC/DC model system utilized were determined by obtaining dose response curves using the Vialight cell proliferation assay. In this method, cell proliferation is measured by bioluminescent detection of cellular ATP content, which is increased in proliferating cells. As observed for cytokine release, SEB was significantly more potent in stimulating T cell proliferation, compared to the other two SAGs. In particular, 1 pM SEB was sufficient to stimulate T cell proliferation in PBMCs alone, without the DCs, to a level comparable to that induced by 1 nM TSST-1 or SEC3.

Figure 6:
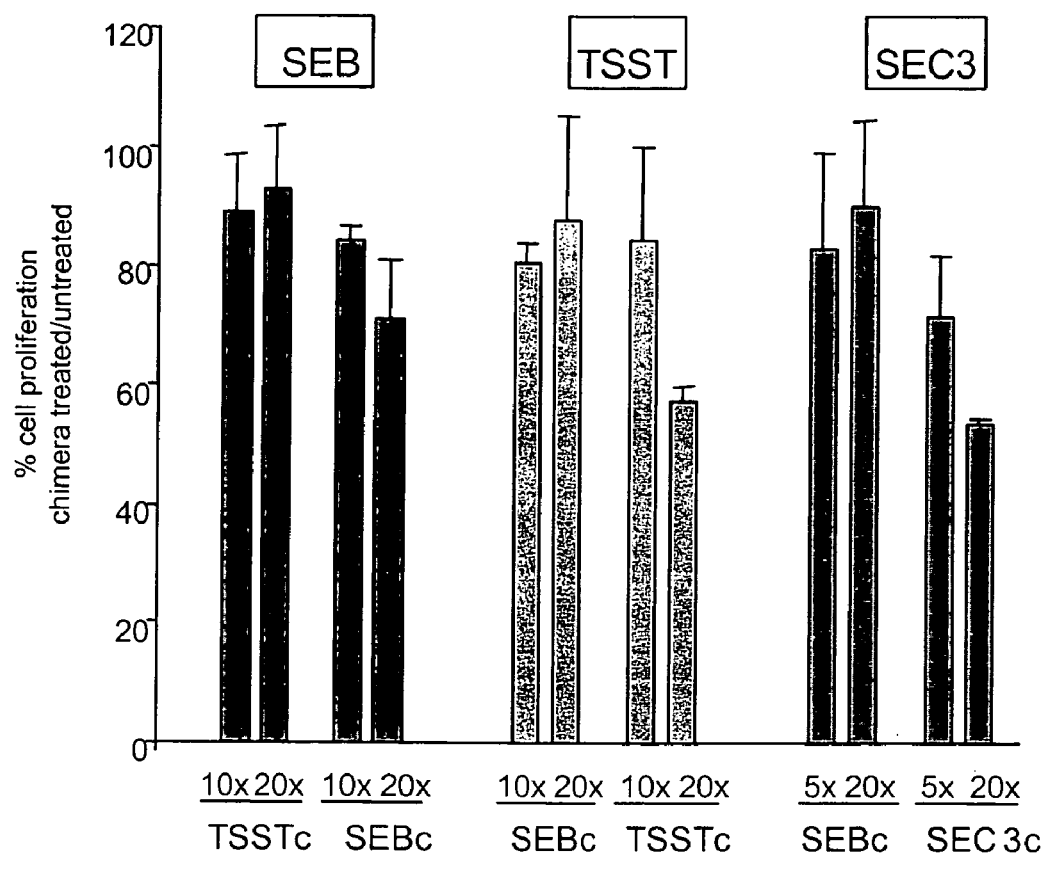

PBMCs/DCs (at a ratio of 20:1) were treated with either 1 nM TSST-1 or 1 nM SEC3. PBMCs alone were treated with 1 pM SEB in the absence or presence of increasing molar concentrations of the purified chimeras for 4 days. The results are shown in FIG. 6. In cells treated with SEB, a 20× concentration of SEBc inhibited cell proliferation by ~30% (FIG. 6). In comparison, a 20× concentration TSST-1c had a minimal effect on T cell proliferation in SEB-treated cells.

Stimulation with 1 nM TSST-1 or SEC3 exhibited a similar type-specific chimera inhibition of T cell proliferation. At 20× concentration, TSST-1c and SEC3c inhibited T cell proliferation by ~40% in TSST-1 stimulated cells and ~50% in SEC3 stimulated cells, respectively. SEBc did not significantly inhibit cell proliferation in either TSST-1 or SEC3 treated cells. These results are consistent with the cytokine release data, which showed that a chimeric protein can inhibit the cellular effects induced by the corresponding SAG against which it was designed. These type-specific interactions indicate that different TCRVβ sequences can be used to as specific ligands to differentiate between the various SAGs.

Example 2

Molecular Modeling

Materials and Methods:

A three-step molecular modeling study was conducted, as follows:

(I) The SAGs and their binding partners, MHC class II receptor and TCR, do not exhibit any significant structural changes upon complex formation. Also, structural studies indicate that SEB, SEC3 and TSST-1 engage in a similar spatial arrangement during contact with the MHC class II receptor (Sundberg and Mariuzza, 2002, Curr. Opin. Immunol. 14: 36-44; Arcus et al., 2002, J. Biol. Chem. 277: 32274-81). Thus, the initial models of the SAG/chimera complexes were constructed based on the crystallographic data as well as biochemical information on intermolecular contacts between DRα1/TCRVβ and the SAGs. The following crystal structures from the Protein Data Bank (PDB) were used: (1) 1SEB, 1SBB for the SEB-chimera complex, (2) 1JCK and 1SEB for the SEC3-chimera complex, and (3) 1SEB, 2TSS and 1FYT for the TSST-1-chimera complex. The DR1α model for all three chimeras was constructed from the single crystal structure of SEB-MHC class II (1SEB). BLAST (Altschul et al., 1997, Nucleic Acids Res. 25: 3389-402) searches against the PDB enabled us to identify structures with the highest sequence identity (88 to 24%) with the three different TCRVβ sequences (Vβ3, Vβ2, and modified Vβ8.2) used in the three chimeras. Homology modeling was applied to construct the initial models of the TCRVβ domains of the chimera (Sanchez and Sali, 1999, J. Comp. Phys. 151: 388-401).

The relative spatial positions of DR1α and TCRVβ with respect to the SAGs were derived from the three crystal structures: bipartite complexes (SEB-MHC class II: 1SEB), (SEB-TCR: 1SBB), and (SEC3-TCR: 1JCK) by superposition of the toxins. In the case of the TSST-1 complex, conserved structural features of the toxins such as the α-helices α1 and α3 (FIGS. 7 and 8) were chosen to orient the SAG in the complex. The relative positions of DR1α and TCRVβ with respect to TSST-1 were fixed based on structural studies (Kim et al., 1994, supra; Papageorgiou et al., 1996, supra). The linker $(GSTAPPA)_2$ was placed between the C-terminus of DR1α and the N-terminus of TCRVβ. Each SAG-chimera complex was minimized locally in vacuum without any constraints using the AMBER 4.1 force field (Pearlman et al., 1995, University of California, San Francisco); the parm94 parameter set was applied with a dielectric constant of 80 to a gradient limit$<10^{-2}$ kcal/mol $Å^2$.

(II) Molecular dynamics simulations of the three chimera-SAG complexes were performed at 300K for 200 ps in vacuum with a dielectric constant of 80 with the energy-minimized model as the t=0 configuration. Both, intra- and inter-molecular constraints were imposed in the simulation. All intra- and inter-molecular constraints were based on the available crystal structures (1SEB, 1SBB, 1JCK, 2TSS, 1FYT). Intramolecular constraints (force constants were set to 5 kcal/mol $Å^2$) were used to maintain the native folds of the SAGs, DRα1, and TCRVβ. The "weaker" intermolecular constraints (force constants set to 2 kcal/mol $Å^2$) were applied to allow movement and sufficient flexibility of the partners in the complex. Intermolecular contacts for the SEB-chimera complex were derived from the following crystal structures SEB-DRα1:1SEB and SEB-TCRVβ:1SBB.

Intermolecular contacts for the SEC3-chimera complex were adopted from the crystal structure of SEC3-TCRVβ complex (1JCK) and the observed interactions in the homologous crystal structure of DRα1-SEC2 complex (Kieke et al., 2001, supra). case of the TSST-1-chimera, experimental contact information is available only for the TSST-1-DRα1 (Kim et al., 1994, supra). No inter-molecular constraints wereinteraction employed between TSST-1 and TCRVβ. No constraints were applied to the $(GSTAPPA)_2$ (SEQ ID NO: 5)linker. After an equilibration period (~100 ps), 100 snapshots (one after every ps) were isolated for the 101-200 ps segment of the MD trajectory and minimized. An average structure of the 100 minimized snapshots was also calculated and minimized.

(III) A systematic analysis of the 100 minimized snapshots and the minimized average structure revealed the nature of various pair-wise interactions and their variations around the average values. A root-mean-square (RMS) matrix was computed for the 100 minimized snapshots to determine the conformational variations among the low-energy structures of each SAG-chimera complex. RMS deviations were also computed between the minimized average structure and each of the 100 minimized snapshots to identify snapshots that were most closely or distantly related to the minimized average structure of the complex. To define the pair-wise contacts between SAG and specific chimera, we calculated changes in solvent accessibility for each residue using the program MOLMOL (33) in the free SAG and the free chimera as well as in the SAG-chimera complex. A threshold of 3% change in the solvent accessible surface per residue was used to define a contact between the free SAG and the chimera due to complex formation. Thus, all residues, which show a change in solvent accessible surface larger than 3% upon complex formation are defined as contact residues.

Results:

Analyses of the SAG-Chimera Complexes:

To examine the structural basis for the type-specific behavior, molecular modeling studies were performed and the interactions between SEB, TSST-1, and SEC3 and their specific DRα1/linker/TCRVβ chimeras were compared. For each of the three complexes, the RMS-deviations for the backbone atoms were computed to be within 3.6 Å among the 100 minimized snapshots from the MD trajectory. Also, for each complex the RMS-deviations for the backbone atoms were computed between the minimized average structure and each of the 100 minimized snapshots. This value was always below 2.5 Å. These relatively low RMS deviations demonstrate that the minimized average structure is a representative model of the ensemble.

FIG. 7 shows stereoscopic ribbon models of the three complexes, i.e., SEB/SEBc, SEC3/SEC3c, and TSST-1/TSST-1c.

The DRα1 domain in the three chimeras forms an α/β fold with four anti-parallel β-strands, and one short and one long α-helix. The TCRVβ domain consists of an immunoglobulin-like β-fold containing seven β-strands that flank the complementarity determining regions CDR1, CDR2, and hypervariable loop HV4 loop (see FIG. 4).

The major contact areas of the DRα1 domain (cyan—loop 1, loop 2 and the long α-helix), the TCRVβdomain (blue—CDR1, CDR2 and HV4), as well as the linker region (red) are highlighted in FIG. 4. The contact regions, defined by the change in accessible surface per residue in the chimeras of the average minimized structures, are in agreement with the PDB structures (1SEB, 1SBB and 1JCK) and other structural studies (Kim et al., 1994, supra; Arcus et al., 2002, J. Biol. Chem. 277: 32274-81). Loop2 and the long α-helix of SEC3c show a more extensive contact interface with SEC3 in this model and indicate a slightly different orientation of the DRα-component toward SEC3 compared to the SEB complex. Crystallographic studies also suggest a slightly different binding mode of SEC3 to the MHC class II receptor compared to SEB (Arcus et al., 2002, supra).

MD simulations preserved all the major contact areas between the chimeras and their target SAGs. FIG. 8 depicts the residues of the SAGs (underlined) that have been reported to be in contact with DRα1 and TCRVβ. However, also observed were additional intermolecular contacts in the average minimized structure of the SAG-chimera complex. In the SEB-chimera complex, some additional contacts are K69 and N218 (DRα1), and N31, L58, and D206 (TCRVβ). For SEC3, N70, D199, and K218 form contacts with DRα, and L27 and K207 interact with TCRVβ. Finally, for the TSST-1-chimera, L26 and T57 interacts with DRαwhereas S17, K118, and D148 contacts TCRVβ.

Figure 7:
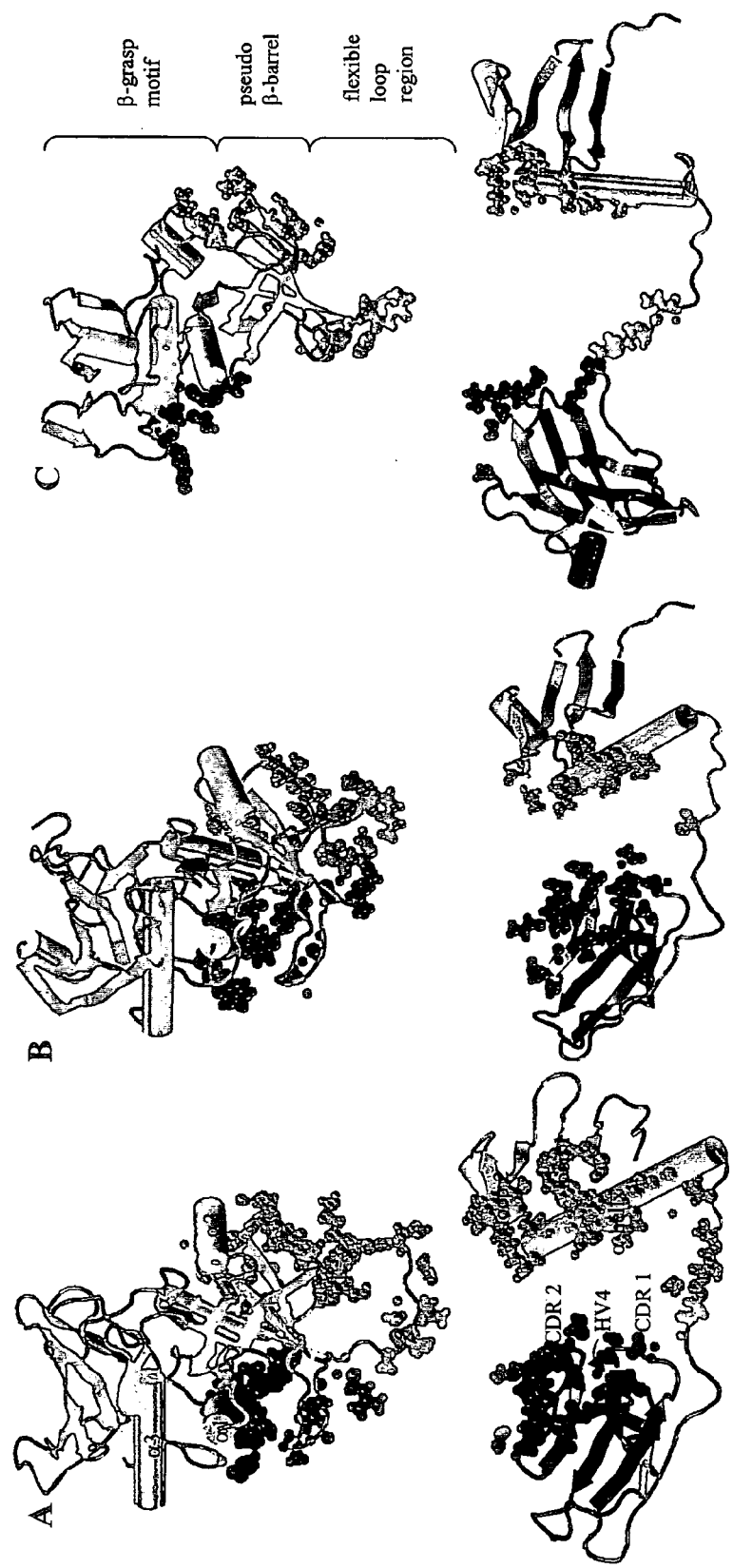
FIG. 7. Conformational variants of the three different superantigen-chimera complexes. The color code is as follows: superantigen in green, DRa in cyan, TcRVb in blue, and the linker in red. (A) Two minimized structures of each complex that are most different from each other out of 100 minimized MD-snapshots. These are for the SEB chimera complex (left): minimized snapshot at 118 and 187 ps (RMS=3.5 Å), for the SEC3 chimera complex (middle): minimized snapshot at 100 and 189. ps (RMS=3.2 Å) and for the TSST-1 chimera complex (right): minimized snapshot at 107 and 190 ps (RMS=3.6 Å). (B) Structures of the chimera that are most different (lighter shade) compared to the minimized average structure (darker shade). These are for the SEB chimera complex (left): minimized snapshot at 100 ps (RMS=2.3 Å), for the SEC3 chimera complex (middle): minimized snapshot at 100 (RMS=2.4 Å) and (C) the TSST-1 chimera complex (right): minimized snapshot at 108 ps (RMS=2.5 Å).

For each of the three SAG-chimera complexes, the molecular models show contacts between all three parts of the chimeras (DRα1, TCRVβ and linker) and the SAGs (see FIGS. 4, 7 and 8). The contact interfaces between DRα1 of the three chimeras and their target SAGs are quite similar in that they are all located on one side of the N-terminal β-barrel, which is preserved in all MHC class II/SAG complexes reported so far (Arcus et al., 2000, J. Mol Biol. 299: 157-68).

However as shown in FIGS. 7 and 8, the three complexes also reveal several distinctive features. The TCRVβ binding sites for SEB and SEC3 are located in the cleft between the N-terminal oligonucleotide binding-fold domain and C-terminal β-grasp domain (FIG. 7) (Fraser, 2000, supra). In contrast, in the TSST-1/TSST-1c complex, the contact interface with TCRVβ is located at the C-terminal end of the central α-helix (α3) and loop regions of the C-terminal β-grasp (FIG. 7).

The DRα1- and TCRVβ-binding epitopes on SEB and SEC3 are much closer in space compared to those in TSST-1. Triangular contacts in which SAG residues contact both the DRα1 and TCRVβ domains were detected in SEB/SEBc (Y89, Q92, C93, Y94, T107, K111) as well as in SEC3/ SEC3c (Y94, G102, K103, D209 Q210), but not in the TSST-1/TSST-1c (FIG. 8, purple highlighted residues). For the TSST-1/TSST-1c complex, the triangular contacts involve either contacts between TSST-1 residues and Drα1/linker (I42, E77, T79) or linker/TCRVβ (F20, S41, Y80, H82). In addition, SEB residues H105 and Q106 show contact with DRα1/linker, whereas D108 contacts the linker/Vβdomain. Similarly, L58 and N59 of SEC3 contact the linker/Vβ.

Analysis of Pair Wise Contacts Between SAGs and Their Respective Chimeras:

A detailed analysis of the pair-wise contacts between the SAGs and the specific chimeras reveals both similarities and differences in their specific binding behavior. In general, SEB and SEC3 contact their respective TCRVβ domains in a similar manner, whereas TSST-1 interacts with its Vβ domain in a distinctly different manner (FIG. 7).

Unique contacts between TSST-1 and TCRVβ are maintained at β8 and the central helix α3 (FIG. 8). Interactions between SEB or SEC3 and their respective Vβs are present in the loop region between β11/α4, which are not present in TSST-1. In addition, simultaneous DRα1 and TCRVβ contacts were only detected for SEC3 (residues 209, 210), but not for the corresponding residues in SEB. However, there are similarities for the TCRVβ contacts for all three SAGs, primarily in the region of α1, and at the loops between β2/β3 and α3/β10. TSST-1 contacts with Vβ in α1 are further extended into β1. In the loop region between β2 and β3, the specificity of contacts toward TCRVβ varies, in that SEB forms contacts with Vβonly, while SEC3 and TSST-1 maintains multiple Vβlinker contacts. Although all three SAGs maintain Vβ contacts in the loop region between α3/β10, the SAGs contact different binding sites in the Vβ domain (SEB-CDR2, SEC3-HV4, and TSST-1-CDR1).

All SAGs show DRαcontacts in the loop region between β1 and β2, as well as in the region of β3 and α2 (FIG. 8). These contacts are maintained for the different SAGs by all three contact areas of the DRα1 domain, loop 1, loop 2, and the long α-helix.

In TSST-1, the β3/α2-region (residues 43 to 58) shows a greater flexibility than that in SEB and SEC3. Thus, the contacts in TSST-1 are extended compared to SEB and SEC3 and include T57 and K58. Differences in the DRαcontacts are mainly located in the flexible loop and α4 regions. Both SEB and SEC3 show contacts involving these regions.

SEC3 maintains a slightly different relative orientation towards DRαcompared to SEB, thus forming additional contacts that extend from α4 toward β11. For TSST-1, the α4 contacts are missing, while the flexible loop region interacts with the TCRVβ and linker regions rather than DRα1. In addition, a tyrosine/DRα1 contact at residue 115 of β5 is only observed for SEB and SEC3. This contact stabilizes the SEB/ SEC3 specific salt bridge between SAG residue E67 and DRα1 residue K39. This specific salt bridge as well as the stabilizing tyrosine contact is missing in TSST-1. In addition, several hydrophobic interactions were detected, including contacts between SEB/SEC3 (F44, Y94) and DRαL60, and TSST-1 L30, I46, and DRα1 I63, A61, respectively.

The contact region between β4 and β5, which comprises the flexible loop region (FIG. 8, black underline), contains multiple contacts in all SAG models, and contacts in this area differ the most. All possible combinations of multiple contacts exist for SEB and SEC3, due to the close proximity of the contact epitopes of TCRVβ and DRα1. in this region and the flexibility of the linker. For TSST-1, the loop region contacts only the linker and TCRVβ domains, not the DRα1 domain. The loop region had been previously reported to contact the DRα1 and β chains, as well as the antigenic peptide (Kim et al., 1994). Possibly, the dynamic nature of the flexible loop region, common to all SAGs, may cause this difference.

Finally, these studies indicate that the (GSTAPPA)₂ linker can support simultaneous binding of the DRα1 and TCRVβ domains to all three SAGs, even though the spatial arrangement of the binding epitopes on the SAG surfaces are very different. Contacts to the linker were detected in the flexible loop region for all three SAGs and in the loop region between β2 and β3 for SEC3 and TSST-1. Differences in linker interactions (number of contact residues) are most likely due to the different spatial positions of the DRα1 and TCRVβ contact epitopes on the SEB/SEC3 and TSST-1 surface.

Example 3

Molecular Modeling

An initial model of the complex between the superantigen and its chimeric receptor (DRα-GSTAPPAGSTAPPA-TcRVβ) (DRα-SEQ ID NO: 5-TcRVβ) targeted against three superantigens SEB, SEC3, and TSST-1 was constructed as follows.

For the SEB complex, the crystal structures of SEB-MHC Class II and SEB-TcR complexes were used (PDB identifiers 1SEB and 1SBB). For the SEC3 complex, the crystal structures of SEC3-TcR and SEB-MHC Class II complexes were used (1JCK and 1SEB) whereas the TSST-1 complex was built from the crystal structures of TSST-1, SEB-MHC class II, and MHC class II-HA-peptide-TcR complexes (2TSS, 1SEB and 1FYT).

SEB, SEC3, and TSST-1 require binding with only DRα and TcRVβ for their pathogenicity and show no metal dependence or any MHC class II β-chain binding (Kotb, 1998, Curr Opin Microbiol 1: 56-65). The length and sequence of the DRα and TcRVβ domains were chosen to ensure their native folds as present in full-length MHC class II and TcR (Lehnert et al., 2001, supra).

Figure 12:
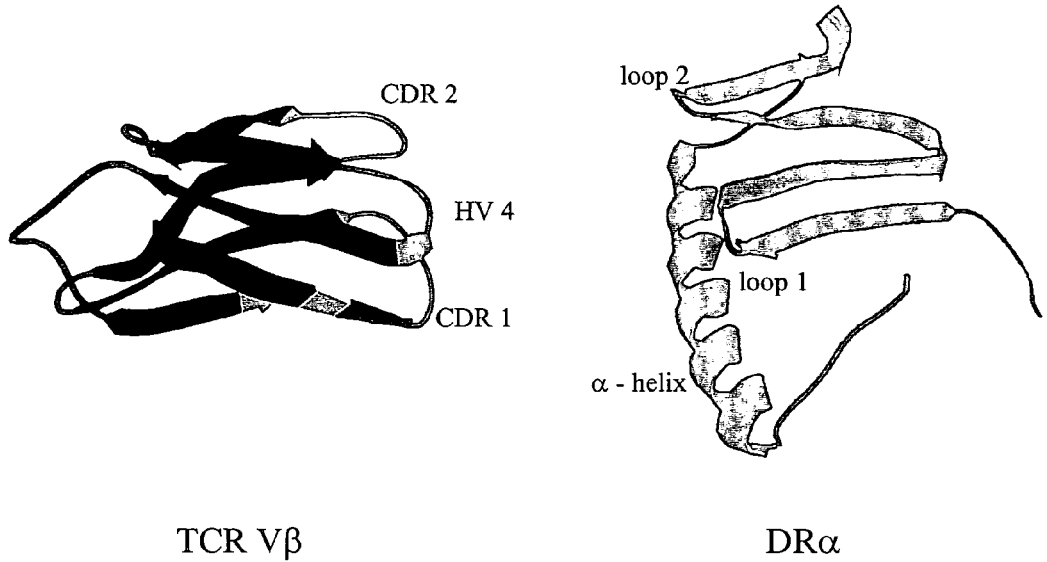
FIG. 12. Native fold of the major components of the chimeric protein. Ribbon diagram of crystal structures of MHC class II DRα (right, PDB identifier: 1SEB: A chain) and TcRVβ (left, PDB identifier: 1JCK: A chain). MHC class II DRα is in cyan and the TcRVβ is in blue with highlighted major contact areas to the superantigens (green). The designations of the major contact areas are given for DRα (loop1, loop2 and α-helix) and for TcRVβ (CDR1, CDR2 and HV4). Cysteine residues that form a disulfide bridge within TcRVβ are highlighted in yellow.

FIG. 12 shows the native folds of the domains that were used for the construction of the chimera. The DRα domain (FIG. 12, right panel) is a α/β fold with four anti-parallel β-strands and a long α-helix for DRα (cyan). Loop 1 and loop 2 as well as the long α-helix contain residues that contact the superantigen (highlighted in green). The DRα model in all complexes corresponds to the observed fold in the single crystal of SEB-MHC class II complex (1SEB). The immunoglobulin-like β fold of the TcR (blue) is shown at the left panel of FIG. 12. It consists of seven β-strands with the contact determining regions: CDR1, CDR2, and the hyper-variable loop HV4, that provide specific interactions with the superantigen (highlighted in green). Two invariant cysteines are retained in the sequence (highlighted in yellow) to facilitate the native fold via a disulfide bridge that remains invariant among all TcRVβ.

Three different TcRVβ sequences were selected because of their preferential binding to the toxins: human (h)TcRVβ3.0 for the SEB-specific chimera (Lehnert et al., 2001, supra), human (h)TcRVβ2.0 for the TSST-specific chimera (Choi et al., 1989, supra), and a mouse (m) analog of TcRVβ8.2 for the SEC3-specific chimera (Kieke et al., 2001, supra). Kieke and coworkers found a mutagenized variant of the single chain TcR, a Vβ8.2/Vβ3.1 fusion protein (mL2.1/A52V), with a 1000 fold increased binding affinity to SEC3. A truncated TcRVβ8.2 part of the Vβ8.2/Vα3.1 fusion protein was used to construct a SEC3 specific chimera and to model the interactions between SEC3 and TcRVβ.

A homology model of hTcRVβ3.0 was constructed using the closely related TcRVβ fold in the crystal structure of SEB-TcR complex, 29 residues of 1SBB were altered and optimized. Similarly, the TcRVβ fold in the crystal structure of SEC3-TcR complex was used to build a homology model of mTcRVβ8.3, nine residues of 1JCK were altered and optimized. Homology modeling was also used to get the molecular structure of the hTcRVβ2.0 sequence. The TcRVβ fold in the crystal structure of a MHC class II-HA peptide-TcR complex was selected, 66 residues of 1FYT were altered, and 3 residues were inserted and optimized. The structure with PDB identifier 1FYT was chosen since there is no experimental crystal structure of a TSST-1-TcR complex available and 1FYT showed the highest sequence identity (85%) to the required TSST1 specific binding sequence for the whole (correctly folded) Fab after a BLAST search against the Protein Data Bank (PDB).

Figure 11:
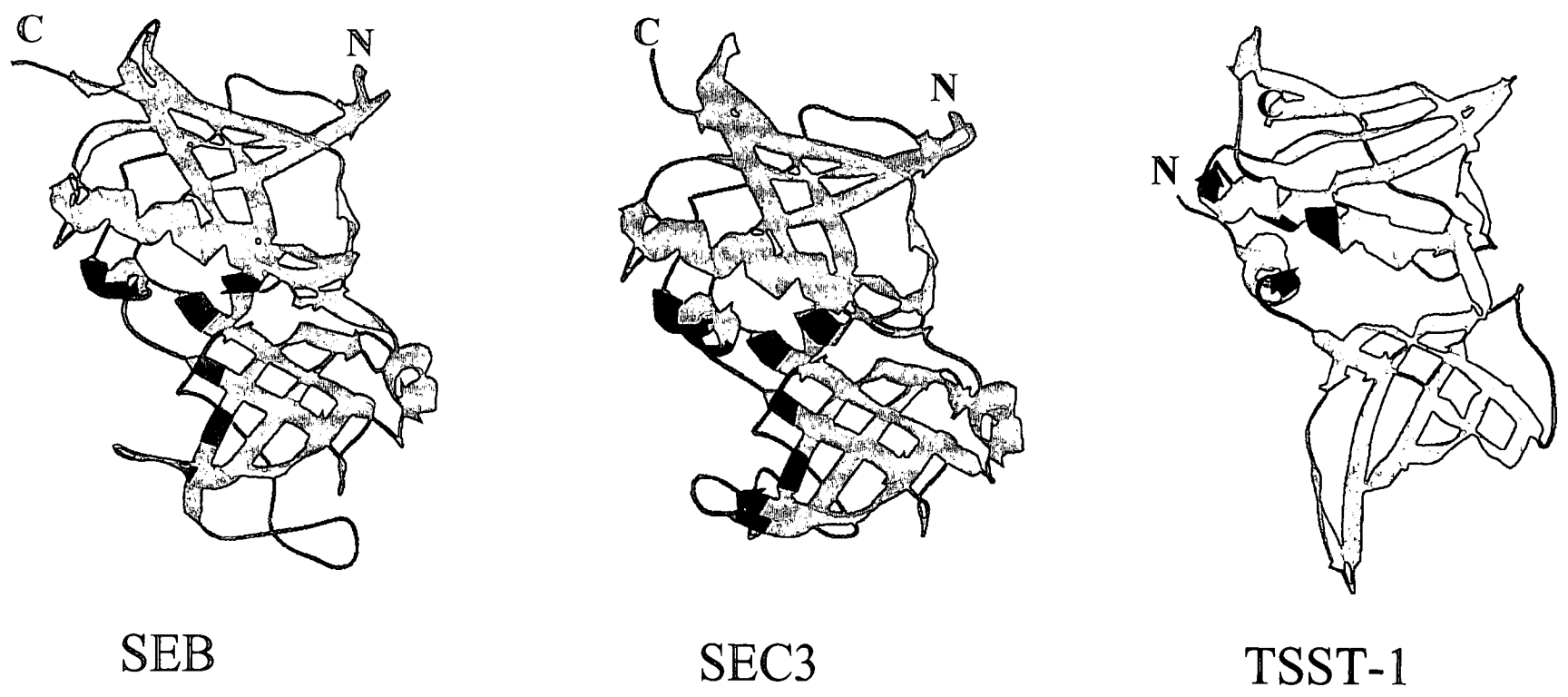

The spatial position and orientations of DRα and TcRVβ in the chimera with respect to the superantigen were derived mainly from the crystal structures of bipartite complexes such as (SEB-MHC class II: 1SEB), (SEB-TcR: 1SBB), (SEC3-TcR: 1JCK) by superposition of the toxins. In case of the TSST-1 complex, conserved structural features of the toxins such as the long central α-helix (FIG. 11) were chosen to orient the superantigen in the complex. The MHC and TcR components were positioned relative to TSST-1 by using information from literature (Kim et al., 1994, supra; Papageorgiou et al., 1996, supra). The linker (GSTAPPA)$_2$ was finally attached to connect the C-terminus of DRα with the N-terminus of TcRVβ. The superantigen-chimera complex was minimized locally in vacuum without any constraints using the AMBER 4.1 force field (Pearlman et al., 1995); the parm94 parameter set was applied with a dielectricity constant of 80 to a gradient limit<$10^{-2}$ kcal/mol Å$^2$.

The energy-minimized model was used as the starting configuration for constrained molecular dynamics (MD) at 300K in vacuum with a dielectric constant of 80 and a non-bonded cut-off distance of 12 Å. Intra- and inter-molecular constraints were derived from the available crystal structures. Three types of intramolecular constraints were imposed to maintain the native structure of the superantigen, the DRα and the TcRVβ: (i) all H-bonding distances (<2.5 Å) between the donor and acceptor atoms; (ii) $C^\alpha$-$C\alpha$ distances between β strands or inside the α-helix in the DRα component of the chimeric protein; and (iii) ranges of ±15° for the backbone torsion angles (φψ) to constrain the β strands in the TcR component of the chimeric protein. All intra- and inter-molecular constraints are based on experimental data of the available crystal structures that show: neither superantigen nor MHC class II or TcRVβ undergo significant structural changes upon complex formation (see structures 1SEB, 1SBB, 1JCK). The force constants were set to 5 kcal/mol Å$^2$ for the intra-molecular constraints. Inter-molecular pair-wise contacts involving atoms from a superantigen and its specific chimera were extracted from the crystal structures of bipartite complexes (SEB-MHC class II: PDB identifier 1SEB, 11 distance constraints, force constant=2 kcal/mol Å$^2$), (SEB-TcR: PDB identifier 1SBB, 11 distance constraints, force constant=2 kcal/mol Å$^2$), (SEC3-TcR: PDB identifier 1JCK, 6 distance constraints, force constant=2 kcal/mol Å$^2$), or from literature (TSST-1-MHC class II: (Kim et al., 1994, supra), 8 distance constraints, force constant=2 kcal/mol Å$^2$). No intermolecular constraints were employed between TSST-1 and its TcRVβ. 17 intermolecular constraints were imposed between SEC3 and DRα involving residues 45-50 and 88-93 on SEC3 (force constant=2 kcal/mol Å$^2$). These residues are common to interactions between many superantigens and DRα (Papageorgiou et al., 1996, supra). A MD run was performed for 200 ps. In all the three calculations, the equilibration was reached after 80 ps. Snapshots were collected every ps at the MD time scale of 101 to 200 ps. One hundred individual snapshots were minimized and analyzed. An average structure was obtained from the 100 snapshots and minimized with intra- and inter-molecular constraints described above with a dielectricity constant of 80 to a gradient limit<$10^{-2}$ kcal/mol Å$^2$.

A systematic analysis of the 100 minimized snapshots and the minimized average structure was performed. A root-mean-square (RMS) matrix was computed for the 100 minimized snapshots to determine the conformational variations among the low-energy structures of superantigen-chimera complex. RMS deviations were also computed between the minimized average structure and each of the 100 minimized snapshots to identify, which minimized snapshots were closely related to the representative minimized average structure of the complex and which ones were distantly related. The minimized average structure was a representative of the superantigen-chimera complex that retained the native structures of all its constituents. We applied two strategies to analyze the pair-wise contacts between superantigen and specific chimera. (I) Inter-molecular contacts were identified by computing distances between residues of DRα, TcRVβ, or linker to the superantigen within a 4 Å cut-off. (II) Changes in solvent accessibility per residue were computed for the free toxin and chimera and the toxin-chimera complex. A threshold of 3% change of the solvent accessible surface per residue was applied to define contacts between the free superantigen and the chimera due to complex formation.

Based on the analysis of the pair-wise contacts between the toxins and the specific chimeric proteins, mutations were suggested to improve the affinity of the chimeric proteins towards the superantigens. In principle, each contact interface is stabilized by three main contributions: (i) enthalpy gain from pair-wise interactions, (ii) change in free energy due to transfer of amino acids involved in pair-wise interactions from aqueous to non-aqueous environment of the contact interface between superantigen and chimera, and (iii) entropy loss due to freezing of the side chain motion in the contact interface. The contribution (iii) may not be mutually exclusive of contribution (ii).

There are several approaches published (Camacho et al., 1999, Biophys J 76: 1166-1178; Kierzek and Zielenkiewicz, 1997, Acta Biochim Pol 44: 549-556; Zhang et al., 1997, J Mol Biol 267: 707-726; Olson, 1998, Biophys J 81: 1841-1853) to calculate interaction energies. A simple empirical approach that estimates contribution (i) and (ii) to evaluate whether an amino acid substitution on any of the six binding epitopes and the linker of a chimera has stabilizing effect was used in this analysis.

Interaction energies between the toxin and the chimera were estimated from contributions from the force field energies (enthalpic contribution) and estimates of free transfer energies due to hydrophobic or polar interactions.

The enthalpic contributions ($\Delta H$) were obtained from energy calculations with the GROMOS force field (van Gunsteren et al., 1996, Biomolecular Simulation: The GROMOS96Manual and Use Guide. Vdf Hochschulverlag AG an der ETH Zürich: Zurich, Switzerland; 1-1042). SWISS-MODEL was used for a fast calculation of the relative enthalpic contributions (Guerex et al 1998, supra). The enthalpy ($\Delta H$) of the average minimized structure of the original superantigen-chimera complex (O) as well as the mutated one (X) was computed according to Equation 1.

$$\Delta H_{O \text{ or } X} = H_{complex} - (H_{toxin} + H_{chimera}) \quad \text{Eq. 1}$$

The mutated complex carries single site substitutions on the chimera. The enthalpic contribution ($\Delta\Delta H$) due to mutations was calculated as follows (Equation 2):

$$\Delta\Delta H_{OX} = \Delta H_X - \Delta H_O \quad \text{Eq. 2}$$

The change in free transfer energy, due to substitution of an amino acid, depends on the hydrophily/hydrophobicity of its side chain and the change in accessible surface from free to complex state. White and Wimley (White et al. 1999, Ann Rev Biophys Biomol Str 28: 319-365) developed an experimental based "Whole-Residue Hydrophobicity Scale" ($E_x$) to account different hydrophily/hydrophobicity of amino acids for a transfer from aqueous to non-aqueous environment, i.e. the contact interface. Jayasinghe and coworkers (Jayasinghe et al., 2001, J Mol Biol 312: 927-934) extended the "Whole-Residue Hydrophobicity Scale" of White and Wimley (White et al. 1999, supra) to salt bridges. The scale of White and Wimley provides a relative measure of free energy necessary to substitute an amino acid depending on its hydrophilicity/hydrophobicity. It was of interest to derive a parameter that describes the relative change of the free transfer energy due to relative change of solvent accessible surface for the substitution of an original residue (O) by a mutant residue X. In order to get a relative change of the accessible surface, a glycine pentapeptide is used as reference. The change in accessible surface is described in Equation 3 relative to the glycine standard.

$$A_X = A_{GGXGG} - \Delta A_{GGGGG} \quad \text{Eq. 3}$$

All solvent accessible surfaces were calculated by using the program MolMol (Koradi et al., 1996 J Mol Graphics 14: 51-55).

Equation 4 describes the free transfer energy in dependence of the change in accessible surface for a residue X:

$$k_X = E_X / (\Delta A_X) \quad \text{Eq. 4}$$

In case of a substitution of a residue O by a residue X, Equation 4 needs also to be applied to the original residue O.

The free transfer energy parameter per change of solvent accessible surface is calculated according to Equation 5 for the special mutation of residue O to residue X.

$$\Delta K_{OX} = k_X - k_O \quad \text{Eq. 5}$$

The change in accessible surface ($\Delta A$) due to a single site mutation within the chimera was calculated according to Equation 6.

$$\Delta A_{OX} = A_X - A_O \quad \text{Eq. 6}$$

Finally, the change of interaction energy due to a single site mutation of a residue O to a residue X corresponds to:

$$\Delta G_{OX} = \Delta\Delta H_{OX} - \Delta K_{OX} \Delta A_{OX} \quad \text{Eq. 7}$$

The mutated complex as well as the mutated chimera was conformational analyzed and energy minimized using GROMOS (van Gunsteren et al., 1996, supra). For a given substitution, an empirical criterion was chosen to decide if the substitution has stabilizing, destabilizing, or if the substitution has no effect on the superantigen-chimera complex. Negligible or no effect was stipulated if the energy difference is close to thermal energy (0.6 kcal/mol). It was expected that the substitution should have stabilizing or destabilizing effect depending upon the sign in the energy change if the difference is twice the thermal energy or higher.

Results:

Experimental studies revealed that chimeric receptors designed to target three superantigens SEB, SEC3, and TSST-1 were indeed capable of blocking superantigen pathogenesis in a type-specific manner (Example 1, supra). Modeling studies were carried out to determine how the DRα and TcRVβ domains in the specific chimeras interact with their respective epitopes on the different superantigens. It was also of interest to examine whether the same (GSTAPPA)$_2$ (SEQ ID NO: 5) linker could connect the DRα and TcRVβ domains that the two domains in the chimeras are able to interact with different superantigens in type-specific manner.

Figure 13A:
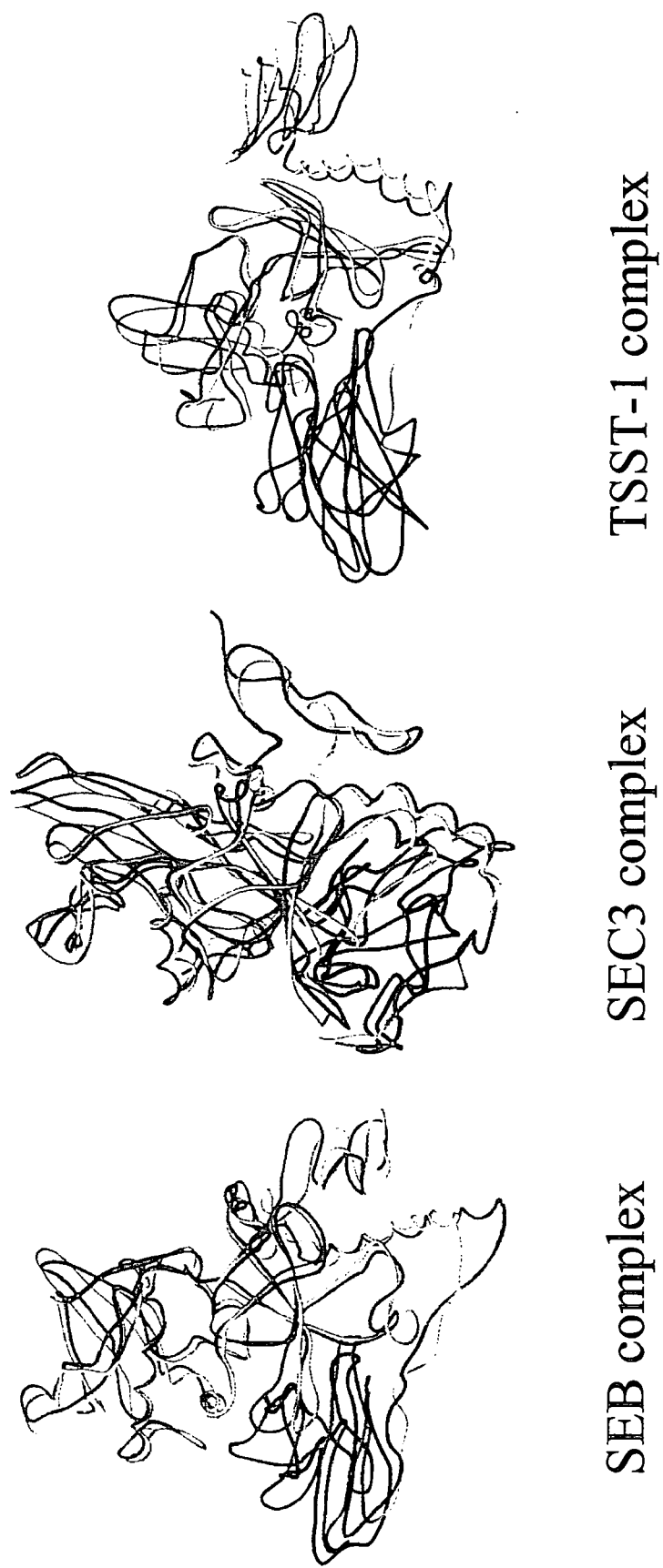
FIG. 13. Conformational variants of the three different superantigen-chimera complexes. The color code is as follows: superantigen in green, DRα in cyan, TcRVβ in blue, and the linker in red. (A) Two minimized structures of each complex that are most different from each other out of 100 minimized MD-snapshots. SEB chimera complex (left); minimized snapshot at 118 and 187 ps (RMS=3.5 Å). SEC3 chimera complex (middle); minimized snapshot at 100 and 189 ps (RMS=3.2 Å). TSST-1 chimera complex (right); minimized snapshot at 107 and 190 ps (RMS=3.6 Å). (B) Structures of the chimera that are most different (lighter shade) compared to the minimized average structure (darker shade). SEB chimera complex (left); minimized snapshot at 100 ps (RMS=2.3 Å). SEC3 chimera complex (middle); minimized snapshot at 100 (RMS=2.4 Å). TSST-1 chimera complex (right); minimized snapshot at 108 ps (RMS=2.5 Å).
Figure 13B:
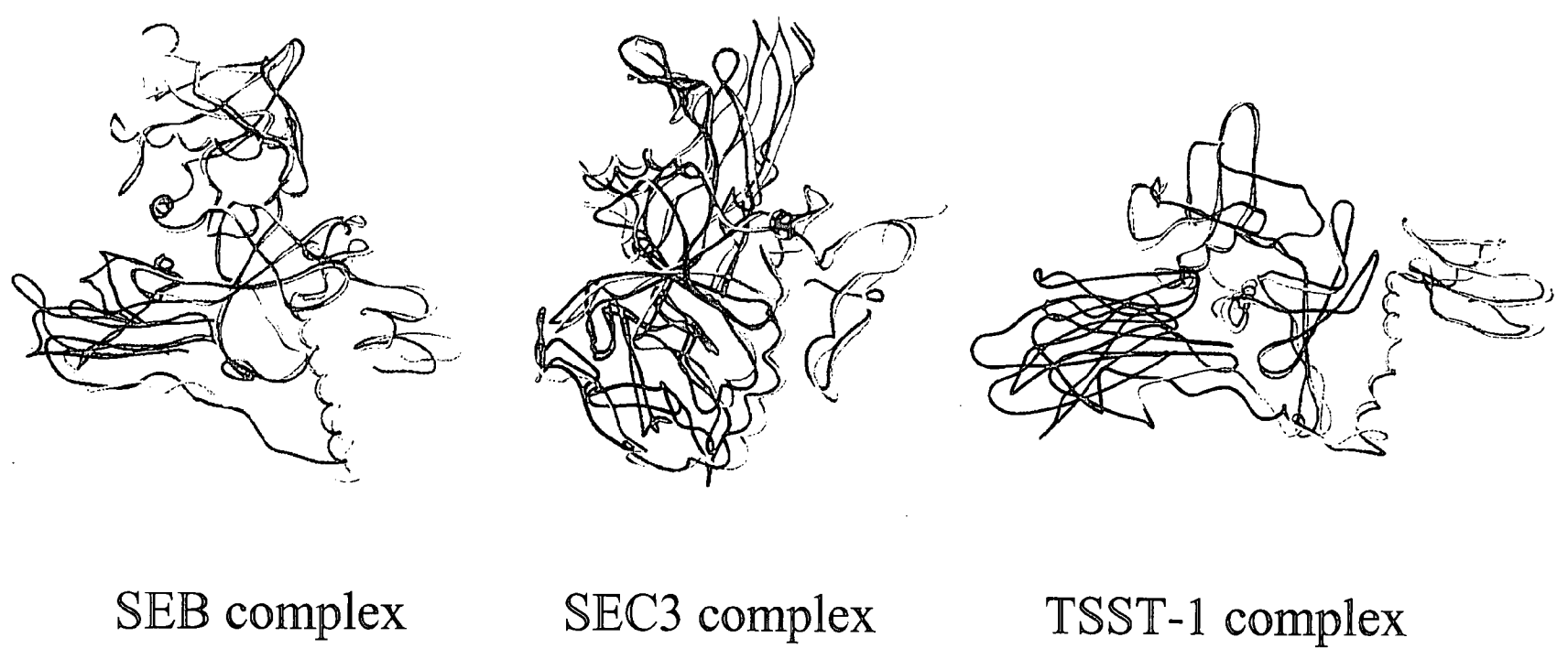

Conformational variants of the three different superantigen-chimera complexes are shown in FIG. 13. The conformational variants are captured in two different ways. FIG. 13A shows the two minimized structures of each complex that are most different from each other. FIG. 13B shows the structures of the chimera that are most different from the minimized average structure (shown in darker shade). The minimized SEB-chimera snapshots (FIGS. 13A and B, left panel) at 118 and 187 ps are the most different from each other (RMS=3.5 Å) whereas the minimized snapshots at 100, 112 (not shown), and 185 ps (not shown) are the most different from the minimized average structure (RMS=2.3-2.1 Å respectively). The minimized SEC3-chimera snapshots (FIGS.>13A and B, middle panel) at 100 and 189 ps are most different from each other (RMS=3.2 Å) whereas the minimized snapshots at 100, 172 (not shown), and 194 ps (not shown) are most different from the minimized average structure (RMS=2.4-1.8 Å respectively). The minimized TSST-1-chimera snapshots (FIGS. 13A and B, right panel) at 107 and 190 ps are the most different from each other (RMS=3.6 Å) whereas the minimized snapshots at 108 and 187 ps (not shown) are the most different from the minimized average structure (RMS=2.5-2.1 Å). The deviations among the structural variants for each complex are small and all the variants show folding similar to that of the average minimized structure. Thus, the average minimized structures are representative for the 100 conformational variants of each complex.

Figure 14:
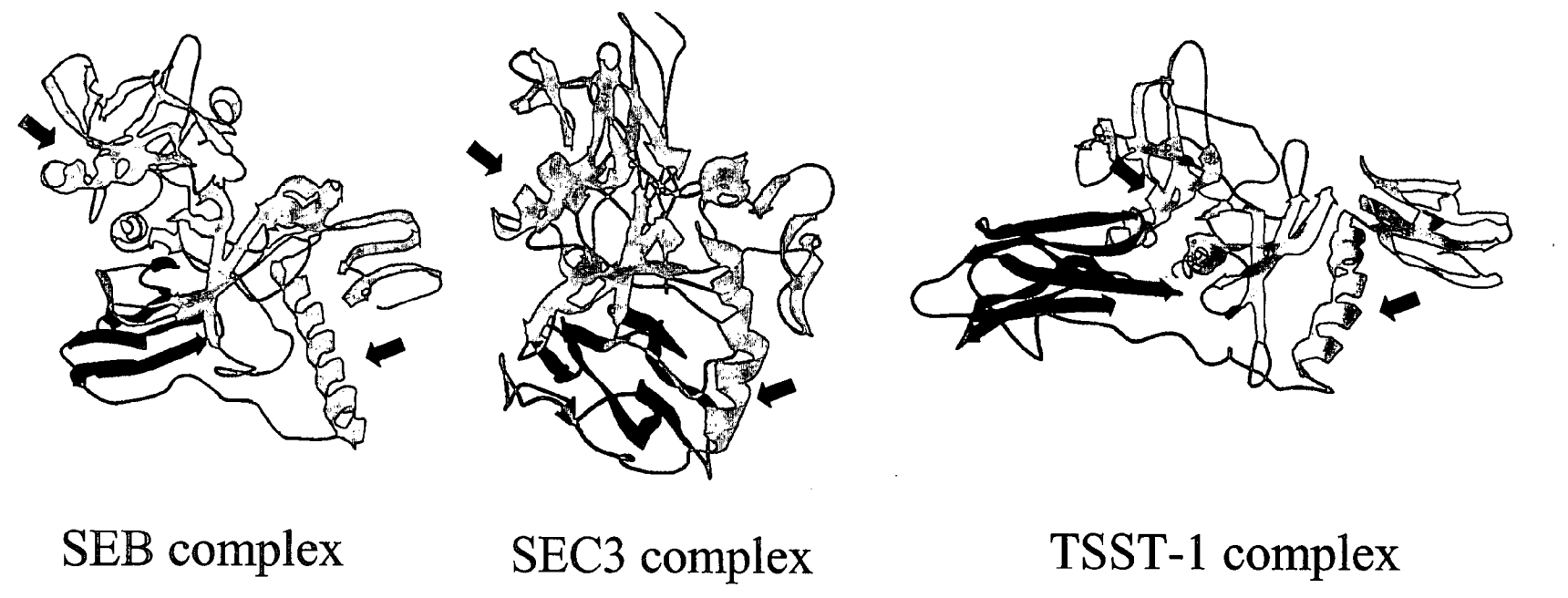

FIG. 14 compares the average minimized structures of the three superantigen-DRα-linker-TcRVβ complexes. The position and orientation of TcRVβ relative to the central α-helix of the superantigens are different in the three chimeras: in the TSST-1-chimera complex, the TcRVβ domain is much closer to the central superantigen α-helix compared to the SEB- and SEC3-chimera complexes. Although the same (GSTAPPA)₂ (SEQ ID NO: 5)linker can support the simultaneous binding of the DRα and TcRVβ domains to their respective superantigens, these two domains maintain different spatial relationship with each other for the three chimeras. In all the three chimeras, the linker regions show stable contacts with the superantigens.

Figure 15A:
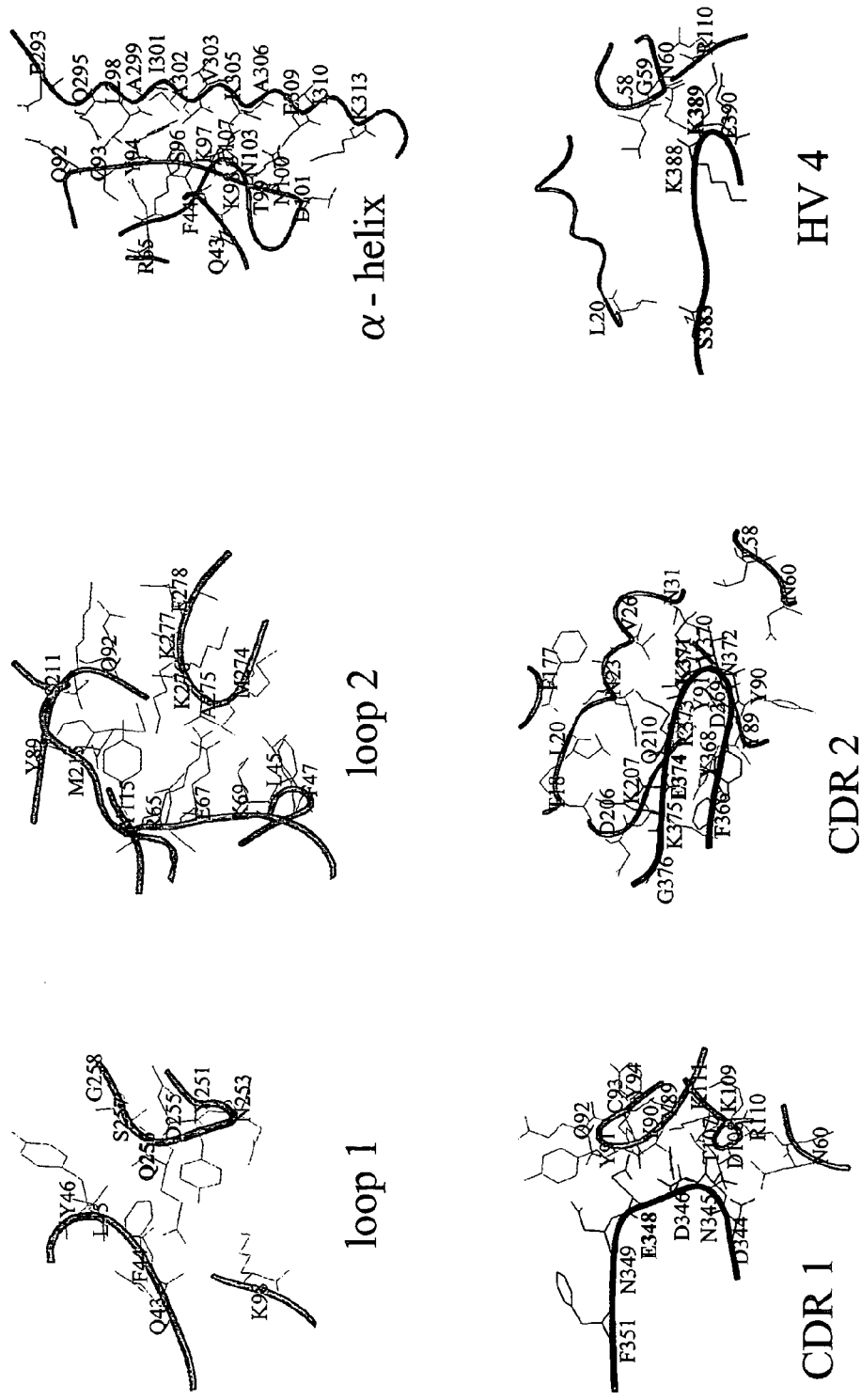
FIG. 15. Close-up view of major contact epitopes for the superantigen-chimera-complexes 15A, SEB-chimera complex; 15B, SEC3-chimera complex; 15C, TSST-1-chimera complex. The color code is as follows: superantigen in green, chimera components: DRα in cyan, TcRVβ in blue. There are three specific contact epitopes for DRα1 loop1, loop2, and the C-terminal α-helix, and also three specific contact epitopes for TcRVβ: CDR1, CDR2, and HV4 of the chimera molecules and their target superantigens. The contact residues are indicated, highlighted residues stand in connection with mutation suggestions. Contacts to the linker are not shown.

There are three major contact epitopes: loop1, loop2, and the C-terminal α-helix within DRα (cyan) of the chimera and also three major contact epitopes, CDR1, CDR2, and HV4 (blue) within TcRVβ of the chimera (FIG. 12). FIGS. 5A-C show the close-up of specific contacts between the three specific chimera molecules and their target superantigens from the minimized average structures. The contacts are within distance threshold of 4 Å between toxin and chimera. All the conformational variants of the SEB-chimera retain the inter-molecular contacts as observed in the experimental crystal structures. The underlined residues highlight contacts of the experimental structures within a 4 Å cut-off for comparison between computer model and experimental structure. SEB residues Q43,F44,L45,Y46,F47, R65, E67,K69,Y89,Q92, C93, Y94,S96,K97,K98,T99,N100,D101,N103,T107,Y115,S211, M215 show DRα contacts (FIG. 15A, top panels). There is only one SEB residue (D209) that shows a contact in the experimental structure 1SEB with Q295 inside the α-helix of MHC class II that was not observed in the minimized average structure within the distance threshold of 4 Å (FIG. 15A). The epitope containing D209 of SEB is common to both MHC class II and TcRVβ. During the MD time frame of 100 ps, the described contact appears only in 10% of the snapshots. Thus, this contact does not show up in the average minimized structure. The residue D209 is also not mentioned as a contact residue in other references we used for comparison (Papageorgiou et al., 1996, supra).

All experimentally determined intermolecular interactions between SEB and TcRV□in 1SBB are retained by the average minimized structure: T18,L20,N23,V26,N31,L58, G59, N60, Y89, Y90,Y91, Q92, C93, Y94, T107, D108,K109,R110, K111, F177,D206, K207, Q210 maintain TcRVα contacts in the minimized average structure of the SEB-chimera complex (FIG. 15A, lower panels). Residues H105, Q106, T107, D108 of the flexible loop region of SEB are involved in contacts to the flexible linker between DRα and TcRVβ of the chimera (not shown).

Most of the inter-molecular contacts are retained by the conformational variants of the SEC3-chimera complex. SEC3 residues: L45,A46,H47,E67, L68, L69,E71,N92, C93, Y94,F95,S96, N100, V101, G102, K103, Y112, Q210, S211,K212, K218, D219 contact DR□(FIG. 15B, top panels) Inter-molecular contacts that are reported for the SEC2 analog in the literature (Papageorgiou et al., 1996, supra) are underlined. Five contact residues for SEC2 mentioned by Papageorgiou et al., namely K43, F44, K65, Y89 and M215 are not found in the SEC3-DRα interaction of the minimized average structure within the 4 Å cut-off.

An in depth analysis of the trajectory revealed low frequencies for those contact residues, i.e. K43 and F44 are only in 8% of the snapshots in contact with loop1, K65 shows contacts to loop 2 only in 4% of the snapshots, Y89 and M215 show contacts to the α-helix in 17% and 15% of all snapshots respectively. There is a low frequency of these specific contacts; thus, these contacts cannot be observed in the minimized average structure. All experimentally observed contacts between SEC3 and the TcRVβ were retained for the minimized average structure. Contact residues within the 4 Å cut-off between SEC3 and TcRVβ of the crystal structure (1JCK) are underlined. SEC3 residues. T18, G19,T20,N23,Y26, L27, L58,N60,Y90,V91, Y94, G102,K103,V104,T105,S106, G107, F176,N177, D206, K207, F208, D209, Q210, Y213 interact with TcRV□ (FIG. 15B, lower panels). SEC3 residues K56, K57, L58, N59 and D62 are in contact with the linker of SEC3 specific chimera (not shown).

FIG. 15C provides a close up view of the specific contacts between the TSST-1 and the TSST-1 specific chimera for the minimized average structure. Most of the inter-molecular contacts of TSST-1 to DRα are retained as reported in Kim et al., 1994, supra, in the minimized average structure (underlined residues). TSST-1 residues: L26, D27, N28, S29,L30,G31,S32,R34,L36,I42,L44,I46,F47,P48, S49, P50,S53, T57, K58, T79 maintain DRα contacts (FIG. 15C, upper panels). Kim et al., 1994, supra, suggest that F83 and I85 of TSST-1 contact V259 in the α-helix of DRα. In the present model, contacts of F83 and I85 were missing. Instead, a contact of T79 to the α-helix was identified, as well as contacts of Y80 and H82 to CDR1 (FIG. 15C, lower panels). Residues T79, Y80 and H82 are in close proximity to residue F83 and I85 of TSST-1 and V259 of DRα.

The described TSST-1 residues 79 to 85 are located in the flexible loop area. Due to the dynamic nature of the flexible loop, the contacts within this area show high fluctuations. Eight residues in the flexible loop encompassing T69-I81of the crystal structure are also showed in contacts to DRP and the antigenic peptide in the crystal structure (Kim et al., 1994, supra). Since neither a DRβ part nor an antigenic peptide was included in this model, these contacts may not have been identified by these calculations.

All inter-molecular contacts of TSST-1 residues with TcRVβ (Papageorgiou et al. 1996, supra) (underlined residues) were maintained in the minimized average structure of the TSST-1-chimera complex, and thus for all the conformational variants of the TSST-1-chimera complex. TSST-1 residues: L10, Y13, S14, S15.G16, S17, D18, T19, F20, T21, T38, D39, N65, R68, K71, H74, Y80, H82, K114, Y115, W116, P117, K118, K121, F131, E132,H135, Q136, L137,Q139,I140,H141, G142, Y144, R145, S146 make contact to TcRVβ (FIG. 15C, lower panels). TSST-1 residues D39, G40, S41, S76, E77, G78 and Y80 are in contact with the linker of TSST-1 specific chimera (not shown).

Detailed analysis of the contact interface provided clues for specific mutations that might improve the binding of the specific chimeras to the superantigens. In order to judge the suggested mutations, relative changes in free energies of interaction due to a single site mutation were estimated. Table II lists the energy estimates for the change of interaction energies as well as the energy contributions according to Equation 7. A negative sign indicates an improved binding due to a single site mutation. Only data with interaction energy changes higher than twice the thermal energy (0.6 kcal/mol) are presented.

TABLE II

ESTIMATES OF CHANGES IN FREE INTERACTION ENERGY
($\Delta G$ IN KCAL/MOL) DUE TO SINGLE SITE MUTATIONS

| complex of | mutant | location | $\Delta\Delta H_{OX}$ | $\Delta A_{OX}$ | $\Delta K_{OX}$ | $\Delta K_{OX}\Delta A_{OX}$ | $\Delta G_{OX}$ |
|---|---|---|---|---|---|---|---|
| SEB with specific chimera | Q256I | loop 1 | −0.65 | −21.0 | −0.027 | +0.57 | −1.2 |
| | G323S | linker | +1.30 | +34.0 | −0.004 | −0.13 | +1.4 |
| | E348T | CDR1 | −0.31 | −19.9 | −0.051 | +1.02 | −1.3 |
| | K371Y | CDR2 | +3.31 | +27.7 | −0.027 | −0.74 | +4.1 |
| | E374T | CDR2 | −0.46 | −31.3 | −0.051 | +1.60 | −2.1 |
| | S383F | HV4 | −3.03 | +46.0 | −0.026 | −1.19 | −1.8 |
| | K389Q | HV4 | −1.01 | −34.4 | −0.007 | +0.24 | −1.3 |
| SEC3 with specific chimera | E279T | loop 2 | −1.31 | −52.5 | −0.051 | +2.69 | −4.0 |
| | E285I | loop 2* | −0.73 | −7.5 | −0.070 | +0.52 | −1.3 |
| | F293Q | αhelix* | −1.18 | +11.2 | +0.029 | +0.33 | −1.5 |
| | I302N | αhelix | −1.94 | +2.8 | +0.027 | +0.08 | −2.0 |
| | P328N | linker | −1.23 | +21.0 | +0.010 | +0.21 | −1.4 |
| | G331V | linker | −1.85 | +6.3 | −0.024 | −0.15 | −1.7 |
| | G372T | CDR2 | +1.55 | +19.1 | −0.009 | −0.18 | +1.7 |
| | G372V | CDR2 | +2.10 | +30.6 | −0.024 | −0.75 | +2.8 |
| | G374V | CDR2 | +1.27 | +27.2 | −0.024 | −0.66 | +1.9 |
| | N375T | CDR2 | −1.64 | −6.7 | −0.008 | +0.06 | −1.7 |
| | E377Q | CDR2 | −1.72 | +8.7 | −0.042 | −0.37 | −1.4 |
| | P390T | HV4 | −2.26 | +33.7 | +0.001 | +0.05 | −2.3 |
| | P390N | HV4 | −2.47 | +54.8 | +0.010 | +0.54 | −3.0 |
| TSST-1 with specific chimera | Y207E | loop1 | −0.14 | +26.9 | +0.062 | +1.67 | −1.8 |
| | Q212E | loop1 | +3.79 | −20.6 | +0.042 | −0.87 | +4.7 |
| | M230F | loop2 | +1.41 | +53.0 | −0.008 | −0.44 | +1.9 |
| | M230Y | loop2 | +1.41 | +57.7 | +0.001 | +0.06 | +1.3 |
| | A231H | loop2 | −0.09 | +71.1 | −0.019 | −1.38 | +1.3 |
| | A231I | loop2 | −0.12 | +44.1 | −0.035 | −1.56 | +1.4 |
| | A231L | loop2 | −0.16 | +49.3 | −0.036 | −1.76 | +1.6 |
| | A231M | loop2 | 0.00 | +71.8 | −0.029 | −2.09 | +2.1 |
| | A231F | loop2 | +0.03 | +100.1 | −0.037 | −3.75 | +3.8 |
| | Q251H | αhelix | +1.39 | +38.3 | −0.011 | −0.44 | +1.8 |
| | Q251K | αhelix | +2.37 | +72.5 | +0.007 | +0.51 | +1.9 |
| | Q251M | αhelix | +0.78 | +66.0 | −0.021 | −1.38 | +2.2 |
| | Q251F | αhelix | +2.09 | +57.8 | −0.029 | −1.69 | +3.8 |
| | K261Q | αhelix | +1.12 | +4.8 | −0.007 | −0.03 | +1.2 |
| | K261H | αhelix | +1.03 | +38.3 | −0.018 | −0.70 | +1.7 |
| | E265T | αhelix | −0.06 | −24.4 | −0.051 | +1.25 | −1.3 |
| | K269E | αhelix | −0.01 | −38.0 | +0.035 | −1.34 | +1.3 |
| | P284N | linker | +2.70 | +14.3 | +0.010 | +0.14 | +2.6 |
| | T314N | CDR1 | +1.27 | −14.7 | −0.009 | −0.12 | +1.4 |
| | A355Y | HV4 | −0.28 | −57.3 | −0.028 | +1.60 | −1.9 |

The type of complex (SEB, SEC3, and TSST-1) is provided as well as mutation options in order to judge the binding ability of the chimera to the toxins. The location within the super-antigen specific chimera correlates with FIG. 15, a * indicates a "close by" location. At column 4 to 8, the estimates for the contributions to the changes in free interaction energy are given according to eq. 7. $\Delta\Delta H_{OX}$ (in kcal/mol) is the enthalpic contribution. $\Delta A_{OX}$ (in Å$^2$) stands for the change in solvent accessible surface. $\Delta K_{OX}$ (in kcal/mol Å$^2$) is an empirical coefficient for the change in free interaction energy per change in accessible surface and corresponds to the hydrophilicity/hydrophobicity of a specific amino acid exchange. $\Delta K_{OX}\Delta A_{OX}$ (in kcal/mol) is anestimate for the change in free energy of transfer due to a single site mutation.

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. An anti-*Staphylococcus aureus* enterotoxin C3 (SEC3) chimera, comprising the amino acid sequence of SEQ ID NO: 9.

2. The chimera according to claim 1, further comprising an amino acid sequence that permits attachment to a solid phase.

3. The chimera according to claim 2, wherein the amino acid sequence that permits attachment to a solid phase is a HIS tag sequence.

* * * * *